(12) United States Patent
Kisak et al.

(10) Patent No.: US 9,308,181 B2
(45) Date of Patent: *Apr. 12, 2016

(54) TOPICAL FORMULATIONS, SYSTEMS AND METHODS

(71) Applicant: Nuvo Research Inc., Mississauga (CA)

(72) Inventors: Edward T. Kisak, San Diego, CA (US); John M. Newsam, La Jolla, CA (US); Dominic King-Smith, San Diego, CA (US); Pankaj Karande, Troy, NY (US); Samir Mitragotri, Santa Barbara, CA (US); Tejas Desai, Mississauga (CA); Wade A. Hull, Kaysville, UT (US)

(73) Assignee: Nuvo Research Inc., Mississauga (CA)

( * ) Notice: Subject to any disclaimer, the term of this patent is extended or adjusted under 35 U.S.C. 154(b) by 413 days.

This patent is subject to a terminal disclaimer.

(21) Appl. No.: 13/791,460

(22) Filed: Mar. 8, 2013

(65) Prior Publication Data

US 2013/0337031 A1    Dec. 19, 2013

Related U.S. Application Data

(63) Continuation-in-part of application No. 13/680,623, filed on Nov. 19, 2012, now Pat. No. 8,513,304, which is a continuation of application No. 12/848,792, filed on Aug. 2, 2010, now Pat. No. 8,343,962, which is a continuation-in-part of application No. 12/281,561, filed as application No. PCT/IB2007/001983 on Mar. 6, 2007, now Pat. No. 7,795,309.

(60) Provisional application No. 60/778,847, filed on Mar. 6, 2006.

(51) Int. Cl.

| A61K 31/196 | (2006.01) |
| A61K 31/405 | (2006.01) |
| A61K 9/70 | (2006.01) |
| A61K 31/192 | (2006.01) |
| A61K 31/40 | (2006.01) |
| A61K 31/407 | (2006.01) |
| A61K 31/5415 | (2006.01) |
| A61K 47/14 | (2006.01) |
| A61K 31/19 | (2006.01) |
| A61K 31/195 | (2006.01) |
| A61K 31/444 | (2006.01) |
| A61K 9/00 | (2006.01) |
| A61K 9/06 | (2006.01) |
| A61F 7/03 | (2006.01) |
| A61K 47/12 | (2006.01) |
| A61K 47/18 | (2006.01) |
| A61K 47/20 | (2006.01) |
| A61K 45/06 | (2006.01) |
| A61K 31/568 | (2006.01) |
| A61K 31/137 | (2006.01) |
| A61K 31/167 | (2006.01) |
| A61K 31/245 | (2006.01) |
| A61F 7/02 | (2006.01) |

(52) U.S. Cl.
CPC . *A61K 9/703* (2013.01); *A61F 7/03* (2013.01); *A61K 9/0014* (2013.01); *A61K 9/06* (2013.01); *A61K 9/7084* (2013.01); *A61K 31/137* (2013.01); *A61K 31/167* (2013.01); *A61K 31/19* (2013.01); *A61K 31/192* (2013.01); *A61K 31/195* (2013.01); *A61K 31/196* (2013.01); *A61K 31/245* (2013.01); *A61K 31/40* (2013.01); *A61K 31/405* (2013.01); *A61K 31/407* (2013.01); *A61K 31/444* (2013.01); *A61K 31/5415* (2013.01); *A61K 31/568* (2013.01); *A61K 45/06* (2013.01); *A61K 47/12* (2013.01); *A61K 47/14* (2013.01); *A61K 47/183* (2013.01); *A61K 47/20* (2013.01); *A61F 2007/0261* (2013.01)

(58) Field of Classification Search
CPC ........ A61K 47/20; A61K 47/16; A61K 47/14
USPC .................................................. 514/534, 626
See application file for complete search history.

(56) References Cited

U.S. PATENT DOCUMENTS

| 5,602,183 A | 2/1997 | Martin et al. |
| 5,648,380 A | 7/1997 | Martin |
| 5,874,479 A | 2/1999 | Martin |

(Continued)

FOREIGN PATENT DOCUMENTS

| GB | 2008946 | 6/1979 |
| WO | WO 96/33706 | 10/1996 |

(Continued)

OTHER PUBLICATIONS

Teixeira, et al.; "Local anesthetic-induced microscopic and mesoscopic effects in micelles. A fluorescence, spin label and SAXS"; 2001Biochimica et Biophysica; ACTA 1510 (2001) pp. 93-105.

*Primary Examiner* — Raymond Henley, III
(74) *Attorney, Agent, or Firm* — Thrope North & Western LLP

(57) ABSTRACT

The present disclosure is drawn to topical formulations, transdermal systems, and related methods. In one embodiment, a topical formulation is provided that includes a local anesthetic, a first compound, and a second compound. The first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate.

127 Claims, 6 Drawing Sheets

(56) References Cited

U.S. PATENT DOCUMENTS

| | | |
|---|---|---|
| 6,328,979 B1 | 12/2001 | Yamashita et al. |
| 7,001,592 B1 | 2/2006 | Traynor et al. |
| 7,795,309 B2 | 9/2010 | Kisak et al. |
| 8,343,962 B2 | 1/2013 | Kisak et al. |
| 8,513,304 B2 | 8/2013 | Kisak et al. |
| 8,535,692 B2 | 9/2013 | Pongpeerapat et al. |
| 2002/0006435 A1 | 1/2002 | Samuels et al. |
| 2002/0064524 A1 | 5/2002 | Cevc |
| 2005/0014823 A1 | 1/2005 | Soderlund et al. |
| 2005/0075407 A1 | 4/2005 | Tamarkin et al. |
| 2005/0196354 A1 | 9/2005 | Soshinsky |
| 2006/0229364 A1 | 10/2006 | Hobbs et al. |
| 2008/0075793 A1 | 3/2008 | Dunshee et al. |
| 2011/0028460 A1 | 2/2011 | Kisak et al. |
| 2013/0079371 A1 | 3/2013 | Sundberg et al. |
| 2013/0079404 A1 | 3/2013 | Kisak et al. |
| 2013/0165504 A1 | 6/2013 | Bancel et al. |
| 2013/0259924 A1 | 10/2013 | Bancel et al. |

FOREIGN PATENT DOCUMENTS

| | | |
|---|---|---|
| WO | WO 2005/009510 | 2/2005 |
| WO | WO 2005/018530 | 3/2005 |
| WO | WO 2013/106496 | 7/2013 |

TOPICAL FORMULATIONS, SYSTEMS AND METHODS

This application is a continuation-in-part of U.S. patent application Ser. No. 13/680,623 filed Nov. 19, 2012 and issued as U.S. Pat. No. 8,513,304, which was a continuation application of U.S. patent application Ser. No. 12/848,792 filed Aug. 2, 2010 and issued as U.S. Pat. No. 8,343,962, which was a continuation-in-part of U.S. patent application Ser. No. 12/281,561 filed Jan. 12, 2009 and issued as U.S. Pat. No. 7,795,309, which was a national stage of PCT/IB2007/001983 filed on Mar. 6, 2007, which claimed priority to U.S. Provisional Application Ser. No. 60/778,847, each of the above patent applications and patents being incorporated herein by reference.

BACKGROUND

Topical formulations for application to the skin can be useful in cosmetic applications, for treating conditions of the upper skin layers, and for transdermal administration of active agents to the local tissue underlying the skin or into the blood for systemic distribution. Use of a topical formulation of, for instance, a pharmaceutical agent is advantageous in that it avoids first-pass metabolism, circumvents gastrointestinal ("GI") absorption, can allow delivery of an active ingredient with a relatively short biological half-life, and/or a narrow therapeutic window and facilitates uniform plasma dosing of the active ingredient, and/or can improve user compliance.

In spite of the advantages, transdermal administration is usually limited to about a dozen small lipophilic drugs, available in transdermal patch format (including scopolamine, fentanyl, estradiol, nitroglycerine, nicotine, and testosterone). Skin has evolved to impede the flux of exogenous molecules so as to provide a strong barrier to molecular delivery, particularly agents such as pharmaceutical agents. Transdermal drug administration is difficult since skin is an excellent diffusion barrier.

Structurally, the skin consists of two principle parts: (i) a relatively thin outermost layer (the "epidermis"), and (ii) a thicker inner region (the "dermis"). The outermost layer of the epidermis (the "stratum corneum") consists of flattened dead cells which are filled with keratin. The region between the flattened dead cells of the stratum corneum is filled with lipids which form lamellar phases. The highly impermeable nature of skin is due primarily to the stratum corneum. The viable epidermis underlying the stratum corneum is akin to other living tissue. The dermis provides the skin's structural strength as well as the nerve and vascular networks that support the epidermis.

Delivering an active agent into or through the skin in sufficient concentrations often requires some means for reducing the stratum corneum's hindrance of penetration. A number of methods for lowering the stratum corneum's barrier properties have been developed, including electrically assisted techniques such as iontophoresis or ultrasound, and bypassing the stratum corneum through microneedle arrays or ablation.

Molecular or chemical penetration enhancers provide an effective and inexpensive means of temporarily reducing skin resistance to the passage of actives and other molecules. Molecular penetration enhancers or MPE™s can enhance the diffusion of molecules across the skin by, for example, disrupting the lipid bilayers of the stratum corneum.

Over 300 substances have been identified as MPE™s but surprisingly few have been successfully developed into commercial formulations. Many potent MPE™s are irritating to the cells of the epidermis which can limit both the choice and concentration of MPE™s suitable for topical formulations. Discovery of new MPE™s to increase skin permeability is highly desirable and has been an area of high activity over the last 30 years. However, the number of substances identified to be penetration enhancers is still small relative to the more than 25,000,000 substances identified in the CAS registry (Chemical Abstracts Service, Columbus, Ohio, www.cas.org).

SUMMARY

With this background in mind, the present disclosure is drawn to topical formulations, transdermal systems, and related methods. In one embodiment, a topical formulation is provided that includes a local anesthetic, a first compound, and a second compound. The first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate.

In another embodiment of the present invention, a system for transdermal delivery of a local anesthetic is provided that includes the topical formulation as described herein and a heating component capable of heating the skin surface to a temperature of 35° C. to 47° C.

In another embodiment, a method of treating or preventing pain can include applying system for delivering a local anesthetic to a skin surface of a subject experiencing pain. The system can comprise a heating component capable of heating the skin surface to a temperature of 35° C. to 47° C., as well as the topical formulation described herein. The method can further include maintaining the topical formulation on the skin surface of the subject for a period of time of at least 15 minutes such that the topical formulation is in contact with the skin surface and the heating component is activated to apply the temperature to the topical formulation and/or the skin surface, such as at the site where the topical formulation is in contact with the skin surface.

In still another embodiment, a method of improving the physical stability of topical formulation containing a local anesthetic base and water is provided. The method includes admixing a first compound and a second compound with the local anesthetic base and the water. The first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate.

BRIEF DESCRIPTION OF THE DRAWINGS

Reference will now be made to the exemplary embodiments illustrated, and specific language will be used herein to describe the same. It will nevertheless be understood that no limitation of the scope of the invention is thereby intended.

DETAILED DESCRIPTION

Figure 1:
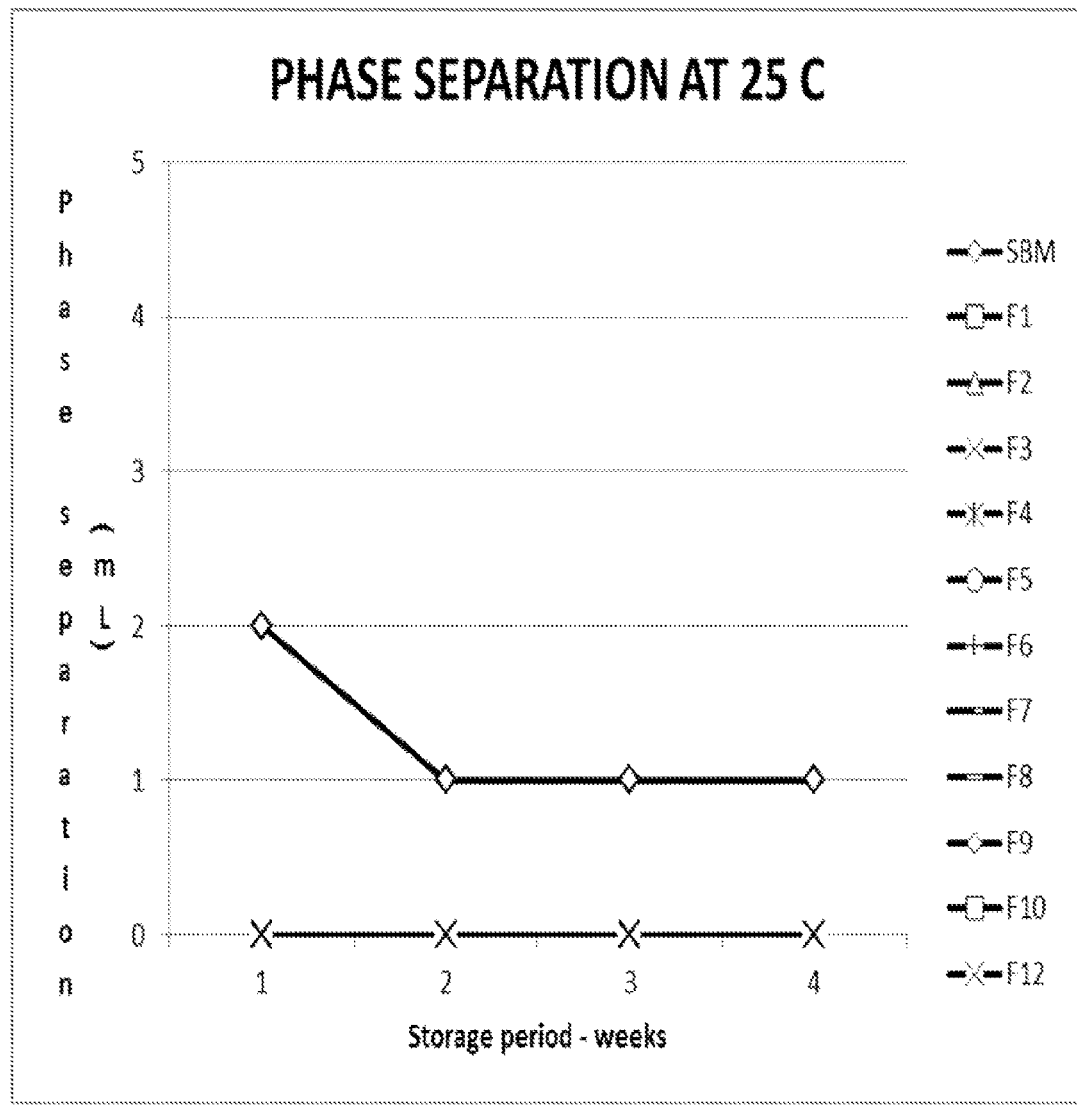
FIG. 1 is a plot of the physical stability (phase separation) at 25° C. of several exemplary embodiments of formulations of the invention disclosed herein.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a local anesthetic" includes reference to one or more of such anesthetics.

"Skin" is defined to include human skin (intact, diseased, ulcerous, or broken) as well as mucosal surfaces that are usually at least partially exposed to air such as lips, genital and anal mucosa, and nasal and oral mucosa.

The local anesthetic formulations and systems disclosed herein can be used both as anesthetics as well as analgesics. It is understood that "anesthesia," refers to preventing pain before it happens, such as preventing a pain caused by needle stick. A formulation used for analgesic purposes or to provide "analgesia" refers to the formulations ability to reduce or eliminate an existing pain, e.g., musculoskeletal pain; muscle pain; back pain; nerve entrapment pain; neuroma pain; headache associated with neuralgia such as occipital neuralgia or trigeminal neuralgia; connective tissue pain such as iliotibial band pain, blood vessel pain, tendinopathy pain, medial tibial stress syndrome pain, bursitis, etc.; arthritis pain such as osteoarthritis pain or rheumatoid arthritis pain; pain associated with injury such as fracture, severance, break, sprain, strain, tear, point pain (e.g., trigger point pain or hit point pain), focal pain, or bruise; or combinations of these pains.

The terms "controlled heating" and "controlled heat" are defined as heat application that is capable of heating a skin surface or a drug formulation (and typically both) to predetermined narrow temperature range for a predetermined duration. A controlled heating device that can be used in accordance with systems and methods of the present disclosure can be configured to generate heat (typically relatively promptly) when activated. Controlled heating can be achieved through special design of the heating component. For example, controlled heating can be achieved through the use of a properly configured heating element(s) including an exothermic chemical composition. Considerations in generating controlled heat with an exothermic heating component can include using proper ratios and exothermic chemical compositions, as well as physical constraints put on the exothermic chemical compositions, e.g., limiting air flow or oxygen contact, spatial configuration of individual heating elements, conductivity of materials used with the exothermic chemical composition, etc. In one embodiment, the heating component can provide heat at a temperature greater than body temperature, but less than a temperature that would cause irreversible skin damage, e.g., burn the skin. An exemplary temperature range that can be implemented for use can be from about 35° C. to about 47° C. In one embodiment, another temperature range can be from about 36° C. to about 44° C. or from about 36° C. to about 42° C. Other desired temperature ranges include from about 38° C. to about 42° C. or from about 36° C. to about 40° C.

As used herein, the term "transdermal" means in the broadest sense through the skin. Further the terms 'transdermal' and 'percutaneous' are used interchangeably throughout this specification.

As used herein the term "topical formulation" refers to a formulation that may be applied to skin or a mucosa. Topical formulations may, for example, be used to confer therapeutic benefit to a patient. Topical formulations can be used for both topical and transdermal administration of substances.

The term "topical administration" is used in its conventional sense to mean delivery of a substance, such as a therapeutically active agent, to the skin or a localized region of the body. Topical administration of a drug may often be advantageously applied during or prior to, for example, a painful medical or cosmetic procedure or to numb or otherwise treat the skin, or to reduce or eliminate an existing pain.

The term "transdermal administration" is used to mean administration through the skin. Transdermal administration is often applied where systemic delivery of an active is desired, although it may also be useful for delivering an active to tissues underlying the skin with minimal systemic absorption (i.e. localized delivery).

As used herein, the term "comparative formulation" is a formulation that is compositionally identical with the exception that amounts (wt %) of the first compound and second compound are each replaced with the same amount (wt %) of water.

The term "penetration enhancer" is used herein to refer to an agent that improves the transport of molecules such as an active agent (e.g., a medicine) into or through the skin. Various conditions may occur at different sites in the body either in the skin or below creating a need to target delivery of compounds. For example, a subject may benefit from delivery of therapeutic drug levels in epidermal tissue to numb the skin prior to, during, or following a painful medical or cosmetic procedure. In a treatment of musculoskeletal pain, delivery of the active agent into deeper underlying tissue may be necessary to achieve therapeutic benefit. In yet other applications, for example in hormone replacement therapy, delivery of drug to the systemic circulation may be an objective. Thus, a "penetration enhancer" may be used to assist in the delivery of an active agent directly to the skin or underlying tissue or indirectly to the site of the disease through systemic distribution. A penetration enhancer may be a pure substance or may comprise a mixture of different chemical entities. In this specification the terms "penetration enhancer," "chemical penetration enhancer," "molecular penetration enhancer," and "MPE™" are used interchangeably.

As used herein the term "multiplexed molecular penetration enhancers" ("MMPE™") means a penetration enhancer comprising two or more substances wherein each of the two or more substances is also penetration enhancer.

As used herein, the term "skin contact region" refers to an area wherein the topical formulation contacts the skin. The skin contact region can have a size, in terms of area that can vary from 2 cm$^2$ to about 200 cm$^2$.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one embodiment, the degree of flexibility can be within about ±10% of the numerical value. In another embodiment, the degree of flexibility can be within about ±5% of the numerical value. In a further embodiment, the degree of flexibility can be within about ±2%, ±1%, or ±0.05%, of the numerical value.

As used herein, a plurality of local anesthetics, compounds, and/or heating mechanisms may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

The present disclosure is drawn various formulations, systems, and methods in the area of transdermal delivery. In one example, formulations, systems, and related methods can be topical formulations for either topical and/or transdermal administration. In one embodiment, a topical formulation is provided that includes a local anesthetic, a first compound, and a second compound. The first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate.

Generally, any local anesthetic known in the art can be incorporated into topical formulations and systems disclosed herein. Non-limiting examples of such local anesthetics include lidocaine, tetracaine, benzocaine, prilocaine, bupivacaine, dimethocaine, mepivacaine, procaine, ropivacaine, trimecaine, articaine, and combinations thereof. In one embodiment, the local anesthetic can be a pharmaceutically acceptable salt of a local anesthetic. In a further embodiment, the local anesthetic can be a pharmaceutically acceptable base of a local anesthetic. In another embodiment, the local anesthetic can include lidocaine, tetracaine, or combinations thereof. In another embodiment, the local anesthetic can include a eutectic mixture of lidocaine and tetracaine.

The local anesthetic can typically comprise from 10 wt % to about 50 wt % of the topical formulations disclosed herein, though concentrations outside of this range can likewise be used. In one embodiment, the local anesthetic can comprise about 20 wt % to about 45 wt % of the topical formulation. In another embodiment, the local anesthetic can comprise about 30 wt % to about 45 wt % topical formulation. In another embodiment, the local anesthetic can comprise at least about 30 wt % of the topical formulation. In a further embodiment the local anesthetic can comprise at least about 35 wt % of the topical formulation. In still a further embodiment, the local anesthetic can comprise about 40 wt % of the topical formulation. For clarity, with respect to these ranges, if a single local anesthetic is used, then that local anesthetic is used to determine the weight percentage. If multiple local anesthetics are present, the total concentration of all local anesthetics present is used to determine the weight percentage.

The topical formulations of the present disclosure can include, as mentioned, first and second compounds. The first and second compounds of the topical formulation can be selected from the group consisting of N-lauroyl sarcosine, sodium octyl sulfate, methyl laurate, isopropyl myristate, oleic acid, glyceryl oleate, and sodium lauryl sulfoacetate. In one embodiment, the first and second compounds can be selected from the group of glyceryl oleate (glycerol monooleate), isopropyl myristate, oleic acid, and sodium lauryl sulfoacetate. In one embodiment, the first compound can be glycerol oleate (glycerol monooleate) and the second compound isopropyl myristate. In another embodiment, the first compound can be glycerol oleate (glycerol monooleate) and the second compound oleic acid. In another embodiment, the first compound can be glycerol oleate (glycerol monooleate) and the second compound sodium lauryl sulfoacetate. In another embodiment, the first compound can be oleic acid and the second compound isopropyl myristate. In a further embodiment, the first compound can be oleic acid and the second compound sodium lauryl sulfoacetate. In still a further embodiment, the first compound can be isopropyl myristate and the second compound can be sodium lauryl sulfoacetate.

The first and second compound can collectively be present in the composition in amounts up to about 50 wt %. More typically, the total concentration of the first compound and the second compound is up to about 40 wt %. Even more preferably, the total concentration of the first compound and the second compound is in the range of from about 1 wt % to about 35 wt %. Even more typically, the total concentration of the first compound and the second compound is in the range of from about 1 wt % to about 30 wt %. Even more typically, the total concentration of the first compound and the second compound is in the range of from about 1 wt % to about 25 wt %. Even more typically, the total concentration of the first compound and the second compound is in the range of from about 1 wt % to about 20 wt %. Even more typically, the total concentration of the first compound and the second compound is in the range of from about 1 wt % to about 15 wt %. Even more typically, the total concentration of the first compound and the second compound is in the range of from about 1 wt % to about 10 wt % per unit volume of the formulation. Even more typically, the total concentration of the first compound and the second compound is in the range of from about 1 wt % to about 7.5 wt %. Even more typically, the total concentration of the first compound and the second compound is in the range of from about 1 wt % to about 5 wt %. Even more typically, the total concentration of the first compound and the second compound is in the range of from about 2 to about 10 wt %.

The first and second compounds can be present in the topical formulation at a weight ratio of first compound to second compound of about 1:9 to about 9:1. In another embodiment, the first and second compounds can be present in the topical formulation at a weight ratio of first compound to second compound of about 1:5 to about 5:1, about 1:4 to about 4:1, about 1:3 to about 3:1, about 1:2 and about 2:1, and about 1:1.

The presence of the first compound and second compound in the formulations can enhance the stability of topical formulations containing local anesthetics. Local anesthetics, particularly local anesthetic bases, are often oily and can separate from aqueous medium when included in topical formulation such as those disclosed and stored for periods of as little as 1-2 weeks at room temperature. Long storage periods can result in increased phase separation in the formulations. One of the surprising benefits of the topical formulations disclosed herein is the improved physical stability of the formulations when stored. For example, in one aspect, the topical formulation can have less phase separation after being stored for four weeks at 25° C. compared to a comparative formulation devoid of the first compound and the second compound (where the first and second compounds are replaced with a commensurate amount of water, i.e. equal weight percentage of water to replace the removed first and second compounds). In another embodiment, the topical formulation can have less phase separation after two weeks when stored at about 40° C. compared to a comparative formulation devoid of the first compound and the second compound. In still another embodiment, the topical formulation can have a phase separation that is at least 10% less, at least 20% less, or at least 30% less after two weeks when stored at about 40° C. compared to a comparative formulation devoid of the first compound and the second compound (again as in each of these examples, replacing the removed first and second compounds with an equivalent amount of water).

In addition to the improvements in physical stability, the topical formulations of the present invention can provide surprising improvements in chemical stability of the local anesthetics contained therein, for example, when the local anesthetic includes a local anesthetic ester such as tetracaine. Local anesthetic esters or ester-type local anesthetics have been known to be susceptible to chemical degradation which can result in reduced concentrations of the local anesthetic and/or increase in certain impurities. For Example, tetracaine is known to degrade via hydrolysis in the presence of water to form certain impurities (the primary hydrolysis product (impurity) being isp-butyl amino benzoic acid (4-BABA)). Tetracaine is a particularly difficult local anesthetic to stabilize long term, especially in aqueous formulations. The presence of the lidocaine in a eutectic mixture can provide some added stability, but it was surprising to discover that certain penetration enhancers provided the added benefit of further stabilizing tetracaine, the local anesthetic ester, even when already admixed with lidocaine as part of a eutectic mixture. In one embodiment, the topical formulations disclosed herein can provide improved chemical stability for local anesthetic esters, such as tetracaine, such that, after being stored for a period of time, e.g., after three weeks, at 25° C. the formulation has a lower concentration of impurities associated with the degradation of the local anesthetic ester as compared to a comparative formulation devoid of the first and second compound (again with an equivalent amount of water added thereto to replace the first and second compounds). In one embodiment, the topical formulations disclosed herein can provide improved stability for tetracaine such that, when the topical formulation includes tetracaine, after three weeks stored at 25° C., the formulation has a lower concentration of 4-BABA compared to a comparative formulation devoid of the first compound and the second compound (again with an equivalent amount of water added thereto to replace the first and second compounds). In another embodiment, when the topical formulation includes tetracaine, the formulation can have a concentration of 4-BABA that is at least 5% lower after 3 weeks stored at 25° C. compared to a comparative formulation devoid of the first compound and the second compound stored under the same conditions for the same amount of time. In a further embodiment, when the topical formulation includes tetracaine, after three weeks stored at 25° C., the formulation has a concentration of 4-BABA that is at least about 10%, at least about 20%, or at least about 30% lower compared to a comparative formulation devoid of the first compound and the second compound stored under the same conditions for the same amount of time. Similar percent reductions described above with respect to 4-BABA can also be achieved for other impurities associated with the degradation of local anesthetic esters, i.e. at least about 10%, at least about 20%, or at least about 30% reductions compared to comparative formulations devoid of first and second compounds.

With the above in mind, there is provided a method of improving the physical and/or chemical stability of a topical formulation containing a local anesthetic including admixing a first compound and a second compound with the local anesthetic. Improvement in chemical stability is generally associated with local anesthetic formulations including local anesthetic esters. In one embodiment, the local anesthetic is a local anesthetic base and the formulation further includes water. In another embodiment, the first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate. By improving the physical stability of topical formulations, manufacturing of compositions that comprise the topical formulation can be simplified. For instance, where the topical formulation is stored prior to incorporation into a transdermal system, e.g. heated patch, no or less mixing (with respect to duration and frequency) of the formulation is required once the formulation has been prepared. Improved physical and chemical stability of topical formulations may also lead to increased commercial shelf life of the system. In one embodiment, the topical formulation of the invention can have an increased shelf life of about 3 months, about 6 months, about 9 months or about 12 months compared to a comparative formulation devoid of the first compound and the second compound stored under the same conditions. In another embodiment the shelf life of the topical formulation can be at least about 27-months, at least about 30 months, at least about 33 months, or at least about 36 months.

In addition to the ability to improve the physical and chemical stability of the local anesthetics in the topical formulations disclosed herein, the first and second compounds present in the topical formulations can function as penetration enhancers for the local anesthetic and/or a second active agent present in the topical formulation. The increased penetration enhancement can also lead to a reduction in the total concentration of skin irritants in a formulation. The compounds acting as excellent penetration enhancers can be used to excellent effect when used in combination, i.e. two (or more) compounds are selected from wherein the first compound and second compound, and each is selected from the group consisting essentially of N-lauroyl sarcosine, sodium octyl sulfate, methyl laurate, isopropyl myristate, oleic acid, glyceryl oleate, and sodium lauryl sulfoacetate. Again and in further detail, examples of combinations of first and second compounds that act as improved penetration enhancers can include: N-lauroyl sarcosine and isopropyl myristate; N-lauroyl sarcosine and oleic acid; sodium octyl sulfate and oleic acid; glyceryl oleate and sodium octyl sulfate; glyceryl oleate and methyl laurate; sodium lauryl sulfoacetate and methyl laurate; or sodium lauryl sulfoacetate and isopropyl myristate.

The topical formulations of the present invention may also be formulated to include other chemical penetration enhancers which have significant ability to enhance transport of the local anesthetics and/or other active agents present in the topical formulations. Such substances may have the character of surfactants, azone-like compounds, solvents, alcohols, fatty acids, fatty esters, aliphatic thiols and the like. Examples of chemical penetration enhancers are reported in the paper of Santus et al. (Santus, C. G. and Baker, R. W., Transdermal enhancer patent literature. Journal of Controlled Release 1993.25:1-20.) The penetration enhancing effect may be measured using techniques known in the art. An example of one measurement method is described in the Examples below.

The topical formulations can also include other components in addition to the local anesthetic and the first and second compounds. Examples of additional compounds that can be included in the topical formulations include water, thickening, gelling and/or solidifying polymers, excipients, fatty acid esters, parabens, solvents, and the like. In one embodiment, the topical formulation can include water, and in some case, the water can be the ingredient that is present in the single greatest concentration. Polymers can also be included, and non-limiting examples of polymers include polyvinyl alcohol, (PVA), Gantrez ES-425 (a monobutyl ester of the copolymer of methyl vinyl ether and maleic anhydride in ethanol), poly(HEMA) or poly(2-hydroxyethyl methacrylate) which consists of a single monomer, 2-hydroxyethyl methacrylate and combinations thereof, Plastoid B (a neutral copolymer based on butyl methacrylate and methyl methacrylate), and Eudragit S100 (anionic copolymer based on methacrylic acid and methyl methacrylate). In one specific embodiment, the topical formulation can include a polyvinyl alcohol. Generally, the polymer can comprise about 5 wt % to about 15 wt % of the formulation. In one embodiment, the polymer can comprise about 6 wt % to about 12 wt %. Non-limiting examples of fatty acid esters that can be present include sorbitan monopalmitate, sorbitan monolaurate, sorbitan monomyristate, sorbitan monooleate, sorbitan monolinoleate and combinations thereof. In one embodiment, the formulation can include sorbitan monopalmitate. The fatty acid ester can comprise about 1 wt % to about 5 wt % of the formulation. Parabens that may be included in the topical formulation include methylparaben, propylparaben, ethylparaben, butylparaben, isobutylparaben, isopropyl paraben, benzyl paraben, and combinations thereof. In one embodiment, the topical formulation can include methylparaben, propyl paraben, or combinations thereof. The paraben can comprise about 0.01 wt % to about 0.6 wt % of the topical formulation. In one embodiment, the paraben can comprise about 0.02 wt % to about 0.5 wt % of the topical formulation.

Other suitable carriers or excipients that may be used in the topical formulations discussed herein are known in the art and include, but are not limited to, solubilizers such as $C_2$ to $C_8$ straight and branched chain alcohols, diols and triols, moisturizers and humectants such as glycerine, amino acids and amino acid derivatives, polyaminoacids and derivatives, pyrrolidone carboxylic acids and their salts and derivatives, surfactants such as sodium laureth sulfate, sorbitan monolaurate, emulsifiers such as cetyl alcohol, stearyl alcohol, thickeners such as methyl cellulose, ethyl cellulose, hydroxymethylcellulose, hydroxypropylcellulose, polyvinylpyrrolidone, polyvinyl alcohol and acrylic polymers. The topical formulation may also include propylene glycol. The propylene glycol may be present in the formulation between about 1% to about 25% w/w. Additionally the topical formulation may also include ethanol and/or polyethylene glycol 300. The ethanol may be present in the formulation between about 1% to about 25% w/w. The polyethylene glycol 300 may be present in the range of between about 1% to about 80% w/w. In addition the topical formulation may include at least one moisturizer/humectant. Other examples of suitable excipients, such as binders and fillers are listed in Remington's Pharmaceutical Sciences, 18th Edition, Ed. Alfonso Gennaro, Mack Publishing Co. Easton, Pa., 1995 and Handbook of Pharmaceutical Excipients, 3rd Edition, Ed. Arthur H. Kibbe, American Pharmaceutical Association, Washington D.C. 2000.

The topical formulations of the present invention may also include one or more skin care actives. "Skin care actives" means all compounds or substances now known or later demonstrated to provide benefit when applied to skin and all compounds now claimed or in the future claimed to provide benefit when applied to skin. Skin care actives may provide benefits, or claimed benefits, in areas such as one or more of wrinkle removal or wrinkle reduction, firming of skin, exfoliation of skin, skin lightening, treatment of dandruff, treatment of acne, skin conditioning, development of tans and artificial tans, improvement of skin moisture content, improvement of skin barrier properties, control of sweat, anti-aging, reduction or avoidance of irritation and reduction or avoidance of inflammation. Examples of skin care actives include molecules such as peptides, proteins, oligonucleotides, fullerenes as well as small molecules. Skin care actives may be protease and/or enzyme inhibitors, anti-coenzymes, chelating agents, antibodies, antimicrobials, humectants, vitamins, skin protectants, antioxidants and/or skin soothing agents, plant extracts and the like. Examples of skin care actives include but are not limited to vitamin C, vitamin E (alpha tocopherol), retinoids, soy derivatives (e.g. isoflavones), green tea polyphenols, alpha hydroxy acids (e.g. glycolic and lactic acids), beta hydroxy acids (e.g. salicylic acid), poly hydroxy acids, alpha lipoic acid, hemp oil (glycerides), niacinamide, dimethyl amino ethanol, coenzyme Q10, kinetin (plant growth hormone), dimethyl sulfone and botulinum toxin. Other examples of skin care actives may be found in The Perricone Prescription by Nicholas Perricone, Harper Collins Publishers Inc., New York, 2002.

The topical formulations of the present invention can be utilized in the manufacture of systems for transdermal delivery of local anesthetics. In one aspect of the present invention, a system for transdermal delivery of a local anesthetic is provided that includes the topical formulation as disclosed herein, and a heating component capable of heating the skin surface to a temperature of 35° C. to 47° C., but more typically from 36° C. to 44° C. or even from 36° C. to 42° C. In one embodiment, the local anesthetic can be present in a topical formulation applied to a skin contact portion of a transdermal patch. The systems can have any general shape or configuration known in the art including, but not limited to, substantially oval, round, square, triangular, or rectangular in shape, to name a few. The system can be such that the topical formulation has a skin contact region (i.e. an area that is configured to contact the skin surface of a subject) having an area of about 2 cm$^2$ to about 200 cm$^2$. In one embodiment, the topical formulation in the system can have a skin contact region having an area of about 7 cm$^2$ to about 150 cm$^2$. In another embodiment, the topical formulation in the system can have a skin contact region having an area of about 2 cm$^2$ to about 12 cm$^2$. In a further embodiment, the topical formulation in the system can have a skin contact region having an area of about 8 cm$^2$ to about 15 cm$^2$. In another embodiment, the system can have a skin contact region having an area of about 15 cm$^2$ to about 25 cm$^2$. In yet another embodiment, the system can have a skin contact region having an area of about 25 cm$^2$ to about 35 cm$^2$. While the skin contact region can have the areas described above, the system as a whole can have an area that contacts the skin that is greater than the skin contact region. In one embodiment, the area that contacts the skin for the system can be from 2 cm$^2$ to about 250 cm$^2$. In another embodiment, the area of the system that contacts the skin can be about 10 cm$^2$ to about 100 cm$^2$. In another embodiment, the area of the system that contacts the skin can be about 30 cm$^2$ to about 100 cm$^2$.

As described, the heating component of the systems can be configured to generate heat to a temperature of 35° C. to 47° C., 36° C. to 45° C., or 36° C. to 42° C. In a particular embodiment, the heating component can be configured to generate a controlled level of heat of 38° C. to 42° C. or from 36° C. to 40° C. The generation of the heat by the heating component can be by any means known in the art. In one embodiment, the heating component can include an exothermic chemical composition.

In one embodiment, the heating component can generate heat by an exothermic oxidative chemical reaction. The chemical-based exothermic oxidation reaction can generate heat through the contact of the oxidative material, e.g. iron, with ambient air. U.S. Pat. No. 6,756,053, which is incorporated herein by reference in its entirety, describes examples of exothermic heating components and devices. The amount of exothermic chemical composition in the heating component can vary from depending on the desired duration of heating and the size of the heating component. It can be beneficial to limit the amount of the exothermic chemical composition in the heating component, as a large amount of exothermic chemical composition can cause the heating component to be excessively large or cumbersome and impractical for use. In one embodiment, the heating device can include no more than 2 grams of an exothermic chemical composition and can be configured to heat an area of skin greater than about 8 cm$^2$. In another embodiment, the heating device can include no more than 4.5 grams of an exothermic chemical composition and can be configured to heat an area of skin greater than about 25 cm$^2$.

In addition to the oxidizable component, the exothermic heating composition can further include activated carbon, salt (such as sodium chloride), and water. In one aspect, a water-retaining substance, such as vermiculite or wood powder, can also be included in the heating component. Depending on the configuration of the heating device, when stored for extended period of time the exothermic heating components can generate gas (believed to be methane and hydrogen) which can cause the packaging in which the exothermic heating component is present to puff up, which in turn can cause complications and problems with respect to storage and transportation. It has been discovered that the inclusion of certain amounts of sulfur-containing compounds, such as elemental sulfur, sulfates, sulfites, sulfides, or thiosulfates, salts, etc., can reduce or eliminate this gas generation problem when included in the packaging.

Water content in the exothermic chemical composition can have an impact on the heating temperature profile of the heating device. The weight ratio of water to the rest of the ingredients in the exothermic heating component can be in the range of about 1:2.6 to about 1:5.0, though this range is not intended to be limiting. In one aspect, the exothermic chemical composition of the heating component can be manufactured in a manner so as to only have access to ambient oxygen through the holes in a cover that can be made of air-impermeable material. In this way, the flow rate of oxygen from ambient air into the exothermic chemical composition, which in turn can be a factor that can affect the amount and rate of heat generated by the heating component and the temperature of the skin surface on which the analgesic system is applied.

Other factors which can influence the temperature and heat generation of the heating component can be the size of the heating component, the amount of the exothermic chemical composition in the heating component, the number and configuration of holes in the heating component's air impermeable cover material, etc.

The exothermic chemical composition can be formulated into a layer having an exothermic material disposed therein. In one embodiment, the system can include an air impermeable layer disposed on an upper surface of the chemical composition layer and can have one or more holes therein. In another embodiment, the system can include an activation tab removably adhered to an upper surface of the air impermeable layer and being configured to cover the one or more holes in the air impermeable layer and inhibit the passage of air through the holes prior to removal of the activation tab. In still another embodiment, the system can include an adhesive layer disposed on a lower surface of one or both of the exothermic chemical composition layer and the lower surface of the air impermeable layer, said adhesive layer being configured to adhere the system to a skin surface.

In addition to being formulated to be included in transdermal systems such as those described above, the topical formulations of the present invention may be formulated by those skilled in the art as liquids, solutions, emulsions, creams, lotions, suspensions, triturates, gels, jellies, foams, pastes, ointments, shampoos, adhesives, other more traditional patches without a heating component, or the like.

The topical formulations and systems disclosed herein can be utilized for the analgesic treatment of pain in a subject, or alternatively, for the anesthesia treatment of the skin prior to a painful medical procedure, e.g., needle stick, incision, skin treatment, or the like.

Thus, in one embodiment, a method of treating or preventing pain can include applying a topical formulation or system for delivering a local anesthetic to a skin surface of a subject experiencing pain. The method can further include maintaining the topical formulation or system can be maintained on the skin surface of the subject for a period of time of at least 15 minutes such that the topical formulation is in contact with the skin surface and the heating component is activated to apply the temperature to the topical formulation and/or the skin surface. The method of treating or preventing pain can be for analgesicly treating existing pain or for anestisizing the skin prior to a painful medical procedure. In one aspect of the method, the heating component can begin heating at about the same time as the system is applied to the skin surface. In another embodiment, formulation can be maintained on the skin surface for a period of time of at least about 20 minutes. In another embodiment, the formulation can be maintained on the skin surface for a period of at least about 60 minutes. In still another embodiment, the system or formulation can be maintained on the skin surface for a period of time of at least about two hours, four hours, six hours, eight hours, 10 hours, 12 hours, 24 hours, etc. In one embodiment, the system can be applied for a period of time and then removed. Pain relief can continue for a period of hours, in some cases days, following the removal of the system from the skin surface.

In one embodiment, the treatment is administered once a day. In another embodiment, the treatment is administered twice a day. In still another embodiment, the treatment is administered three times a day. In yet another embodiment, the treatment is administered four times a day. In a further embodiment, the treatment is administered one to two times a day for one, two, three, four, five, six or seven days. In still a further embodiment, the treatment is administered at least once a day for a longer term such as 1, 2, 3, 4, 5, 6, 7, 8, 9, 10, 11 or 12 weeks. In an even further embodiment, the treatment is administered at least once a day until the condition has ameliorated to where further treatment is not necessary. In another embodiment, the persistence of pain is reduced for a period of time following administration of the topical formulation, for example, days, weeks or months.

In another embodiment, the treatment is administered at least once per week. In another embodiment, the treatment is administered twice per week. In still another embodiment, the treatment is administered three times per week. In yet another embodiment, the treatment is administered four times per week. In yet another embodiment, the treatment is administered five times per week. In yet another embodiment, the treatment is administered six times per week. In a further embodiment, the treatment is administered one to six times per week for one, two, three, four, five, six or seven weeks. In still a further embodiment, the treatment is administered at least once per week for a longer term such as 1, 2, 3, 4, 5, 6, 7, 8, 9, 10, 11 or 12 weeks. In an even further embodiment, the treatment is administered at least once per week until the condition has ameliorated to where further treatment is not necessary.

When not presented and applied to a skin surface in the form of a transdermal delivery system (e.g. patch), the present topical formulation may be applied to the skin by any means known in the art including, but not limited to, by an aerosol, spray, pump-pack, brush, swab, or other applicator. The applicator provides either a fixed or variable metered dose application such as a metered dose aerosol, a stored-energy metered dose pump or a manual metered dose pump. In this example, the topical formulation can be applied to the skin of the human or animal covering a delivery surface area between about 5 and 800 $cm^2$, more preferably between about 7 and 400 $cm^2$, and most preferably about 7 and 200 $cm^2$. The application can be performed by means of a topical metered dose spray combined with an actuator nozzle shroud which together accurately control the amount and/or uniformity of the dose applied. One function of the shroud is to keep the nozzle at a pre-determined height above, and perpendicular to, the skin to which the drug delivery system is being applied. This function may also be achieved by means of a spacer-bar or the like. Another function of the shroud is to enclose the area above the skin in order to prevent or limit bounce-back and/or loss of the drug delivery system to the surrounding environment. The drug delivery system may be a unit volume dispenser with or without a roll-on or other type of applicator. It may also be desirable to apply a number of dosages on untreated skin to obtain the desired result.

While the present invention is directed primarily to the formulations, systems and related methods utilizing local anesthetics as the pharmaceutically active agent (drug), in some aspects, it can be useful or desirable to include alternative or additional pharmaceutically active compositions. Discussion of the various active agents that can be incorporated into the topical formulations, in addition to or instead of the local anesthetics of the present disclosure, is provided below.

In one aspect of the present invention, the at least one active agent is an aryl alkanoic acid, such as an α-aryl alkanoic acid. As is known to a person skilled in the art, α-aryl alkanoic acids are chemical compounds having the general structure of Formula I:

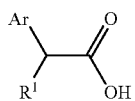

I wherein Ar is an aryl group and $R^1$ is H or an alkyl group, wherein aryl includes aromatic and heteroaromatic groups and alkyl includes acyclic and cyclic alkyl groups. The α-aryl alkanoic acid may be an anti-inflammatory drug such as a non-steroidal anti-inflammatory drug (NSAID) or an analgesic, specific examples of which are listed below. Preferably, the α-aryl alkanoic acids is selected from the group consisting of bromfenac, diclofenac, fenoprofen, flurbiprofen, ibuprofen, indomethacin, ketoprofen, ketorolac, naproxen, sulindac and tolmetin, and pharmaceutically acceptable salts and solvates thereof and mixtures thereof. Structures for these α-aryl alkanoic acids, along with some common trade names, known to a person skilled in the art, are shown in Table 1. More preferably the α-aryl alkanoic acid is selected from the group consisting of diclofenac, ibuprofen and ketoprofen, and pharmaceutically acceptable salts and solvates thereof, and mixtures thereof. Other NSAIDs, that are not α-aryl alkanoic acids, as well as other compounds having antipyretic and analgesic actions are also included in the scope of the present invention. Examples of such compounds include acetaminophen (paracetamol), aspirin, celecoxib, diflunisal, etodolac, etoricoxib, meclofenamic acid, mefenamic acid, meloxicam, nabumetone, oxaprozin, piroxicam, salsalate, and rofecoxib. Structures for these compounds along with some common trade names, known to a person skilled in the art, are shown in Table 2.

In another aspect of the present invention, the at least one active agent is a phenethylamine, for example, a phenethylamine that is an antidepressant, anti-anxiety agent, anticholinergic agent, cholinergic, dopaminergic, stimulant, serotonin antagonist, serotonin inhibitor, anti-emetic, antihistamine and/or antipsychotic, specific examples of which are listed below. As is known to a person skilled in the art, phenethylamines are chemical compounds having the general core structure of Formula II:

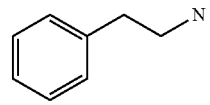

II wherein the phenyl ring, ethylene chain and nitrogen can be substituted. The phenethylamine may be a psychoactive agent that exerts its effect through a monoamine neurotransmitter system, for example dopamine, serotonin and/or norepinephrine receptors. Examples of phenethylamines, include, for example, bupropion, amphetamine, hydroxyamphetamine, dextroamphetamine, methamphetamine, ephedrine, epinephrine, pseudoephedrine, dopamine, epinephryl borate, etafedrine, norepinephrine and oxidopamine, and pharmaceutically acceptable salts and solvates thereof, and mixtures thereof. Preferably the phenethylamine is bupropion, or a pharmaceutically acceptable salt or solvate thereof, such as bupropion hydrochloride. The structure of bupropion, known to a person skilled in the art, is:

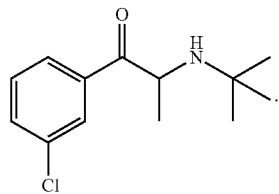 [SMILES: CC(NC(C)(C)C)C(=O)c1cccc(Cl)c1]

In another aspect of the present invention, the at least one active agent is a steroid, for example, steroids that are hormones, glucosteroids, androgens, adrenocortical steroids, anabolics, estrogens and/or progestin, specific examples of which are listed below. As known to a person skilled in the art, steroids are a class of compounds having as a core structure, 4 rings joined as shown in Formula III:

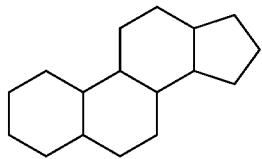

wherein the carbon atoms are optionally substituted. Preferably the steroid is testosterone, or a pharmaceutically acceptable salt or solvate thereof.

Other suitable active agents include those in the class of COX-2 inhibitors such as celecoxib, rofecoxib, valdecoxib, lumiracoxib, etoricoxib; Antifungals such as tolnaftate, econazole, ciclopirox; Antibiotics such as clindamycin; Musculoskeletal agents such as dantrolene; Retinoids such as isotretinoin; Antivirals such as acyclovir; Vasodilating agents such as nitroglycerine, papaverine; Hormones and synthetic substitutes such as androgens, estrogens, insulin; Opiate agonists such as fentanyl, oxycodone, hydromorphone; Local Anaesthetics such as lidocaine, tocainide and mexiletine and butyl-para-aminobenzoate; Anti-inflammatories such as corticosteroids; NMDA receptor antagonists such as ketamine, dextromethorphan and amantadine.

Examples of other therapeutically active agents that may be used include the following: adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; antiasthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; antiinfective; anti-inflammatory; antimicrobial; antimigraine; antimitotic; antimycotic; antinauseant, antineoplastic, antineutropenic, antiparasitic; antiproliferative; antipsychotic; antirheumatic; antiseborrheic; antisecretory; antispasmodic; antithrombotic; antiulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid suppressant; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant, keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic, tranquilizer; amyotrophic lateral sclerosis agent; cerebral ischemia agent; Paget's disease agent; unstable angina agent; vasoconstrictor; vasodilator; wound healing agent; xanthine oxidase inhibitor; and the like.

Specific examples of pharmaceutical agents that may be included within the present topical formulation, both alone or in combination, include but are not limited to:

Adrenergic: Adrenalone; Amidephrine Mesylate; Apraclonidine Hydrochloride; Brimonidine Tartrate; Dapiprazole Hydrochloride; Deterenol Hydrochloride; Dipivefrin; Dopamine Hydrochloride; Ephedrine Sulfate; Epinephrine; Epinephrine Bitartrate; Epinephryl Borate; Esproquin Hydrochloride; Etafedrine Hydrochloride; Hydroxyamphetamine Hydrobromide; Levonordefrin; Mephentermine Sulfate; Metaraminol Bitartrate; Metizoline Hydrochloride; Naphazoline Hydrochloride; Norepinephrine Bitartrate; Oxidopamine; Oxymetazoline Hydrochloride; Phenylephrine Hydrochloride; Phenylpropanolamine Hydrochloride; Phenylpropanolamine Polistirex; Prenalterol Hydrochloride; Propylhexedrine; Pseudoephedrine Hydrochloride; Tetrahydrozoline Hydrochloride; Tramazoline Hydrochloride; and Xylometazoline Hydrochloride.

Adrenocortical steroid: Ciprocinonide; Desoxycorticosterone Acetate; Desoxycorticosterone Pivalate; Dexamethasone Acetate; Fludrocortisone Acetate; Flumoxonide; Hydrocortisone Hemisuccinate; Methylprednisolone Hemisuccinate; Naflocort; Procinonide; Timobesone Acetate; and Tipredane.

Adrenocortical suppressant: Aminoglutethimide; and Trilostane.

Alcohol deterrent: Disulfuram.

Aldosterone antagonist: Canrenoate Potassium; Canrenone; Dicirenone; Mexrenoate Potassium; Prorenoate Potassium; and Spironolactone.

Amino acid: Alanine; Arginine; Aspartic Acid; Carnitine; Cysteine Hydrochloride; Cystine; Glycine; Histidine; Isoleucine; Leucine; Lysine; Lysine Acetate; Lysine Hydrochloride; Methionine; Phenylalanine; Proline; Serine; Threonine; Tryptophan; Tyrosine; and Valine.

Ammonia detoxicant: Arginine Glutamate; and Arginine Hydrochloride.

Amyotrophic lateral sclerosis agents: Riluzole.

Anabolic: Bolandiol Dipropionate; Bolasterone; Boldenone Undecylenate; Bolenol; Bolmantalate; Ethylestrenol; Methenolone Acetate; Methenolone Enanthate; Mibolerone; Nandrolone Cyclotate; Norbolethone; Pizotyline; Quinbolone; Stenbolone Acetate; Tibolone; and Zeranol.

Analeptic: Modafinil.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lornoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zomepirac Sodium; and Zucapsaicin.

Androgen: Fluoxymesterone; Mesterolone; Methyltestosterone; Nandrolone Decanoate; Nandrolone Phenpropionate; Nisterime Acetate; Oxandrolone; Oxymetholone; Silandrone; Stanozolol; Testosterone; Testosterone Cypionate; Testosterone Enanthate; Testosterone Ketolaurate; Testosterone Phenylacetate; Testosterone Propionate; Trestolone Acetate.

Anesthesia (adjunct to): Sodium Oxybate.

Anesthetic: Aliflurane; Benoxinate Hydrochloride; Benzocaine; Biphenamine Hydrochloride; Bupivacaine Hydrochloride; Butamben; Butamben Picrate; Chloroprocaine Hydrochloride; Cocaine; Cocaine Hydrochloride; Cyclopropane; Desflurane; Dexivacaine; Diamocaine Cyclamate; Dibucaine; Dibucaine Hydrochloride; Dyclonine Hydrochloride; Enflurane; Ether; Ethyl Chloride; Etidocaine; Etoxadrol Hydrochloride; Euprocin Hydrochloride; Fluoroxene; Halothane; Isobutamben; Isoflurane; Ketamine Hydrochloride; Levoxadrol Hydrochloride; Lidocaine; Lidocaine Hydrochloride; Mepivacaine Hydrochloride; Methohexital Sodium; Methoxyflurane; Midazolam Hydrochloride; Midazolam Maleate; Minaxolone; Norflurane; Octodrine; Oxethazaine; Phencyclidine Hydrochloride; Pramoxine Hydrochloride; Prilocaine Hydrochloride; Procaine Hydrochloride; Propanidid; Proparacaine Hydrochloride; Propofol; Propoxycaine Hydrochloride; Pyrrocaine; Risocaine; Rodocaine; Roflurane; Salicyl Alcohol; Sevoflurane; Teflurane; Tetracaine; Tetracaine Hydrochloride; Thiamylal; Thiamylal Sodium; Thiopental Sodium; Tiletamine Hydrochloride; and Zolamine Hydrochloride.

Anorectic compound: Dexfenfluramine.

Anorexic agents: Aminorex; Amphecloral; Chlorphentermine Hydrochloride; Clominorex; Clortermine Hydrochloride; Diethylpropion Hydrochloride; Fenfluramine Hydrochloride; Fenisorex; Fludorex; Fluminorex; Levamfetamine Succinate; Mazindol; Mefenorex Hydrochloride; Phemnetrazine Hydrochloride; Phentermine; and Sibutramine Hydrochloride.

Antagonist: Atipamezole; Atosiban; Bosentan; Cimetidine; Cimetidine Hydrochloride; Clentiazem Maleate; Detirelix Acetate; Devazepide; Donetidine; Etintidine Hydrochloride; Famotidine; Fenmetozole Hydrochloride; Flumazenil; Icatibant Acetate; Icotidine; Isradipine; Metiamide; Nadide; Nalmefene; Naloxone Hydrochloride; Naltrexone; Nilvadipine; Oxilorphan; Oxmetidine Hydrochloride; Oxmetidine Mesylate; Quadazocine Mesylate; Ranitidine; Ranitidine Bismuth Citrate; Ranitidine Hydrochloride; Sufotidine; Teludipine Hydrochloride; Tiapamil Hydrochloride; Tiotidine; Vapiprost Hydrochloride; and Zaltidine Hydrochloride.

Anterior pituitary activator: Epimestrol.

Anterior pituitary suppressant: Danazol.

Anthelmintic: Albendazole; Anthelmycin; Bromoxanide; Bunamidine Hydrochloride; Butonate; Cambendazole; Carbantel Lauryl Sulfate; Clioxanide; Closantel; Cyclobendazole; Dichlorvos; Diethylcarbamazine Citrate; Dribendazole; Dymanthine Hydrochloride; Etibendazole; Fenbendazole; Furodazole; Hexylresorcinol; Mebendazole; Morantel Tartrate; Niclosamide; Nitramisole Hydrochloride; Nitrodan; Oxantel Pamoate; Oxfendazole; Oxibendazole; Parbendazole; Piperamide Maleate; piperazine; piperazine Citrate; piperazine Edetate Calcium; Proclonol; Pyrantel Pamoate; Pyrantel Tartrate; Pyrvinium Pamoate; Rafoxanide; Stilbazium Iodide; Tetramisole Hydrochloride; Thiabendazole; Ticarbodine; Tioxidazole; Triclofenol piperazine; Vincofos; and Zilantel.

Anti-acne: Adapalene; Erythromycin, Salnacedin; and Inocoterone Acetate.

Anti-adrenergic: Acebutolol; Alprenolol Hydrochloride; Atenolol; Bretylium Tosylate; Bunolol Hydrochloride; Carteolol Hydrochloride; Celiprolol Hydrochloride; Cetamolol Hydrochloride; Cicloprolol Hydrochloride; Dexpropranolol Hydrochloride; Diacetolol Hydrochloride; Dihydroergotamine Mesylate; Dilevalol Hydrochloride; Esmolol Hydrochloride; Exaprolol Hydrochloride; Fenspiride Hydrochloride; Flestolol Sulfate; Labetalol Hydrochloride; Levobetaxolol Hydrochloride; Levobunolol Hydrochloride; Metalol Hydrochloride; Metoprolol; Metoprolol Tartrate; Nadolol; Pamatolol Sulfate; Penbutolol Sulfate; Phentolamine Mesylate; Practolol; Propranolol Hydrochloride; Proroxan Hydrochloride; Solypertine Tartrate; Sotalol Hydrochloride; Timolol; Timolol Maleate; Tiprenolol Hydrochloride; Tolamolol; and Zolertine Hydrochloride.

Anti-allergic: Amlexanox; Astemizole; Azelastine Hydrochloride; Eclazolast; Minocromil Nedocromil Nedocromil Calcium; Nedocromil Sodium; Nivimedone Sodium; Pemirolast Potassium Pentigetide; Pirquinozol; Poisonoak Extract; Probicromil Calcium; Proxicromil; Repirinast; Tetrazolast Meglumine; Thiazinamium Chloride; Tiacrilast; Tiacrilast Sodium; Tiprinast Meglumine; and Tixanox.

Anti-amebic: Berythromycin; Bialamicol Hydrochloride; Chloroquine; Chloroquine Hydrochloride; Chloroquine Phosphate; Clamoxyquin Hydrochloride; Clioquinol; Emetine Hydrochloride; Iodoquinol; Paromomycin Sulfate; Quinfamide; Symetine Hydrochloride; Teclozan; Tetracycline; and Tetracycline Hydrochloride.

Anti-androgen: Benorterone; Cioteronel; Cyproterone Acetate; Delmadinone Acetate; Oxendolone; Topterone; and Zanoterone.

Anti-anemic: Epoetin Alfa; Epoetin Beta; Ferrous Sulfate, Dried; and Leucovorin Calcium.

Anti-anginal: Amlodipine Besylate; Amlodipine Maleate; Betaxolol Hydrochloride; Bevantolol Hydrochloride; Butoprozine Hydrochloride; Carvedilol; Cinepazet Maleate; Metoprolol Succinate; Molsidomine; Monatepil Maleate; Primidolol; Ranolazine Hydrochloride; Tosifen; and Verapamil Hydrochloride.

Anti-anxiety agent: Adatanserin Hydrochloride; Alpidem; Binospirone Mesylate; Bretazenil; Glemanserin; Ipsapirone Hydrochloride; Mirisetron Maleate; Ocinaplon; Ondansetron Hydrochloride; Panadiplon; Pancopride; Pazinaclone; Serazapine Hydrochloride; Tandospirone Citrate; and Zalospirone Hydrochloride.

Anti-arthritic: Lodelaben.

Anti-asthmatic: Ablukast; Ablukast Sodium; Bunaprolast; Cinalukast; Cromitrile Sodium; Cromolyn Sodium; Enofelast; Isamoxole; Ketotifen Fumarate; Levcromakalim; Lodoxamide Ethyl; Lodoxamide Tromethamine; Montelukast Sodium; Ontazolast; Oxarbazole; Oxatomide; Piriprost; Piriprost Potassium; Pirolate; Pobilukast Edamine; Quazolast; Ritolukast; Sulukast; Tiaramide Hydrochloride; Tibenelast Sodium; Tomelukast; Tranilast; Verlukast; and Verofylline Zarirlukast.

Anti-atherosclerotic: Mifobate; and Timefuronc.

Antibacterial: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylate sodium; Aminosalicylic acid; Amoxicillin; Amphomycin; Ampicillin; Ampicillin Sodium; Apalcillin Sodium; Apramycin; Aspartocin; Astromicin Sulfate; A vilamycin; A voparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Betamicin Sulfate; Biapenem; Biniramycin; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftiroxime Pivoxetil; Ceftizoxime Sodium; Ceftriaxone Sodium; Cefuroxime; Cefuroxime Axetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isepamicin; Isoconazole; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifarthiazole; Nifuradene; Nifuraldezone; Nifuratel; Nifuratrone; Nifurdazil; Nifurimide; Nifurpirinol; Nifurquinazol; Nitrocycline; Nitrofurantoin; Nitromide; Norfloxacin; Novobiocin Sodium; Ofloxacin; Onnetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

Anti-cancer supplementary potentiating age Amitryptyline; Amoxapine; Amphotericin B; Antiarrhythmic drugs (e.g., Quinidine); Antihypertensive drugs (e.g., Reserpine); Ca++ antagonists (e.g., Verapamil; Calmodulin inhibitors (e.g., Prenylamine; Caroverine); Citalopram); Clomipramine; Clomipramine); Desipramine; Doxepin; Maprotiline); Nifedipine; Nitrendipine; Non-tricyclic anti-depressant drugs (e.g., Sertraline; Nortriptyline; Protriptyline; Sulfoximine) and Multiple Drug Resistance reducing agents such as Cremaphor EL; Thiol depleters (e.g., Buthionine; Trazodone; Tricyclic anti-depressant drugs (e.g., Imipramine; Trifluoroperazine; Trimipramine; and Triparanol analogues (e.g., Tamoxifen).

Anticholelithic: Monoctanoin.

Anticholelithogenic: Chenodiol; Ursodiol.

Anticholinergic: Alverinc Citrate; Anisotropine Methylbromide; Atropine; Atropine Oxide Hydrochloride; Atropine Sulfate; Belladonna; Benapryzine Hydrochloride; Benzetimide Hydrochloride; Benzilonium Bromide; Biperiden; Biperiden Hydrochloride; Biperiden Lactate; Clidinium Bromide; Cyclopentolate Hydrochloride; Dexetimide; Dicyclomine Hydrochloride; Dihexyverine Hydrochloride; Domazoline Fumarate; Elantrine; Elucaine; Ethybenztropine; Eucatropine Hydrochloride; Glycopyrrolate; Heteronium Bromide; Homatropine Hydrobromide; Homatropine Methylbromide; Hyoscyamine; Hyoscyamine Hydrobromide; Hyoscyamine Sulfate; Isopropamide Iodide; Mepenzolate Bromide; Methylatropine Nitrate; Metoquizine; Oxybutynin Chloride; Parapenzolate Bromide; Pentapiperium Methylsulfate; Phencarbamide; Poldine Methylsulfate; Proglumide; Propantheline Bromide; Propenzolate Hydrochloride; Scopolamine Hydrobromide; Tematropium Methylsulfate; Tiquinamide Hydrochloride; Tofenacin Hydrochloride; Toquizine; Triampyzine Sulfate; Trihexyphenidyl Hydrochloride; and Tropicamide.

Anticoagulant: Ancrod; Ardeparin Sodium; Bivalirudin; Bromindione; Dalteparin Sodium Desirudin; Dicumarol; Lyapolate Sodium; Nafamostat Mesylate; Phenprocoumon; Tinzaparin Sodium; and Warfarin Sodium.

Anticoccidal: Maduramicin.

Anticonvulsant: Albutoin; Ameltolide; Atolide; Buramate; Cinromide; Citenamide; Clonazepam; Cyheptamide; Dezinamide; Dimethadione; Divalproex Sodium; Eterobarb; Ethosuximide; Ethotoin; Flurazepam Hydrochloride; Fluzinamide; Fosphenyloin Sodium; Gabapentin; Ilepcimide; Lamotrigine; Magnesium Sulfate; Mephenyloin; Mephobarbital; Methetoin; Methsuximide; Milacemide Hydrochloride; Nabazenil; Nafimidone Hydrochloride; Nitrazepam; Phenacemide; Phenobarbital; Phenobarbital Sodium; Phensuximide; Phenyloin; Phenyloin Sodium; Primidone; Progabide; Ralitoline; Remacemide Hydrochloride; Ropizine; Sabeluzole; Stiripentol; Sulthiame; Topiramate; Trimethadione; Valproate Sodium; Valproic Acid; Vigabatrin; Zoniclezole Hydrochloride; and Zonisamide.

Antidepressant: Adinazolam; Adinazolam Mesylate; Alaproclate; Aletamine Hydrochloride; Amedalin Hydrochloride; Amitriptyline Hydrochloride; Aptazapine Maleate; Azaloxan Fumarate; Azepindole; Azipramine Hydrochloride; Bipenamol Hydrochloride; Bupropion Hydrochloride; Butriptyline Hydrochloride; Caroxazone; Cartazolate; Ciclazindol; Cidoxepin Hydrochloride; Cilobamine Mesylate; Clodazon Hydrochloride; Clomipramine Hydrochloride; Cotinine Fumarate; Cyclindole; Cypenamine Hydrochloride; Cyprolidol Hydrochloride; Cyproximide; Daledalin Tosylate; Dapoxetine Hydrochloride; Dazadrol Maleate; Dazepinil Hydrochloride; Desipramine Hydrochloride; Dexamisole; Deximafen; Dibenzepin Hydrochloride; Dioxadrol Hydrochloride; Dothiepin Hydrochloride; Doxepin Hydrochloride; Duloxetine Hydrochloride; Eclanamine Maleate; Encyprate; Etoperidone Hydrochloride; Fantridone Hydrochloride; Fenmetramide; Fezolamine Fumarate; Fluotracen Hydrochloride; Fluoxetine; Fluoxetine Hydrochloride; Fluparoxan Hydrochloride; Gamfexine; Guanoxyfen Sulfate; Imafen Hydrochloride; Imiloxan Hydrochloride; Imipramine Hydrochloride; Indeloxazine Hydrochloride; Intriptyline Hydrochloride; Iprindole; Isocarboxazid; Ketipramine Fumarate; Lofepramine Hydrochloride; Lortalamine; Maprotiline; Maprotiline Hydrochloride; Melitracen Hydrochloride; Minaprine Hydrochloride; Mirtazapine; Moclobemide; Modaline Sulfate; Napactadine Hydrochloride; Napamezole Hydrochloride; Nefazodone Hydrochloride; Nisoxetine; Nitrafudam Hydrochloride; Nomifensine Maleate; Nortriptyline Hydrochloride; Octriptyline Phosphate; Opipramol Hydrochloride; Oxaprotiline Hydrochloride; Oxypertine; Paroxetine; Phenelzine Sulfate; Pirandamine Hydrochloride; Pridefine Hydrochloride; Prolintane Hydrochloride; Protriptyline Hydrochloride; Quipazine Maleate; Rolicyprine; Seproxetine Hydrochloride; Sertraline Hydrochloride; Sulpiride; Suritozole; Tametraline Hydrochloride; Tampramine Fumarate; Tandamine Hydrochloride; Thiazesim Hydrochloride; Thozalinone; Tomoxetine Hydrochloride; Trazodone Hydrochloride; Trebenzomine Hydrochloride; Trimipramine Maleate; Venlafaxine Hydrochloride; Viloxazine Hydrochloride; Zimeldine Hydrochloride; and Zometapine.

Antidiabetic: Acetohexamide; Buformin; Butoxamine Hydrochloride; Camighbose; Chlorpropamide; Ciglitazone; Englitazone Sodium; Etoformin Hydrochloride; Gliamilide; Glibornuride; Glicetanile Sodium; Gliflumide; Glipizide; Glucagon; Glyburide; Glyhexamide; Glymidine Sodium; Glyoctamide; Glyparamide; Insulin; Insulin Human; Insulin Human Zinc; Insulin Human Zinc, Extended; Insulin Human, Isophane; Insulin Lispro; Insulin Zinc; Insulin Zinc, Extended; Insulin Zinc, Prompt; Insulin, Dalanated; Insulin, Isophane; Insulin, Neutral; Linogliride; Linogliride Fumarate; Metformin; Methyl Palmoxirate; Palmoxirate Sodium; Pioglitazone Hydrochloride; Piroglitide Tartrate; Proinsulin Human; Seglitide Acetate; Tolazamide; Tolbutamide; Tolpyrramide; Troglitazone; and Zopolrestat.

Antidiarrheal: Diphenoxylate Hydrochloride; Methylprednisolone; Metronidazole; and Rolgamidine.

Antidiuretic: Argipressin Tannate; Desmopressin Acetate; and Lypressin.

Antidote: Dimercaprol; Edrophonium Chloride; Fomepizole; Levoleucovorin Calcium; Methylene Blue; and Protamine Sulfate.

Antidyskinetic: Selegiline Hydrochloride.

Anti-emetic: Alosetron Hydrochloride; Batanopride Hydrochloride; Bemesetron; Benzquinamide; Chlorpromazine; Chlorpromazine Hydrochloride; Clebopride; Cyclizine Hydrochloride; Dimenhydrinate; Diphenidol; Diphenidol Hydrochloride; Diphenidol Pamoate; Dolasetron Mesylate; Domperidone; Dronabinol; Flumeridone; Galdansetron Hydrochloride; Granisetron; Granisetron Hydrochloride; Lurosetron Mesylate; Meclizine Hydrochloride; Metoclopramide Hydrochloride; Metopimazine; Prochlorperazine; Prochlorperazine Edisylate; Prochlorperazine Maleate; Promethazine Hydrochloride; Thiethylperazine; Thiethylperazine Malate; Thiethylperazine Maleate; Trimethobenzamide Hydrochloride; and Zacopride Hydrochloride.

Anti-epileptic: Felbamate; Iamotrigine; Loreclezole; and Tolgabide.

Anti-estrogen: Clometherone; Nafoxidine Hydrochloride; Nitromifene Citrate; Raloxifene Hydrochloride; Tamoxifen Citrate; Toremifene Citrate; and Trioxifene Mesylate.

Antifibrinolytic: Nafamostat Mesylate.

Antifungal: Acrisorcin; Ambruticin; Azaconazole; Azaserine; Basifungin; Bifonazole; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Itraconazole; Kalafungin; Ketoconazole; Lomoftmgin; Lydimycin; Mepartricin; Miconazole; Miconazole Nitrate; Monensin; Monensin Sodium; Naftifine Hydrochloride; Nifuratel Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Pyrrolnitrin; Rutamycin; Sanguinarium Chloride; Saperconazole; Selenium Sulfide; Sinefungin; Sulconazole Nitrate; Terbinafine; Terconazole; Thiram; Tioconazole; Tolciclate; Tolindate; Tolnaftate; Triacetin; Triafungin; Undecylenic Acid; Viridofulvin; Zinc Undecylenate; and Zinoconazole Hydrochloride.

Antiglaucoma agent: Alprenoxime Hydrochloride; Colforsin; Dipivefrin Hydrochloride; Naboctate Hydrochloride; Pilocarpine; and Pirnabine.

Antihemorrhagic: Poliglusam.

Antihemorrheologic: Phentoxifylline.

Antihistaminic: Acrivastine; Antazoline Phosphate; Azatadine Maleate; Barmastine; Bromodiphenhydramine Hydrochloride; Brompheniramine Maleate; Carbinoxamine Maleate; Cetirizine Hydrochloride; Chlorpheniramine Maleate; Chlorpheniramine Polistirex; Cirmarizine; Clemastine; Clemastine Fumarate; Closiramine Aceturate; Cycliramine Maleate; Cyclizine; Cyproheptadine Hydrochloride; Dexbrompheniramine Maleate; Dexchlorpheniramine Maleate; Dimethindene Maleate; Diphenhydramine Citrate; Diphenhydramine Hydrochloride; Dorastine Hydrochloride; Doxylamine Succinate; Ebastine; Fexofenadine HCl; Levocabastine Hydrochloride; Loratadine; Mianserin Hydrochloride; Noberastine; Orphenadrine Citrate; Pyrabrom; Pyrilamine Maleate; Pyroxamine Maleate; Rocastine Hydrochloride; Rotoxamine; Tazifylline Hydrochloride; Temelastine; Terfenadine; Tripelennamine Citrate; Tripelennamine Hydrochloride; and Triprolidine Hydrochloride.

Antihyperlipidemic: Cholestyramine Resin; Clofibrate; Colestipol Hydrochloride; Crilvastatin; Dalvastatin; Dextrothyroxine Sodium; Fluvastatin Sodium; Gemfibrozil; Lecimibide; Lovastatin; Niacin; Pravastatin Sodium; Probucol; Simvastatin; Tiqueside; and Xenbucin.

Antihyperlipoproteinemic: Acifran; Beloxamide; Bezafibrate; Boxidine; Cetaben Sodium; Ciprofibrate; Gemcadiol; Halofenate; Lifibrate; Meglutol; Nafenopin; Pimetine Hydrochloride; Theofibrate; Tibric Acid; and Treloxinate.

Antihypertensive: Alfuzosin Hydrochloride; Alipamide; Althiazide; Amiquinsin Hydrochloride; Anaritide Acetate; Atiprosin Maleate; Belfosdil; Bemitradine; Bendacalol Mesylate; Bendroflumethiazide; Benzthiazide; Bethanidine Sulfate; Biclodil Hydrochloride; Bisoprolol; Bisoprolol Fumarate; Bucindolol Hydrochloride; Bupicomide; Buthiazide; Candoxat rilat; Candoxatril; Captopril; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Diltiazem Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancvdine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone Indapamide; Indolapril Hydrochloride; Indoramin; Indoramin Hydrochloride; Indorenate Hydrochloride; Lacidipine; Leniquinsin; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide Methyclothiazide Methyldopa; Methyldopate Hydrochloride; Metipranolol; Metolazone Metoprolol Fumarate; Metyrosine; Minoxidil; Muzolimine; Nebivolol; Nifidipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; and Zofenoprilat Arginine.

Antihypotensive: Ciclafrine Hydrochloride; and Midodrine Hydrochloride.

Anti-infective: Acyclovir; Difloxacin Hydrochloride; Integrase Inhibitors of HIV and other retroviruses; Lauryl Isoquinolinium Bromide; Moxalactam Disodium; Ornidazole; Pentisomicin; Protease inhibitors of HIV and other retroviruses; and Sarafloxacin Hydrochloride.

Anti-infective (topical): Alcohol; Aminacrine Hydrochloride; Benzethonium Chloride; Bithionolate Sodium; Bromchlorenone; Carbamide Peroxide; Cetalkonium Chloride; Cetylpyridinium Chloride; Chlorhexidine Hydrochloride; Domiphen Bromide; Fenticlor; Fludazonium Chloride; Fuchsin, Basic; Furazolidone; Gentian Violet; Halquinols; Hexachlorophene; Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofarazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; and Troclosene Potassium.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anitrazafen; Apazone; Balsalazide Disodium; Bendazac; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Difluprednate; Diftalone; Dimethyl Sulfoxide; Drocinonide; Endrysone; Enlimomab; Enolicam Sodium; Etodolac; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Fluocortin Butyl; Fluorometholone Acetate; Fluquazone; Fluretofen; Fluticasone Propionate; Furaprofen; Furobufen; Halcinonide; Halobetasol Propionate; Halopredone Acetate; Ibuprofen; Ibuprofen Aluminum; Ibuprofen Piconol; Ilonidap; Indomethacin Sodium; Indomethacin; Indoprofen Indoxole; Intrazole; Isoflupredone Acetate; Isoxepac; Isoxicam; Ketoprofen; Lomoxicam; Loteprednol Etabonate; Meclofenamate Sodium; Meclofenamic Acid; Meclorisone Dibutyrate; Mesalamine; Meseclazone; Methylprednisolone Suleptanate; Morniflumate; Nabumetone; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Piroxicam; Piroxicam Cinnamate; Pirprofen; Prednazate; Prednisolone Sodium Phosphate; Prifelone; Prodolic Acid; Proquazone; Rimexolone; Romazarit; Salnacedin; Seclazone; Sermetacin; Sudoxicam; Sulindac; Suprofen; Talniflumate; Tenidap; Tenidap Sodium; Tenoxicam; Tesicam; Tesimide; Tixocortol Pivalate; Tolmetin; Tolmetin Sodium; Triclonide; Triflumidate; and Zidometacin.

Antikeratinizing agent: Doretinel; Linarotene; and Pelretin.

Antimalarial: Amodiaquine Hydrochloride; Amquinate; Artefiene; Chloroquine; Chloroquine Hydrochloride; Cycloguanil Pamoate; Enpiroline Phosphate; Halofantrine Hydrochloride; Hydroxychloroquine Sulfate; Mefloquine Hydrochloride; Menoctone; Primaquine Phosphate; Pyrimethamine; Quinine Sulfate; and Tebuquine.

Antimicrobial: Aztreonam; Chlorhexidine Gluconate; Imidurea; Lycetamine; Nibroxane; Pirazmonam Sodium; Propionic Acid; Pyrithione Sodium; and Tigemonam Dicholine.

Antimigraine: Naratriptan Hydrochloride; Sergolexole Maleate; Sumatriptan Succinate; and Zatosetron Maleate.

Antimitotic: Podofilox.

Antimycotic: Amorolfine.

Antinauseant: Buclizine Hydrochloride; and Cyclizine Lactate.

Antineoplastic: Acivicin; Aclarubicin; Acodazole Hydrochloride; Acronine; Adozelesin; Aldesleukin; Altretamine; Ambomycin; Ametantrone Acetate; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cisplatin; Cladribine; Crisnatol Mesylate; Cyclophosphamide; Cytarabine; Dacarbazine; Dactinomycin; Daunorubicin Hydrochloride; Decitabine; Dexorinaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Gold Au 198; Hydroxyurea; Idarubicin, Hydrochloride; Ifosfamide; Ilmofosine; Interferon Alfa-2a; Interferon Alfa-2b; Interferon Alfan3; Interferon Alfa-n1; Interferon Beta-I a; Interferon Gamma-I b; Iproplatin; Irinotecan Hydrochloride; Isotretinoin; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamvcin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Prednimustine; Procarbazine Hydrochloride; Puromycin; Puromycin Hydrochloride; Pyrazofurin; Riboprine; Rogletimide; Safingol Safingol Hydrochloride; Semustine; Simtrazene; Sparfosate Sodium; Sparsomycin; Spiro germanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofarin; Tirapazamine; Topotecan Hydrochloride; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

Anti-neoplastic compounds (additional): 20-epi-1,25 Dihydroxyvitamin D3; 5-Ethynyluracil; Abiraterone; Acylfulvene; Adecypenol; ALL-TK Antagonists; Ambamustine; Amidox; Amifostine; Aminolevulinic Acid; Amrubicin; Anagrelide; Andrographolide; Angiogenesis Inhibitors; Antagonist D; Antagonist G; Antarelix; Antiandrogen, Prostatic Carcinoma; Anti-Dorsalizing Morphogenetic Protein-I; Antiestrogen; Antineoplaston; Antisense Oligonucleotides; Aphidicolin Glycinate; Apoptosis Gene Modulators; Apoptosis Regulators; Apurinic Acid; Ara-CDP-DL-PTBA; Arginine Deaminase; Asulacrine; Atamestane; Atrimustine; Axinastatin 1; Axinastatin 2; Axinastatin 3; Azasetron; Azatoxin; Azatyrosine; Baccatin III Derivatives; Balanol; BCR/ABL Antagonists; Benzochlorins; Benzoylstaurosporine; Beta Lactam Derivatives; Beta-Alethine; Betaclamycin B; Betulinic Acid; bFGF Inhibitor; Bisantrene; Bisaziridinylspermine; Bisnafide; Bistratene A; Breflate; Budotitane; Buthionine Sulfoximine; Calcipotriol; Calphostin C; Camptothecin Derivatives; Canarypox IL-2; Capecitabine; Carboxamide-Amino-Triazole; Carboxyamidotriazole; CaRest MI; CARN 700, Cartilage Derived Inhibitor; Casein Kinase Inhibitors (ICOS); Castanospermine; Cecropin B; Cetrorelix; Chlorins; Chloroquinoxaline Sulfonamide; Cicaprost; Cis-Porphyrin; Clomifene analogues; Collismycin A; Collismycin B; Combretastatin A4; Combretastatin Analogue; Conagenin; Crambescidin 816; Crisnatol; Cryptophycin 8; Cryptophycin A Derivatives; Curacin A; Cyclopentanthraquinones; Cycloplatam; Cypemycin; Cytarabine Ocfosfate; Cytolytic Factor; Cytostatin; Dacliximab; Dehydrodidenmin B; Dexifosfamide; Dexverapamil; Didemnin B; Didox; Diethylnorspennine; Dihydro Azacytidine; 9-Dihydrotaxol; Dioxamycin; Diphenyl Spiromustine; Docosanol; Dolasetron; Doxifluridine; Duocarmycin SA; Ebselen; Ecomustine; Edelfosine; Edrecolomab; Eflomithine; Elemene; Emitefur; Epirubicin; Estramustine Analogue; Estrogen Agonists; Estrogen Antagonists; Exemestane; Fadrozole; Fiezelastine; Flavopiridol; Fluasterone; Fludarabine; Fluorodaunorunicin Hydrochloride; Forfenimex; Formestane; Fostriecin; Fotemustine; Gadolinium Texaphyrin; Gallium Nitrate; Galocitabine; Ganirelix; Gelatinase Inhibitors; Glutathione Inhibitors; Hepsulfam; Heregulin; Hexamethylene Bisacetamide; Hypericin; Ibandronic acid; Idarubicin; Idoxifene; Idramantone; Ilomastat; Imidazoacridones; Immunostimulant Peptides; Insulin-Like Growth Factor-1 Receptor Inhibitor; Interferon Agonists; Interferons; Interleukins; Iobenguane; Iododoxorubicin; 4-Ipomeanol; Irinotecan; Iroplact; Irsogladine; Isobengazole; Isohomohalicondrin B; Itasetron; Jasplakinolide; Kahalalide F; Lamellarin-N Triacetate; Lanreotide; Leinamycin; Lentinan Sulfate; Leptolstatin; Leukemia Inhibiting Factor; Leukocyte Alpha Interferon; Leuprolide+Estrogen+Progesterone; Leuprorelin; Levamisole; Liarozole; Linear Polyamine Analogue; Lipophilic Disaccharide Peptide; Lipophilic Platinum Compounds; Lissoclinamide 7; Lobaplatin; Lombricine; Lometrexol; Lonidamine; Losoxantrone; Lurtotecan; Lutetium Texaphyrin; Lysofylline; Lytic Peptides; Maitansine; Mannostatin A; Marimastat; Maspin; Matrilysin Inhibitors; Matrix Metalloproteinase Inhibitors; Merbarone; Meterelin; Methioninase; Metoclopramide; MIF Inhibitor; Mifepristone; Miltefosine; Mirimostim; Mismatched Double Stranded RNA; Mitoguazone; Mitolactol; Mitomycin analogues; Mitonafide; Mitotoxin Fibroblast Growth Factor-Saporin; Mitoxantrone; Mofarotene; Monoclonal Antibody, Human Chorionic Gonadotrophin; Monophosphoryl Lipid A+Myobacterium Cell Wall Sk; Mopidamol; Multiple Drug Resistance Gene Inhibitor; Multiple Tumor Suppressor I-Based Therapy; Mustard Anticancer Agent; Mycaperoxide B; Mycobacterial Cell Wall Extract; Myriaporone; NAcetyldinaline; Nafarelin; Nagrestip; Naloxone+Pentazocine; Napavin; Naphterpin; Nartograstim; Nedaplatin; Nemorubicin; Neridronic Acid; Neutral Endopeptidase; Nilutamide; Nisamycin; Nitric Oxide Modulators; Nitroxide Antioxidant; Nitrullyn; N-Substituted Benzamides; 06-Benzylguanine; Okicenone; Oligonucleotides; Onapristone; Ondansetron; Oracin; Oral Cytokine Inducer; Osaterone; Oxaliplatin; Oxaunomycin; Paclitaxel Analogues; Paclitaxel Derivatives; Palauamine; Palmitoylrhizoxin; Pamidronic Acid; Panaxytriol; Panomifene; Parabactin; Pazelliptine; Peldesine; Pentostatin; Pentrozole; Perflubron; Perillyl Alcohol; Phenazinomycin; Phenylacetate; Phosphatase Inhibitors; Picibanil; Pilocarpine Hydrochloride; Pirarubicin; Piritrexim; Placetin A; Placetin B; Plasminogen Activator Inhibitor; Platinum Complex; Platinum Compounds; Platinum-Triamine Complex; Propyl Bis-Acridone; Prostaglandin J2; Proteasome Inhibitors; Protein A-Based Immune Modulator; Protein Kinase C Inhibitor; Protein Kinase C Inhibitors, Microalgal; Protein Tyrosine Phosphatase Inhibitors; Purine Nucleoside Phosphorylase Inhibitors; Purpurins; Pyrazoloacridine; Pyridoxylated Hemoglobin Polyoxyethylene Conjugate; Raf Antagonists; Raltitrexed; Ramosetron; Ras Farnesyl Protein Transferase Inhibitors; Ras Inhibitors; Ras-GAP Inhibitor; Retelliptine Demethylated; Rhenium, Re 186 Etidronate; Rhizoxin; Ribozymes; RII Retinamide; Rohitukine; Romurtide; Roquinimex; Rubiginone B 1; Ruboxyl; Safingol; Saintopin; SarCNU; Sarcophytol A; Sdi 1 Mimetics; Senescence Derived Inhibitor 1; Sense Oligonucleotides; Signal Transduction Inhibitors; Signal Transduction Modulators; Single Chain Antigen Binding Protein; Sizofiran; Sobuzoxane; Sodium Borocaptate; Sodium Phenylacetate; Solverol; Somatomedin Binding Protein; Sonermin; Sparfosic Acid; Spicamycin D; Splenopentin; Spongistatin 1; Squalamine; Stem Cell Inhibitor; Stem-Cell Division Inhibitors; Stipiamide; Stromelysin Inhibitors; Sulfinosine; Superactive Vasoactive Intestinal Peptide Antagonist; Suradista; Suramin; Swainsonine; Synthetic Glycosaminoglycans; Tallimustine; Tamoxifen Methiodide; Tauromustine; Tellurapyrylium; Telomerase Inhibitors; Temozolomide; Tetrachlorodecaoxide; Tetrazomine; Thaliblastine; Thalidomide; Thiocoraline; Thrombopoietin; Thrombopoietin Mimetic; Thymalfasin; Thymopoietin Receptor Agonist; Thymotrinan; Thyroid Stimulating Hormone; Tin Ethyl Etiopurpurin; Titanocene Dichloride; Topotecan; Topsentin; Toremifene; Totipotent Stem Cell Factor; Translation Inhibitors; Triacetyluridine; Triciribine; Tropisetron; Turosteride; Tyrosine Kinase Inhibitors; Tyrphostins; UBC Inhibitors; Ubenimex; Urogenital Sinus-Derived Growth Inhibitory Factor; Urokinase Receptor Antagonists; Variolin B; Vector system, Erythrocyte Gene Therapy; Velaresol; Veramine; Verdins; Vinorelbine; Vinxaltine; Vitaxin; Zilascorb; and Zinostatin Stimalamer.

Antineutropenic: Filgrastim; Lenograstim; Molgramostim; Regramostim; and Sargramostim.

Antiobsessional agent: Fluvoxamine Maleate.

Antiparasitic: Abamectin; Clorsulon; and Ivermectin.

Antiparkinsonian: Benztropine Mesylate; Biperiden; Biperiden Hydrochloride; Biperiden Lactate; Carbidopa-Levodopa; Carmantadine; Ciladopa Hydrochloride; Dopamantine; Ethopropazine Hydrochloride; Lazabemide; Levodopa; Lometraline Hydrochloride; Mofegiline Hydrochloride; N axagolide Hydrochloride; Pareptide Sulfate; Procyclidine Hydrochloride; Ropinirole Hydrochloride; and Tolcapone.

Antiperistaltic: Difenoximide Hydrochloride; Difenoxin; Fluperamide; Lidamidine Hydrochloride; Loperamide Hydrochloride; Malethamer; Nufenoxole; Paregoric.

Antipneumocystic: Atovaquone.

Antiproliferative agent: Piritrexim Isethionate.

Antiprostatic hypertrophy: Sitogluside.

Antiprotozoal: Amodiaquine; Azanidazole; Banmidazole; Camidazole; Chlortetracycline Bisulfate Chlortetracycline Hydrochloride; Flubendazole; Flunidazole; Halofuginone Hydrobromide; Imidocarb Hydrochloride; Ipronidazole; Misonidazole; Moxnidazole; Nitarsone; Ronidazole; Sulnidazole; and Tinidazole.

Antipruritic: Methdilazine; Methdilazine Hydrochloride; and Trimeprazine Tartrate.

Antipsoriatic: Acitretin; Anthralin; Azaribine; Calcipotriene; Cycloheximide; Enazadrem Phosphate; Etretinate; Liarozole Fumarate; Lonapalene; and Tepoxalin.

Antipsychotic: Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Promazine Hydrochloride; Remoxipride; Remoxipride Hydrochloride; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

Antirheumatic: Auranofin; Aurothioglucose; Bindarit; Lobenzarit Sodium; Phenylbutazone; Pirazolac; Prinomide Tromethamine; and Seprilose.

Antischistosomal: Becanthone Hydrochloride; Hycanthone; Lucanthone Hydrochloride; Niridazole; Oxamniquine; Pararosaniline Pamoate; and Teroxalene Hydrochloride.

Antiseborrheic: Chloroxine; Piroctone; Piroctone Olamine; and Resorcinol Monoacetate.

Antisecretory: Arbaprostil; Deprostil; Fenoctimine Sulfate; Octreotide; Octreotide Acetate; Omeprazole Sodium; Rioprostil; Trimoprostil.

Antispasmodic: Stilonium Iodide; Tizanidine Hydrochloride.

Antithrombotic: Anagrelide Hydrochloride; Dalteparin Sodium; Danaparoid Sodium; Dazoxiben Hydrochloride; Efegatran Sulfate; Enoxaparin Sodium; Ifetroban; Ifetroban Sodium; and Trifenagrel.

Antitussive: Benzonatate; Butamirate Citrate; Chlophedianol Hydrochloride; Codeine Polistirex; Codoxime; Dextromethorphan; Dextromethorphan Hydrobromide; Dextromethorphan Polistirex; Ethyl Dibunate; Guaiapate; Hydrocodone Bitartrate; Hydrocodone Polistirex; Levopropoxyphene Napsylate; Noscapine; Pemerid Nitrate; Pipazethate; and Suxemerid Sulfate.

Anti-ulcerative: Aceglutamide Aluminum; Cadexomer Iodine; Cetraxate Hydrochloride; Enisoprost; Isotiquimide; Lansoprazole; Lavoltidine Succinate; Misoprostol; Nizatidine; Nolinium Bromide; Pantoprazole; Pifamine; Pirenzepine Hydrochloride; Rabeprazole Sodium; Remiprostol; Roxatidine Acetate Hydrochloride; Sucralfate; Sucrosofate Potassium; and Tolimidone.

Anti-urolithic: Cysteamine; Cysteamine Hydrochloride; and Tricitrates.

Antiviral: Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Appetite suppressant: Dexfenfluramine Hydrochloride; Phendimetrazine Tartrate; and Phentermine Hydrochloride.

Benign prostatic hyperplasia therapy agent: Tamsulosin Hydrochloride.

Blood glucose regulators: Acetohexamide and Glipizide; Chloropropamide; and Human insulin.

Bone resorption inhibitor: Alendronate Sodium; Etidronate Disodium; and Pamidronate Disodium.

Bronchodilator: Albuterol; Albuterol Sulfate; Azanator Maleate; Bamifylline Hydrochloride; Bitolterol Mesylate; Butaprost; Carbuterol Hydrochloride; Clorprenaline Hydrochloride; Colterol Mesylate; Doxaprost; Doxofylline; Dyphylline; Enprofylline; Ephedrine; Ephedrine Hydrochloride; Fenoterol; Fenprinast Hydrochloride; Guaithylline; Hexoprenaline Sulfate; Hoquizil Hydrochloride; Ipratropium Bromide; Isoetharine; Isoetharine Hydrochloride; Isoetharine Mesylate; Isoproterenol Hydrochloride; Isoproterenol Sulfate; Metaproterenol Polistirex; Metaproterenol Sulfate; Nisbuterol Mesylate; Oxtriphylline; Picumeterol Fumarate; Piquizil Hydrochloride; Pirbuterol Acetate; Pirbuterol Hydrochloride; Procaterol Hydrochloride; Pseudoephedrine Sulfate; Quazodine; Quinterenol Sulfate; Racepinephrine; Racepinephrine Hydrochloride; Reproterol Hydrochloride; Rimiterol Hydrobromide; Salmeterol; Salmeterol Xinafoate; Soterenol Hydrochloride; Sulfonterol Hydrochloride; Suloxifen Oxalate; Terbutaline Sulfate; Theophylline; Xanoxate Sodium; Zindotrine; and Zinterol Hydrochloride.

Carbonic anhydrase inhibitor: Acetazolamide; Acetazolamide Sodium; Dichlorophenamide; Dorzolamide Hydrochloride; Methazolamide; and Sezolamide Hydrochloride.

Cardiac depressant: Acecainide Hydrochloride; Acetylcholine Chloride; Actisomide; Adenosine; Amiodarone; Aprindine; Aprindine Hydrochloride; Artilide Fumarate; Azimilide Dihydrochloride; Bidisomide; Bucainide Maleate; Bucromarone; Capobenate Sodium; Capobenic Acid; Cifenline; Cifenline Succinate; Clofilium Phosphate; Disobutamide; Disopyramide; Disopyramide Phosphate; Dofetilide; Drobuline; Edifolone Acetate; Emilium Tosylate; Encainide Hydrochloride; Flecainide Acetate; Ibutilide Fumarate; Indecainide Hydrochloride; Ipazilide Fumarate; Lorajmine Hydrochloride; Lorcainide Hydrochloride; Meobentine Sulfate; Mexiletine Hydrochloride; Modecainide; Moricizine; Oxiramide; Pirmenol Hydrochloride; Pirolazamide; Pranolium Chloride; Procainamide Hydrochloride; Propafenone Hydrochloride; Pyrinoline; Quindonium Bromide; Quinidine Gluconate; Quinidine Sulfate; Recainam Hydrochloride; Recainam Tosylate; Risotilide Hydrochloride; Ropitoin Hydrochloride; Sematilide Hydrochloride; Suricainide Maleate; Tocainide; Tocainide Hydrochloride; and Transcainide.

Cardioprotectant: Dexrazoxane; and Draflazine.

Cardiotonic agent: Actodigin; Amrinone; Bemoradan; Butopamine; Carbazeran; Carsatrin Succinate; Deslanoside; Digitalis; Digitoxin; Digoxin; Dobutamine; Dobutamine Hydrochloride; Dobutamine Lactobionate; Dobutamine Tartrate; Enoximone; Imazodan Hydrochloride; Indolidan; Isomazole Hydrochloride; Levdobutamine Lactobionate; Lixazinone Sulfate; Medorinone; Milrinone; Pelrinone Hydrochloride; Pimobendan; Piroximone; Prinoxodan; Proscillaridin; Quazinone; Tazolol Hydrochloride; and Vesnarinone.

Cardiovascular agent: Dopexamine; and Dopexamine Hydrochloride.

Cerebral ischemia Dextrorphan Hydrochloride.

Choleretic: Dehydrocholic Acid; Fencibutirol; Hymecromone; Piprozolin; Sincalide; Tocamphyl.

Cholinergic: Aceclidine; Bethanechol Chloride; Carbachol; Demecarium Bromide; Dexpanthenol; Echothiophate Iodide; Isofluorophate; Methacholine Chloride; Neostiamine Methylsulfate; Neostigmine Bromide; Physostigmine; Physostigmine Salicylate; Physostigmine Sulfate; Pilocarpine Nitrate; and Pyridostigmine Bromide.

Cholinergic agonist: Xanomeline; and Xanomeline Tartrate.

Cholinesterase Deactivator: Obidoxime Chloride; Pralidoxime Chloride; Pralidoxime Iodide; and Pralidoxime Mesylate.

Coccidiostat: Arprinocid; Narasin; Semduramicin; and Semduramicin Sodium.

Cognition adjuvant: Ergoloid Mesylates; Piracetam; Pramiracetam Hydrochloride; Pramiracetam Sulfate; and Tacrine Hydrochloride.

Cognition enhancer: Besipirdine Hydrochloride; Linopirdine; and Sibopirdine.

Contrast Media: Barium Sulfate; Diatrizoate Sodium; Erythrosine Sodium; Iopanoic Acid; Ipodate Calcium; Metyrapone; and Tyropanoate Sodium.

Diagnostic aid: Aminohippurate Sodium; Anazolene Sodium; Arclofenin; Bentiromide; Benzylpenicilloyl Polylysine; Butedronate Tetrasodium; Butilfenin; Coccidioidin; Corticorelin Ovine Triflutate; Corticotropin Zinc Hydroxide; Corticotropin, Repository; Diatrizoate Meglumine; Diatrizoic Acid; Diphtheria Toxin for Schick Test; Disofenin; Ethiodized Oil; Etifenin; Exametazime; Ferristenc; Ferumoxides; Ferumoxsil; Fluorescein; Fluorescein Sodium; Gadobenate Dimeglumine; Gadodiamide; Gadopentetate Dimegiumine; Gadoteridol; Gadoversetamide; Histoplasmin; Impromidine Hydrochloride; Indigotindisulfonate Sodium; Indocyanine Green; Iobenguane Sulfate I 123; Iobenzamic Acid; Iocarmate Meglumine; Iocarmic Acid; Iocetamic Acid; Iodamide; Iodamide Megiumine; Iodipamide Meglumine; Iodixanol; Iodoxamate Meglumine; Iodoxamic Acid; Ioglicic Acid; Ioglucol; Ioglucomide; Ioglycamic Acid; Iogulamide; Iohexyl; Iomeprol; Iopamidol; Iopentol; Iophendylate; Iprocemic Acid; Iopronic Acid; Iopydol; Iopydone; Iosefamic Acid; Ioseric Acid; Iosulamide Meglumine; Iosumetic Acid; Iotasul; Iotetric Acid; Iothalamate Meglumine; Iothalamate Sodium; Iothalamic Acid; Iotrolan; Iotroxic Acid; Ioversol; Ioxagiate Sodium; Ioxaglate Meglumine; Ioxaglic Acid; Ioxilan; Ioxotrizoic Acid; Ipodate Sodium; Iprofenin; Isosulfan Blue; Leukocyte Typing Serum; Lidofenin; Mebrofenin; Meglumine; Metrizamide; Metrizoate Sodium; Metyrapone Tartrate; Mumps Skin Test Antigen; Pentetic Acid; Propyliodone; Quinaldine Blue; Schick Test Control; Sermorelin Acetate; Sodium Iodide I 123; Sprodiamide; Stannous Pyrophosphate; Stannous Sulfur Colloid; Succimer; Teriparatide Acetate; Tetrofosmin; Tolbutamide Sodium; Tuberculin; and Xylose.

Diuretic: Ambuphylline; Ambuside; Amiloride Hydrochloride; Azolimine; Azosemide; Brocrinat; Bumetanide; Chlorothiazide; Chlorthalidone; Clazolimine; Clorexolone; Ethacrynate Sodium; Ethacrynic Acid; Etozolin; Fenquizone; Furosemide; Hydrochlorothiazide; Isosorbide; Mannitol Mefruside; Ozolinone; Piretanide; Spiroxasone; Torsemide; Triamterene; Triflocin; and Urea.

Dopaminergic agent: Ibopamine.

Ectoparasiticide: Nifluridide; Permethrin.

Emetic: Apomorphine Hydrochloride.

Enzyme inhibitor: 30 Polignate Sodium; Acetohydroxamic Acid; Alrestatin Sodium; Aprotinin; Benazepril Hydrochloride; Benazeprilat; Benurestat; Bromocriptine; Bromocriptine Mesylate; Cilastatin Sodium; Fluorofamide; Lergotrile; Lergotrile Mesylate; Levcycloserine; Libenzapril; Pentopril; Pepstatin; Perindopril; Sodium Amylosulfate; Sorbinil; Spirapril Hydrochloride; Spiraprilat; Taleranol; Teprotide; Tolfamide; and Zofenopril Calcium.

Estrogen: Chlorotrianisene; Dienestrol; Diethylstilbestrol; Diethylstilbestrol Diphosphate; Equilin; Estradiol; Estradiol Cypionate; Estradiol Enanthate; Estradiol Undecylate; Estradiol Valerate; Estrazinol Hydrobromide; Estriol; Estrofurate; Estrogens, Conjugated; Estrogens, Esterified; Estrone; Estropipate; Ethinyl Estradiol; Fenestrel; Mestranol; Nylestriol; and Quinestrol.

Fibrinolytic: Anistreplase; Bisobrin Lactate; and Brinolase.

Free oxygen radical scavenger: Pegorgotein.

Gastric Acid Suppressant: Lansoprazole, Pantoprazole and Omeprazole.

Gastrointestinal Motility agents: Cisapride.

Glucocorticoid: Amcinonide; Beclomethasone Dipropionate; Betamethasone; Betamethasone Acetate; Betamethasone Benzoate; Betamethasone Dipropionate; Betamethasone Sodium Phosphate; Betamethasone Valerate; Carbenoxolone Sodium; Clocortolone Acetate; Clocortolone Pivalate; Cloprednol; Corticotropin; Cortisone Acetate; Cortivazol; Descinolone Acetonide; Dexamethasone; Dexamethasone Sodium Phosphate; Diflucortolone; Diflucortolone Pivalate; Flucloronide; Flumethasone; Flumethasone Pivalate; Flunisolide; Fluocinolone Acetonide; Fluocinonide; Fluocortolone; Fluocortolone Caproate; Fluorometholone; Fluperolone Acetate; Fluprednisolone; Fluprednisolone Valerate; Flurandrenolide; Formocortal; Hydrocortisone; Hydrocortisone Acetate; Hydrocortisone Buteprate; Hydrocortisone Butyrate; Hydrocortisone Sodium Phosphate; Hydrocortisone Sodium Succinate; Hydrocortisone Valerate; Medrysone; Methylprednisolone Acetate; Methylprednisolone Sodium Phosphate; Methylprednisolone Sodium Succinate; Nivazol; Paramethasone Acetate; Prednicarbate; Prednisolone; Prednisolone Acetate; Prednisolone Hemisuccinate; Prednisolone Sodium Succinate; Prednisolone Tebutate; Prednisone; Prednival; Ticabesone Propionate; Tralonide; Triamcinolone; Triamcinolone Acetonide; Triamcinolone Acetonide Sodium; Triamcinolone Diacetate; and Triamcinolone Hexacetonide.

Gonad-stimulating principle: Buserelin Acetate; Clomiphene Citrate; Ganirelix Acetate; Gonadorelin Acetate; Gonadorelin Hydrochloride; Gonadotropin, Chorionic; and Menotropins.

Hormone: 17 Alpha Dihydroequilenin; 17 Alpha Dihydroequilin; 17 Alpha Estradiol; 17 Beta Estradiol; 17 Hydroxy Progesterone; Androstenedione; Clomiphene; Cosyntropin; Dehydroepiandrosterone; Dihydroestosterone; Equilenin; Ethyndiol; Follicle Regulatory Protein; Follicle Stimulating Hormone; Folliculostatin; Gonadoctrinins; Gonadorelin; Gonadotropins; Han Memopausal Gonadotropins; Human Chorionic Gonadotropin; Insulin Growth Factor; Leuprolide; Levonorgestrel; Luteinizing hormone; Luteinizing Hormone Releasing Hormone and Analogs; Medroxyprogesterone; Megestrol; Metogest; Norethindrone; Norethynodrel; Norgestrel; Oocyte Maturation Inhibitor; Oxytocin; Pituitary, Posterior; Progesterone; Relaxin; Seractide Acetate; Somalapor; Somatrem; Somatropin; Somenopor; Somidobove; Tamoxifen; Urofollitropin; and Vasopressin.

Hypocholesterolemic: Lifibrol.

Hypoglycemic: Darglitazone Sodium; and Glimepiride.

Hypolipidemic: Azalanstat Dihydrochloride; Colestolone; Surfomer; and Xenalipin.

Hypotensive: Viprostol.

Immunizing agent: Antirabies Serum; Antivenin; Antivenin (Crotalidae) Polyvalent; BCG Vaccine; Botulism Antitoxin; Cholera Vaccine; Diphtheria Antitoxin; Diphtheria Toxoid; Diphtheria Toxoid Adsorbed; Globulin, Immune; Hepatitis B Immune Globulin; Hepatitis B Virus Vaccine Inactivated; Influenza Virus Vaccine; Measles Virus Vaccine Live; Meningococcal Polysaccharide Vaccine Group A; Meningococcal Polysaccharide Vaccine Group C; Mumps Virus Vaccine Live; Pertussis Immune Globulin; Pertussis Vaccine; Pertussis Vaccine Adsorbed; Plague Vaccine; Poliovirus Vaccine Inactivated; Poliovirus Vaccine Live Oral; Rabies Immune Globulin; Rabies Vaccine; Rho(D) Immune Globulin; Rubella Virus Vaccine Live; Smallpox Vaccine; Tetanus Antitoxin; Tetanus Immune Globulin; Tetanus Toxoid; Tetanus Toxoid Adsorbed; Typhoid Vaccine; Vaccinia Immune Globulin; VaricellaZoster Immune Globulin; and Yellow Fever vaccine.

Immunomodulator: Dimepranol Acedoben; Imiquimod; Interferon Beta-1b; Lisofylline; Mycophenolate Mofetil; and Prczatide Copper Acetate.

Immunoregulator: Azarole; Fanetizole Mesylate; Frentizole; Oxamisole Hydrochloride; Ristianol Phosphate; Thymopentin; and Tilomisole.

Immunostimulant: Loxoribine; and Teceleukin.

Immunosuppressant: Azathioprine; Azathioprine Sodium; Cyclosporine; Daltroban; Gusperimus Trihydrochloride; Sirolimus; Tacrolimus.

Impotence therapy adjunct: Delequamine Hydrochloride.

Inhibitor: Acarbose; Atorvastatin Calcium; Benserazide; Brocresine; Carbidopa; Clavulanate Potassium; Dazmegrel; Docebenone; Epoprostenol; Epoprostenol Sodium; Episteride; Finasteride; Flurbiprofen Sodium; Furegrelate Sodium; Lufironil; Miglitol; Orlistat; Pimagedine Hydrochloride; Pirmagrel; Ponalrestat; Ridogrel; Sulbactam Benzathine; Sulbactam Pivoxil; Sulbactam Sodium; Suronacrine Maleate; Tazobactam; Tazobactam Sodium; Ticlopidine Hydrochloride; Tirilazad Mesylate; Tolrestat; Velnacrine Maleate; Zifrosilone; and Zileuton.

Keratolytic: Alcloxa; Aldioxa; Dibenzothiophene; Etarotene; Motretinide-I Picotrin Diolamine; Salicylic Acid; Sumarotene; Tazarotene; Tetroquinone; and Tretinoin.

LHRH agonist: Deslorelin; Goserelin; Histrelin; Lutrelin Acetate; and Nafarelin Acetate.

Liver disorder treatment: Malotilate.

Luteolysin: Fenprostalene.

Memory adjuvant: Dimoxamine Hydrochloride; and Ribaminol.

Mental performance enhancer: Aniracetam.

Mood regulator: Fengabine.

Mucolytic: Acetylcysteine; Carbocysteine; and Domiodol.

Mucosal Protective agents: Misoprostol (Cytotec).

Mydriatic: Berefrine.

Nasal decongestant: Nemazoline Hydrochloride; Pseudoephedrine Polistirex.

Neuroleptic: Duoperone Fumarate; and Risperidone.

Neuromuscular blocking agent: Atracurium Besylate; Cisatracurium Besylate; Doxacurium Chloride; Gallamine Triethiodide; Metocurine Iodide; Mivacurium Chloride; Pancuronium Bromide; Pipecuronium Bromide; Rocuronium Bromide; Succinylcholine Chloride; Tubocurarine Chloride; and Vecuronium Bromide.

Neuroprotective: Dizocilpine Maleate.

NMDA antagonist: Selfotel.

Non-hormonal sterol derivative: Pregnenolone Succinate.

Oxytocic: Carboprost; Carboprost Methyl; Carboprost Tromethamine; Dinoprost; Dinoprost Tromethamine; Dinoprostone; Ergonovine Maleate; Meteneprost; Methylergonovine Maleate; and Sparteine Sulfate.

Paget's disease agents: Tiludronate Disodium.

Progestin: Algestone Acetophenide; Amadinone Acetate; Anagestone Acetate; Chlormadinone Acetate; Cingestol; Clogestone Acetate; Clomegestone Acetate; Desogestrel; Dimethisterone; Dydrogesterone; Ethynerone; Ethynodiol Diacetate; Etonogestrel; Fluorogestone Acetate; Gestaclone; Gestodene; Gestonorone Caproate; Gestrinone; Haloprogesterone; Hydroxyprogesterone Caproate; Lynestrenol; Medrogestone; Medroxyprogesterone Acetate; Methynodiol Diacetate; Norethindrone Acetate; Norgestimate; Norgestomet; Oxogestone Phenpropionate; Quingestanol Acetate; Quingestrone; and Tigestol.

Prostaglandin: Cloprostenol Sodium; Fluprostenol Sodium; Gemeprost; Prostalene; and Sulprostone.

Prostate growth inhibitor: Pentomone.

Prothyrotropin: Protirelin.

Psychotropic: Minaprine.

Radioactive agent: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine 1131; Tolpovidone 1131; Triolein 1125; and Triolein 1131.

Regulator: Calcifediol; Calcitonin; Calcitriol; Clodronic Acid; Dihydrotachysterol; Etidronic Acid; Oxidronic Acid; Piridronate Sodium; Risedronate Sodium; and Secalciferol.

Relaxant: Adiphenine Hydrochloride; Alcuronium Chloride; Aminophylline; Azumolene Sodium; Baclofen; Benzoctamine Hydrochloride; Carisoprodol; Chlorphenesin Carbamate; Chlorzoxazone; Cinflumide; Cinnamedrine; Clodanolene; Cyclobenzaprine Hydrochloride; Dantrolene; Dantrolene Sodium; Fenalamide; Fenyripol Hydrochloride; Fetoxylate Hydrochloride; Flavoxate Hydrochloride; Fletazepam; Flumetramide; Hexafluorenium Bromide; Isomylamine Hydrochloride; Lorbamate; Mebeverine Hydrochloride; Mesuprine Hydrochloride; Metaxalone; Methixene Hydrochloride; Methocarbamol; Nafomine Malate; Nelezaprine Maleate; Papaverine Hydrochloride; Pipoxolan Hydrochloride; Quinctolate; Ritodrine; Ritodrine Hydrochloride; Rolodine; Theophylline Sodium Glycinate; Thiphenamil Hydrochloride; and Xilobam.

Repartitioning agent: Cimaterol.

Scabicide: Amitraz; Crotamiton.

Sclerosing agent: Ethanolamine Oleate; Morrhuate Sodium; Tribenoside.

Sedative: Propiomazine.

Sedative-hypnotic: Allobarbital; Alonimid; Alprazolam; Amobarbital Sodium; Bentazepam; Brotizolam; Butabarbital; Butabarbital Sodium; Butalbital; Capuride; Carbocloral; Chloral Betaine; Chloral Hydrate; Chlordiazepoxide Hydrochloride; Cloperidone Hydrochloride; Clorethate; Cyprazepam; Dexclamol Hydrochloride; Diazepam; Dichloralphenazone; Estazolam Ethchlorvynol; Etomidate; Fenobam; Flunitrazepam; Fosazepam; Glutethimide; Halazepam; Lon-netazepam; Mecloqualone; Meprobamate; Methaqualone; Midaflur; Paraldehyde; Pentobarbital; Pentobarbital Sodium; Perlapine; Prazepam; Quazepam; Reclazepam; Roletamide; Secobarbital; Secobarbital Sodium; Suproclone; Tracazolate; Trepipam Maleate; Triazolam; Tricetamide; Triclofos Sodium; Trimetozine; Uldazepam; Zaleplon; Zolazepam Hydrochloride; and Zolpidem Tartrate.

Selective adenosine A1 antagonist: Apaxifylline.

Serotonin antagonist: Altanserin Tartrate; Amesergide; Ketanserin; and Ritanserin.

Serotonin inhibitor: Cinanserin Hydrochloride; Fenclonine; Fonazine Mesylate; and Xylamidine Tosylate.

Serotonin receptor antagonist: Tropanserin Hydrochloride.

Steroid: Dexamethasone Acefurate; and Mometasone Furoate.

Stimulant Amfonelic Acid; Amphetamine Sulfate; Ampyzine Sulfate; Arbutamine Hydrochloride; Azabon; Caffeine; Ceruletide; Ceruletide Diethylamine; Dazopride Fumarate; Dextroamphetamine; Dextroamphetamine Sulfate; Difluanine Hydrochloride; Dimefline Hydrochloride; Doxapram Hydrochloride; Ethamivan; Etryptamine Acetate; Fenethylline Hydrochloride; Flubanilate Hydrochloride; Fluorothyl; Histamine Phosphate; Indriline Hydrochloride; Mefexamide; Methamphetamine Hydrochloride; Methylphenidate Hydrochloride; Pemoline; Pyrovalerone Hydrochloride; Xamoterol; and Xamoterol Fumarate.

Suppressant: Amflutizole; Colchicine; Tazofelone.

Symptomatic multiple sclerosis: Fampridine.

Synergist: Proadifen Hydrochloride.

Thyroid hormone: Levothyroxine Sodium; Liothyronine Sodium; and Liotrix.

Thyroid inhibitor: Methimazole; and Propylthiouracil.

Thyromimetic: Thyromedan Hydrochloride.

Tranquilizer: Bromazepam; Buspirone Hydrochloride; Chlordiazepoxide; Clazolam; Clobazam; Clorazepate Dipotassium; Clorazepate Monopotassium; Demoxepam; Dexmedetomidine; Enciprazine Hydrochloride; Gepirone Hydrochloride; Hydroxyphenamate; Hydroxyzine Hydrochloride; Hydroxyzine Pamoate; Ketazolam; Lorazepam; Lorzafone; Loxapine; Loxapine Succinate; Medazepam Hydrochloride; Nabilone; Nisobamate; Oxazepam; Pentabamate; Pirenperone; Ripazepam; Rolipram; Sulazepam; Taciamine Hydrochloride; Temazepam; Triflubazam; Tybamate; and Valnoctamide.

Unstable angina agents: Tirofiban Hydrochloride.

Uricosuric: Benzbromarone; Irtemazole; Probenecid; Sulfinpyrazone.

Vasoconstrictor: Angiotensin Amide; Felypressin; Methysergide; and Methysergide Maleate.

Vasodilator: Alprostadil; Azaclorzine Hydrochloride; Bamethan Sulfate; Bepridil Hydrochloride; Buterizine; Cetiedil Citrate; Chromonar Hydrochloride; Clonitrate; Dipyridamole; Droprenilamine; Erythrityl Tetranitrate; Felodipine; Flunarizine Hydrochloride; Fostedil; Hexobendine; Inositol Niacinate; Iproxamine Hydrochloride; Isosorbide Dinitrate; Isosorbide Mononitrate; Isoxsuprine Hydrochloride; Lidoflazine; Mefenidil; Mefenidil Fumarate; Mibefradil Dihydrochloride; Mioflazine Hydrochloride; Mixidine; Nafronyl Oxalate; Nicardipine Hydrochloride; Nicergoline; Nicorandil; Nicotinyl Alcohol; Nimodipine; Nisoldipine; Oxfenicine; Oxprenolol Hydrochloride; Pentaerythritol Tetranitrate; Pentoxifylline; Pentrinitrol; Perhexyline Maleate; Pindolol; Pirsidomine; Prenylamine; Propatyl Nitrate; Suloctidil; Terodiline Hydrochloride; Tipropidil Hydrochloride; Tolazoline Hydrochloride; and Xanthinol Niacinate.

Wound healing agent: Ersofermin.

Xanthine oxidase inhibitor: Allopurinol; and Oxypurinol.

Other active agents include: 16-Alpha Fluoroestradiol; 16Alpha-Gitoxin; 16-Eplestriol; 17 Alpha Estradiol; 17Beta Estradiol; IAlpha-Hydroxyvitamin D2; 1-Decpyrrolidinone; 1-Dodecpyrrolidinone; 22-Oxacalcitriol; 2CVV; 2'-NorcGMP; 3-Isobutyl GABA; 6-FUDCA; 7-Methoxytacrine; Abacavir Sulfate; Abanoquil; Abecarnil; Acadesine; Acamprosate; Acebutolol Hydrochloride; Aceclofenac; Acetomepregenol; Acetrizoate Sodium; Acetylcysteine, N-; Acetyldigitoxin; Acetyl-L-carnitine; Acetylmethadol; Acipimox; Acitemate; Aclatonium; Aconiazide; Acrivastinet; Adafenoxate; Adatanserin; Adefovir Dipivoxil; Adelmidrol; Ademetionine; Adiposin; Adrafinil; Alacepril; Aladapcin; Alaptide; Alatrofloxacin Mesylate; Albolabrin; Albumin Chromated Cr-51 Serum; Albumin Human; Albumin Iodinated I-125 Serum; Albumin Iodinated I-131 Serum; Aldecalmycin; Alendronic Acid; Alentemol; Alfacalcidol; Alfuzosin; Alglucerase; Alinastine; Alitretinoin; Alkavervir; Allopurinol Sodium; Almotriptan Malate; Alosetron; Alpha Idosone; Alpha-Tocopherol; Alpha-Tocopherol Acetate; Alseroxylon; Altromycin B; Amantadine-HCl; Ambenonium Chloride; Amelometasone; Amezinium Metilsulfate; Amfebutamone; Amifloxacin; Aminolevulinic Acid Hydrochloride; Aminosalicylic Acid Resin Complex; Amiodarone Hydrochloride; Amisulpride; Amlodipine; Ammonium Lactate; Amphetamine Adipate; Amphetamine Aspartate; Amphetamine Resin Complex; Ampiroxicam; Amprenavir; Amylin; Amythiamicin; Ananain; Anaritide; Anileridine Phosphate; Anisindione; Anordrin; Apadoline; Apafant; Apraclonidine; Aprepitant; Aprosulate Sodium; Aprotinin Bovine; Aptiganel; Aranidipine; Arbekacin; Arbidol; Arbutamine; Arecatannin B 1; Argatroban; Aripiprazol; Aripiprazole; Arotinolol; Articaine Hydrochloride; Ascorbic Acid; Asimadoline; Aspalatone; Asperfuran; Aspoxicillin; Atazanavir Sulfate; Atenolol, S-; Atevirdine; Atomoxetine Hydrochloride; Atpenin B; Atrinositol; Aureobasidin A; Avobenzone; Azadirachtine; Azelaic Acid; Azelastine; Azelnidipine; Azimilide; Azithromycin Dihydrate; Aztreonwn; Baccatin III; Bacoside A; Bacoside B; Bactobolamine; Balazipone; Balhimycin; Balofloxacin; Balsalazide; Bambuterol; Baohuoside 1; Barnidipine; Batebulast; Beauvericin; Becaplermin; Becliconazole; Beclomethasone Dipropionate Monohydrate; Befloxatone; Bellenamine; Benflumetol; Benidipine; Bentoquatam; Benzisoxazole; Benzoidazoxan; Benzoyl Peroxide; Benzphetamine Hydrochloride; Benzquinamide Hydrochloride; Benztropine; Benzyl Benzoate; Benzyl PenicilloylPolylysine; Bepridil; Beractant; Beraprost; Berlafenone; Bertosamil; Besipirdine; Beta-Carotene; Betaine, Anhydrous; Betamipron; Betaxolol; Betazole Hydrochloride; Bevantolol; Bexarotene; Bifemelane; Bimakalim; Bimatoprost; Bimithil;

Binospirone; Biotin; Bioxalomycin Alpha2; Biriperone; Bisaramil; Bisaziridinylspermine; Bis-Benzimidazole A; Bis-Benzimidazole B; Bismuth Subsalicylate; Bistramide D; Bistramide K; Boldine; Bopindolol; Bortezomib; Brefeldin; Brimonidine; Brinzolamide; Bromfenac; Bucindolol; Budipine; Bunazosin; Butenafine; Butenafine Hydrochloride; Butixocort Propionate; Cabergoline; Caffeine Citrate; Calanolide A; Calcitonin Human; Calcitonin, Salmon; Calcium; Calcium Acetate; Calcium Gluceptate; Calcium Metrizoate; Calfactant; Camonagrel; Candesartan; Candesartan Cilexetil; Candoxatrilat; Capromab; Capsaicin; Carbarnazepine; Carbazomycin C; Carbetocin; Carbidopa/Levodopa; Carbovir; Carboxymethylated Beta-1,3-Glucan; Carperitide; Carteolol; Carumonam; Carvotroline; Caspofungin Acetate; Cebaracetam; Cefadroxil; Cefadroxil Hemihydrate; Cefcapene Pivoxil; Cefdaloxime Pentexil Tosilate; Cefditoren Pivoxil; Cefepime Hydrochloride (Arginine Formulation); Cefetamet; Cefetamet Pivoxil; Cefffietazole; Cefluprenam; Cefminox; Cefodizime; Cefoselis; Cefotiam; Cefotiam Hexetil; Cefozopran; Cefpirome; Cefsulodin; Ceftazidime (Arginine Formulation); Ceftazidime Sodium; Cefteram; Ceftibuten Dihydrate; Ceftriaxone; Celastrol; Celecoxib; Celikalim; Celiprolol; Cellulose Sodium Phosphate; Cepacidine A; Cericlamine; Cerivastatin; Cerivastatin Sodium; Certoparin Sodium; Cetiedil; Cetirizine; Cetyl Alcohol; Cevimeline Hydrochloride; Chlormerodrin, Hg-197; Chlormezanone; Chloroorienticin A; Chloroorienticin B; Cholecalciferol; Cholestyramine; Choriogonadotropin Alfa; Chromic Phosphate, P-32; Chymopapain; Chymotrypsin; Cibenzoline; Ciclesonide; Cicloprolol; Cilansetron; Cilnidipine; Cilobradine; Cilostazol; Cimetropiurn Bromide; Cinitapride; Cinolazepam; Ciprostene; Cisapride Monohydrate; Cisatracurium, Besilate; Cistinexine; Citalopram; Citalopram Hydrobromide; Citicoline; Citreamicin Alpha; Clausenamide; Clidinium Bromide; Clinafloxacin; Clomethiazole; Clopidogrel; Clopidogrel Bisulfate; Cobalt Chloride, Co-57; Cobalt Chloride, Co-60; Colesevelam Hydrochloride; Colestimide; Colfosceril Palmitate; Complestatin; Contignasterol; Contortrostatin; Corticotropin Zinc Hydroxide; Cosalane; Costatolide; Cotinine; Cournermycin Al; Cryptenamine Acetates; Cryptenamine Tannates; Cucumariosid; Curdlan Sulfate; Curiosin; Cyanocobalamin; Cyanocobalamin, Co-57; Cyanocobalamin, Co-58; Cyanocobalamin, Co-60; Cyclic HPMPC; Cyclobenzaprine; Cyclobut A; Cyclobut G; Cyclocapron; Cyclosin; Cyclothialidine; Cyclothiazomycin; Cycrimine Hydrochloride; Cyproterone; Cysteamine Bitartrate; Cytochalasin B; Dactimicin; Daidzein; Daidzin; Danaparoid; Daphnodorin A; Dapiprazole; Dapitant; Darifenacin; Darlucin A; Darsidomine; Daunorubicin Citrate; DdUTP; Decamethonium Bromide; Deferiprone; Deferoxamine Mesylate; Dehydrodidemnin B; Delapril; Delequamine; Delfaprazine; Delmopinol; Delphinidin; Deoxypyridinoline; Deprodone; Depsidomycinderamciclane; Dermatan Sulfate; Deserpidine; Desirudin; Desloratadine; Desmopressin; Desoxoamiodarone; Desoxyribonuclease; Detajrniurn Bitartrate; Dexketoprofen; Dexloxiglumide; Dexmethylphenidate Hydrochloride; Dexrazoxane Hydrochloride; Dexsotalol; Dextrin 2-Sulphate; Dextroamphetamine Adipate; Dextroamphetamine Resin Complex; Dextroamphetamine Saccharate; Dextrose; Diclofenac Digolil; Dicranin; Dienogest; Diethylhomospennine; Diethylnorspermine; Difenoxin Hydrochloride; Dihydrexidine; Diltiazeim; Dimethyl Prostaglandin A1; Dimethylhomospermine; Dimiracetarn; Dimyristoyl Lecithin; Diphemanil Methylsulfate; Diphencyprone; Diphenylpyraline Hydrochloride; Diprafenone; Dipropylnorspermine; Discodermolide; Divalproex; Docarpamine; Docosanol, 1-; Dolasetron Mesylate Monohydrate; Domitroban; Donepezil Hydrochloride; Dorzolamide; Dosmalfate; Dotarizine; Doxazosin; Doxercalciferol; Draculin; Drosperidone; Drospirenone; Drotaverine Acephyllinate; Droxicam; Dutasteride; Ebiratide; Ebrotidine; Ecabapide; Ecabet; Ecdisteron; Echicetin; Echistatin; Ecteinascidin 722; Ecteinascidin 729; Ecteinascidin 743; Edaravone; Edetate Calcium Disodium; Edetate Disodium; Edobacomab; Edrecolornab; Efavirenz; Efegatran; Efonidipine; Egualen; Elcatonin; Eletriptan; Eletriptan Hydrobromide; Elgodipine; Eliprodil; Eltenac; Emakalim; Emedastine; Emedastine Difumarate; Emiglitate; Emoctakin; Emtricitabine; Enalapril; Enazadrem; Enfuvirtide; Englitazone; Entacapone; Enterostatin; Eplerenone; Epoxymexrenone; Eptastigmine; Eptifibatide; Erdosteine; Ergocalciferol; Ersentilide; Ertapenem Sodium; Erythritol; Escitalopram Oxalate; Esomeprazole Magnesium; Estazolam; Estradiol Acetate; Esuprone; Etanterol; Ethacizin; Ethchlorvynol; Ethinamate; Ethinylestradiol; Ethoxzolamide; Etidocaine Hydrochloride; Etizolam; Etrabamine; Eveminomicin; Examorelin; Ezetimibe; Faerieftmgin; Fantofarone; Farnciclovir; Faropenem; Fasidotril; Fasudil; Fedotozine; Felbarnate; Fenofibrate; Fenoldopam; Fenspiride; Fentanyl; Fenticonazole; Fepradinol; Ferpifosate Sodium; Ferristene; Ferrixan; Ferrous Citrate, Fe-59; Fexofenadine Hydrochloride; Fibrinogen, 1-125; Fibrinolysin; Flecainide; Flerobuterol; Flesinoxan; Flezelastine; Flobufen; Flomoxef; Florfenicol; Florifenine; Flornastat; Flosatidil; Fludeoxyglucose, F-18; Flumecinol; Flunarizine; Fluocalcitriol; Fluoxetine, R-; Fluoxetine, S-; Fluparoxan; Flupirtine; Flurbiprofen Axetil; Flurithromycin; Flutamide; Flutrimazole; Fluvastatin; Fluvoxamine; Folic Acid; Follitropin Alfa; Follitropin Alfa/Beta; Fomivirsen Sodium; Fondaparinux Sodium; Forasartan; Formoterol; Formoterol Fumarate; Formoterol, R,R; Fosinopril; Fosphenyloin; Frovatriptan Succinate; Fulvestrant; Furosernide; Gadobenic Acid; Gadobutrol; Gadodiamide-EOB-DTPA; Gadopentetate Dimeglumine; Gadoteric Acid; Galantamine; Galantamine Hydrobromide; Galdansetron; Gallopamil; Gamolenic Acid; Gatifloxacin; Gefitinib; Gemifloxacin Mesylate; Gemtuzumab Ozogamicin; Gepirone; Girisopam; Glaspimod; Glatiramer Acetate; Glaucocalyxin A; Glucagon Hydrochloride; Glucagon Hydrochloride Recombinant; Glucagon Recombinant; Gluconolactone; Glutapyrone; Glutathione Disulfide; Glycopine; Glycopril; Goserelin Acetate; Grepafloxacin; Grepafloxacin Hydrochloride; Guaifenesin; Guanidine Hydrochloride; Halichondrin B; Halofantrine; Halomon; Haloperidol Lactate; Halopredone; Hatomarubigin C; Hatornambigin D; Hatornamicin; Hatornarubigin A; Hatornarubigin B; Heparin Calcium; Heparin Sodium; Hexocyclium Methylsulfate; Hexylcaine Hydrochloride; Histrelin Acetate; Hyaluronidase; Hydrocortamate Hydrochloride; Hydrocortisone Cypionate; Hydrocortisone Probutate; Hydroquinone; Hydroxocobalamin; Hydroxypropyl Cellulose; Hydroxystilbamidine Isethionate; Ibandronate Sodium; Ibogaine; Ibudilast; Ibuprofen Potassium; Icodextrin; Illimaquinone; Iloprost; Imatinib Mesylate; Imidapril; Imidazenil; Imiglucerase; Imipramine Pamoate; Inaminone Lactate; Indapamide; Indinavir; Indinavir Sulfate; Indium In-I11 Oxyquinoline; Indium In-I11 Pentetate Disodium; Indium In-I11 Pentetreotide Kit; Indometacin; Indometacin Farnesil; Indomethacin Sodium; Inocoterone; Inogatran; Inolimomab; Insulin Aspart; Insulin Aspart Protamine; Insulin Glargine; Insulin Lispro Protamine; Interferon Alfa; Interferon Alfa-NI; Interferon Beta; Interferon Beta-1al; Interferon Gamma-I A; Interferon Gamma-I B; Interferon Omega; Interferon, Consensus; Interleukin-3; Interleukin-1; Interleukin-I Beta; Interleukin-10; Interleukin-11; Interleukin-12; Interleukin- 15; Interleukin-2; Interleukin-4; Interleukin-5; Interleukin-7; Interleukin-8; InterleukinI Alpha; Intrinsic Factor; Inulin; Invert Sugar; Iobenguane Sulfate I 131; Iobitridol; Iodamide Meglumine; Iodipamide Sodium; Iodoamiloride; Iodohippurate Sodium, 1-123; Iodohippurate Sodium, 1-131; Iofetamine Hydrochloride 1-123; Iofratol; Iopromide; Iopyrol; Iorneprol; Iothalamate Sodium, 1-125; Iotriside; Ioxaglate Sodium; Ipazilide; Ipenoxazone; Ipidacrine; Ipomeanol, 4; Ipriflavone; Ipsapirone; Irbesartan; Irloxacin; Iron Dextran; Iron Sucrose; Irternazole; Isalsteine; Isbogrel; Iseparnicin; Isofloxythepin; Isopropyl Unoprostone; Itameline; Itopride; Ketoprofen, R-; Ketoprofen, S-; Ketorolac; Lactitol; Lactivicin; Lactulose; Laennec; Lafutidine; Lanoconazole; Lanperisone; Larnifiban; Larnotrigine; Latanoprost; Lateritin; Laurocaprarn; Leflunomide; Lemefloxacin; Leminoprazole; Lenercept; Lepirudin; Leptin; Lercanidipine; Lerisetron; Lernildipine; Lesopitron; Letrazuril; Leucomyzin; Levalbuterol Hydrochloride; Levallorphan Tartrate; Levamisole Hydrochloride; Levetiracetam; Levobetaxolol; Levobunolol; Levobupivacaine; Levobupivacaine Hydrochloride; Levocabastine; Levocarnitine; Levodropropizine; Levofloxacin; Levopropoxyphene Napsylate, Anhydrous; Levormeloxifene; Levornoprolol; Levosimendan; Levosulpiride; Lindane; Linezolid; Linotroban; Linsidornine; Lintitript; Lintopride; Lipase; Lirexapride; Lithium Carbonate; Lithium Citrate; Lodoxamide; Lomerizine; Lonazolac; Lopinavir; Lorglumide; Losartan; Losigamone; Loteprednol; Loviride; Loxapine Hydrochloride; LpdR; Lubeluzole; Lutetium; Luzindole; Lydicamycin; Lysostaphin; Magainin 2 Amide; Magnesium Acetate; Magnesium Acetate Tetrahydrate; Magnolol; Malathion; Mallotochromene; Mallotojaponin; Mangafodipir; Mangafodipir Trisodium; Manidipine; Maniwamycin A; Mannitol; Manurnycin E; Manurnycin F; Mapinastine; Martek 8708; Martek 92211; Massetolide; Meglumine Metrizoate; Meloxicam; Melphalan Hydrochloride; Menadiol Sodium Diphosphate; Menadione; Meprednisone; Mequinol; Mersalyl Sodium; Mesna; Metformin Hydrochloride; Methantheline Bromide; Metharbital; Methoxamine Hydrochloride; Methoxatone; Methoxsalen; Methscopolamine Bromide; Methyclothiazide; Methyldopa; Methylhistamine, R-alpha; Methylinosine Monophosphate; Methylprednisolone Aceponate; Methyprylon; Metipamide; Metipranolol Hydrochloride; Metolazone; Metoprolol Fumarate; Metoprolol, S-; Metoprotol Tartrate; Metrifonate; Metrizoate Magnesium; Metrizoic Acid; Mezlocillin Sodium Monohydrate; Michellarnine B; Microcolin A; Midodrine; Miglustat; Milacemide; Milarneline; Mildronate; Milnacipran; Milrinone Lactate; Miokarnycin; Mipragoside; Mirfentanil; Mivazerol; Mixanpril; Mizolastine; Mizoribine; Moexipril; Moexipril Hydrochloride; Mofezolac; Mometasone; Mometasone Furoate Monohydrate; Monobenzone; Montirelin; Moracizine; Moricizine Hydrochloride; Mosapramine; Mosapride; Motilide; Moxifloxacin Hydrochloride; Moxiraprine; Moxonidine; Mupirocin; Mupirocin Calcium; Mycophenolate Mofetil Hydrochloride; Nadifloxacin; Nadroparin Calcium; Nafadotride; Nafamostat; Naftopidil; Naglivan; Nalmefene Hydrochloride; Naltrexone Hydrochloride; Napadisilate; Napsagatran; Naratriptan; Nasaruplase; Nateglinide; Nateplasel; Nelfinavir Mesylate; Nesiritide; Niacinamide; Nicotine; Nicotine Polacrilex; Niperotidine; Niravoline; Nisin; Nitazoxanide; Nitecapone; Nitisinone; Nitrendipine, S-; Nitrofurantoin Monohydrate; Nitrofurantoin Sodium; Nitrofurantoin, Macrocrystalline; Nitrofurazone; Nitroglycerin; Nonoxynol-9; Norelgestromin; Octyl Methoxycinnamate; Olmesartan Medoxomil; Olopatadine; Olopatadine Hydrochloride; Olprinone; Olsalazine; Omeprazole Magnesium; Ondansetron, R-; Oral Hypoglyceremics; Orphenadrine Hydrochloride; Oseltamivir Phosphate; Otenzepad; Oxamisole; Oxaprozin Potassium; Oxcarbazepine; Oxiconazole; Oxiracetam; Oxodipine; Oxybenzone; Oxybutynin; Oxyphencyclimine Hydrochloride; Oxyphenonium Bromide; Ozagrel; Palauamine; Palinavir; Palonosetron Hydrochloride; Pamaparin Sodium; Panamesine; Pancrelipase; Panipenem; Panipenum; Pannorin; Panornifene; Pantethine; Pantoprazole Sodium; Pantothenic Acid; Paramethadione; Paricalcitol; Parnaqueside; Parnicogrel; Paroxetine Hydrochloride; Paroxetine Mesylate; Parthenolide; Pazufloxacin; Pegademase Bovine; Pegvisomant; Pemirolast; Pemirolast Potassium; Penciclovir Sodium; Penicillamine; Pentafuside; Pentagastrin; Pentamidine; Pentamidine Isethionate; Pentetate Calcium Trisodium Yb-169; Pentigetide; Pentolinium Tartrate; Pentosan; Perflexane; Perfluoropolymethylisopropyl Ether; Perflutren; Pergolide; Pergolide Mesylate; Perindoprilat; Pernedolac; Perospirone; Phenaridine; Phenindione; Pheniramine Maleate; Phenmetrazine Hydrochloride; Phenotoxifvline; Phenserine; Phensuccinal; Phentermine Resin Complex; Phentolamine Mesilate; Phenylalanyl Ketoconazole; Phenylephrine Bitartrate; Phenyloin Sodium, Extended; Phenyloin Sodium, Prompt; Phosphoric Acid; Phytonadione; Picenadol; Picroliv; Picumeterol; Pidotimod; Pilsicainide; Pimagedine; Pimecrolimus; Pimilprost; Pinocebrin; Pioglitazone; Piperonyl Butoxide; Pirlindole; Pirmenol; Pirodornast; Polyestradiol Phosphate; Polyethylene Glycol 3350; Polytetrafluoroethylene; Poractant Alfa; Potassium Chloride; Pramipexole Dihydrochloride; Praziquantel; Prazosin; Prilocaine; Procaine Merethoxylline; Proguanil Hydrochloride; Propagermanium; Propentofylline; Propiolactone; Propiomazine Hydrochloride; Propionylcamitine, L-; Propiram; Propiram+Paracetarnol; Propiverine; Prostratin; Protegrin; Protein Hydrolysate; Protokylol Hydrochloride; Protosufloxacin; Prulifloxacin; Pyrethrins; Pyridoxine; Pyridoxine Hydrochloride; Quazeparn; Quetiapine; Quetiapine Fumarate; Quiflapon; Quinagolide; Quinapril; Quinethazone; Quinidine Polygalacturonate; Raloxifene; Ramatroban; Ranelic Acid; Ranolazine; Rapacuronium Bromide; Recainarn; Regavirumab; Repaglinide; Rescinnamine; Resinferatoxin; Reticulon; Reviparin Sodium; Revizinone; Riboflavin; Riboflavin Phosphate Sodium; Ricasetron; Rilopirox; Rimantadine; Rimexolone; Rimoprogin; Riodipine; Ripisartan; Risedronic Acid; Rispenzepine; Ritipenem Acoxil; Ritipenem; Ritonavir; Rivastigmine Tartrate; Rizatriptan Benzoate; Rnibefradil; Rnivacurium Chloride; Rofecoxib; Rokitamycin; Ropinirole; Ropivacaine; Ropivacaine Hydrochloride Monohydrate; Roquinirnex; Rose Bengal Sodium, 1131; Rosiglitazone Maleate; Roxatidine; Roxindole; Rubidium Chloride Rb-82; Rufloxacin; Rupatidine; Ruzadolane; Sacrosidase; Safflower Oil; Safironil; Salbutarnol, R-; Salnacedin, R-; Samarium Sm 153 Lexidronam Pentasodium; Sanfetrinem; Saprisartan; Sapropterin; Saquinavir; Sarcophytol A Sargramostim; Sarneridine; Sarnpatrilat; Sarpogrelate; Saruplase; Saterinone; Satigrel; Satumomab Pendetide; Scopolamine; Secretin; Selenomethionine, Se-75; Sematilide; Sermorelin; Sernotiadil; Sertaconazole; Sertraline; Sertraline-HCl; Setiptiline; Sevelamer Hydrochloride; Sevirurnab; Sezolamide; Sildenafil Citrate; Silipide; Silteplase; Silver Sulfadiazine; Simendan; Simethicone; Simethicone-Cellulose; Sinitrodil; Sinnabidol; Sipatrigine; Sirnvastatin; Somatomedin C; Somatropin Recombinant; Sorbitol; Sornatomedin B; Sornatrem; Somatropin; Sotalol; Staurosporine; Stepronin; Stobadine; Strontium Chloride, Sr-89; Succibun; Sulfanilamide; Sulfaphenazole; Sulfapyridine; Sulfoxamine; Sulfoxone Sodium; Sulfur; Sultamicillin; Sultopride; Sumatriptan; Sutilains; Symakalim; Talbutal; Tandospirone; Tannic Acid; Tapgen; Taprostene; Tartaric Acid; Tazanolast; Tegaserod Maleate; Telenzepine; Telmesteine; Telmisartan; Temocapril; Tenofovir Disoproxil Fumarate; Tenosal; Tepirindole; Terazosin; Terbinafine Hydrochloride; Terflavoxate; Terguride; Terlipressin; Terodiline; Tertatolol; Testosterone Buciclate; Thallous Chloride, T1-201; Thiamine; Thiamine Hydrochloride; Thiofedrine; Thiomarinol; Thioperamide; Thiosemicarbazone; Thonzonium Bromide; Thyroglobulin; Thyrotropin; Thyrotropin Alfa; Tiagabine; Tiagabine Hydrochloride; Tianeptine; Tiapafant; Ticlopidine; Tienoxolol; Tilisolol; Tilnoprofen Arbamel; Tiludronic Acid; Tiopronin; Tiotropium Bromide; Tirandalydigin; Tirilazad; Tirofiban; Tiropramide; Tocopherol Acetate; Tolterodine Tartrate; Torasemide; Trafennin; Trandolapril; Tranylcypromine Sulfate; Travoprost; Traxanox; Trazodone-HCl; Treprostinil Sodium; Tretinoin Tocoferil; Triarntevene; Tricaprilin; Trichohyalin; Trichosanthin, Alpha; Triclosan; Tridihexethyl Chloride; Trientine; Trientine Hydrochloride; Triflavin; Trimegestone; Trimethoprim Hydrochloride; Trioxsalen; Triptorelin Pamoate; Trolamine Polypeptide Oleate Condensate; Trombodipine; Trometarnol; Tromethamine; Tropine Ester; Trospectomycin; Trovafloxacin; Trovafloxacin Mesylate; Trovirdine; Tucaresol; Tulobuterol; Tylogenin; Tyloxapol; Undecoylium Chloride; Undecoylium Chloride Iodine Complex; Unoprostone Isopropyl; Urapidil; Urea, C-13; Urea, C-14; Uridine Triphosphate; Valaciclovir; Valdecoxib; Valganciclovir Hydrochloride; Valproate Magnesium; Valproate Semisodium; Valrubicin; Valsartan; Vamicamide; Vanadeine; Vaminolol; Vasopressin Tannate; Venlafaxine; Verapamil, (S); Veratrum Viride; Veroxan; Vexibinol; Vinburnine Citrate; Vinburnine Resinate; Vinconate; Vinpocetine; Vinpocetine Citrate; Vintoperol; Viomycin Sulfate; Vitamin A; Vitamin A Palmitate; Vitamin E; Vitamin K; Voriconazole; Voxergolide; Warfarin Potassium; Xemilofiban; Ximoprofen; Yangarnbin; Zabicipril; Zacopride; Zacopride, R-; Zafirlukast; Zalospirone; Zaltoprofen; Zanamivir; Zanarnivir; Zankiren; Zatebradine; Zatosetron; Zenarestat; Zinostatin Stimalarner; Ziprasidone; Ziprasidone Mesylate; Zoledronic Acid; Zolmitriptan; Zolpidem; Zopiclone; Zopiclone, S-; Zopolrestat; and Zotepine.

Still other examples of therapeutically active agents are listed in 2000 MedAd News 19:56-60 and The Physicians Desk Reference, 53rd. Edition, pages 792-796, Medical Economics Company (1999).

Embodiments of the invention will be described with reference to the following Examples which are provided for illustrative purposes only and should not be used to limit the scope of or construe the invention.

EXAMPLES

Materials and Methods for Examples 1-7

A number of formulations (described in Examples 1-7 below) containing diclofenac sodium (a non-steroidal anti-inflammatory drug or NSAID) were tested for permeation through porcine skin using the Franz diffusion cells [as generally described in Franz T J: Percutaneous absorption. On the relevance of in vitro data. J. Invest Dermatol 1975; 64:190-195].

More specifically, Franz cells with a 5 ml receptor well volume were used in conjunction with full-thickness porcine skin harvested at Perry Scientific (San Diego, Calif.). The porcine skin was shaved free of hair, washed with water and subcutaneous fat was removed. The donor well had an area of ~0.5 cm². Receptor wells were filled with isotonic phosphate buffered saline (PBS) doped with 0.01% sodium azide. The flanges of the Franz cell were coated with vacuum grease to ensure a complete seal and were clamped together with uniform pressure using a pinch clamp (SS #18 VWR 80073-350).

After the Franz cells were assembled, the porcine skin was allowed to pre-hydrate for 45 minutes with isotonic PBS. Isotonic PBS was then removed and 200 ml of the formulation was applied to the donor well. Receptor wells of the Franz cells were maintained at 37° C. (temperature on the surface of the skin is ~30° C.) in a stirring block with continual agitation via a stir bar.

The flux rates were calculated by assuming a radius of 0.4 cm in the donor well (i.e., an area of 0.503 cm²). The HPLC calibration curve for diclofenac was determined to have a slope of 115.6 AUC/(µg diclofenac/ml).

Samples were drawn from the receptor wells at t=24 hours and t=46 hours for all formulations. Franz diffusion cell measurements were made in five-fold replicates for each formulation.

The concentration of diclofenac in the samples was measured using HPLC analysis. Specifically, HPLC was carried out with C18 column and using acetonitrile and water as the mobile phase. Flux rates were calculated using standard equations based on the total transference of diclofenac across the skin after 46 hours. Thus, flux rates, F, were computed according to $$F = \frac{D * V}{t * A},$$

wherein: D is the concentration of the drug in the receptor well after incubation time t, V is the volume of the receptor well and A is the surface area of skin.

Individual penetration enhancers in the Examples discussed below were obtained from the following sources:

glyceryl oleate (glycerol monooleate) from TCI (VWR), product code TCG0082 isopropyl myristate from Sigma product code M0757 methyl laurate from Chem Service product code CS0426

N-lauroyl sarcosine from Sigma product code L5000 oleic acid (octadecenoic acid) from Mallinckroft (VWR) product code MK274404 sodium lauryl sulfoacetate from Stepan (65-72%) product code Lathanol LAL sodium octyl sulfate from Alfa Aesar (VWR) product code AA43750-06

The base composition used for each formulation of a carrier composition comprising isotonic PBS, ethanol, propylene glycol and propylene glycol 300 in a volume ratio of 2:2:1:1. The base formulation further comprised diclofenac sodium in a concentration of 1.5 wt. % per unit volume of the base composition. In the Examples below, various combinations of the MPE™s detailed below were added to the base composition.

Example 1

In this Example, N-lauroyl sarcosine (NLS) and isopropyl myristate (IM) were added to the base formulation. The details of each formulation and the results of the Franz diffusion cell experiments are set out in Table 3.

With reference to Table 3, it can be seen that Formulation 2 (containing a mixture of NLS and IM each at a concentration 2.5% wt/vol.) was more effective at enhancing diclofenac sodium flux rates through the skin when compared to either of Formulation 3 (containing 5% wt./vol NLS and no IM) or Formulation 4 (containing 5% wt./vol IM and no NLS).

Further and surprisingly, Formulation 1 (containing a mixture of NLS and IM each at a concentration of 1.5% wt./vol) was approximately seven times more effective at enhancing the flux rate of the diclofenac sodium when compared to Formulation 2.

Example 2

In this Example, N-lauroyl sarcosine (NLS) and oleic acid (OA) were added to the base formulation. The details of each formulation and the results of the Franz diffusion cell experiments are set out in Table 4.

With reference to Table 4, it can be seen that Formulation 5 (containing a mixture of NLS and OA each at a concentration 1.5% wt./vol.) was more effective at enhancing diclofenac sodium flux rate through the skin when compared to either of Formulation 6 (containing 5% wt./vol NLS and no OA) or Formulation 7 (containing 5% wt./vol OA and no NLS).

It is notable that the flux rate of the NSAID in Formulation 5 was higher than that achieved by either of Formulation 6 or Formulation 7 in spite of the fact that the total concentration of the molecular penetration enhancers in Formulation 5 was lower than that in Formulation 6 and Formulation 7.

Example 3

In this Example, sodium octyl sulfate (SOS) and oleic acid (OA) were added to the base formulation. The details of each formulation and the results of the Franz diffusion cell experiments are set out in Table 5.

With reference to Table 5, it can be seen that Formulation 8 (containing a mixture of SOS and OA each at a concentration 1.5% wt/vol and 3.5% wt/vol, respectively) was more effective at enhancing diclofenac sodium flux rate through the skin when compared to either of Formulation 9 (containing 5% wt./vol OA and no SOS) or Formulation 10 (containing 5% wt./vol SOS and no OA).

Example 4

In this Example, glyceryl oleate (GO) and sodium octyl sulfate (SOS) were added to the base formulation. The details of each formulation and the results of the Franz diffusion cell experiments are set out in Table 6.

With reference to Table 6, it can be seen that Formulation 11 (containing a mixture of GO and SOS each at a concentration 1.5% wt./vol.) was approximately as effective at enhancing diclofenac sodium flux rate through the skin as Formulation 12 (containing 5% wt./vol GO and no SOS) and was substantially improved over that of Formulation 13 (containing 5% wt./vol SOS and no GO).

Example 5

In this Example, glyceryl oleate (GO) and methyl laurate (ML) were added to the base formulation. The details of each formulation and the results of the Franz diffusion cell experiments are set out in Table 7.

With reference to Table 7, it can be seen that Formulation 14 (containing a mixture of GO and ML each at a concentration 2.5% wt/vol.) was more effective at enhancing diclofenac sodium flux rate through the skin when compared to either of Formulation 15 (containing 5% wt/vol GO and no ML) or Formulation 16 (containing 5% wt./vol ML and no GO).

Example 6

In this Example, sodium lauryl sulfoacetate (SLSA) and methyl laurate (ML) were added to the base formulation. The details of each formulation and the results of the Franz diffusion cell experiments are set out in Table 8.

With reference to Table 8, it can be seen that Formulation 17 (containing a mixture of SLSA and ML each at a concentration 2.5% wt/vol.) was more effective at enhancing diclofenac sodium flux rate through the skin when compared to either of Formulation 18 (containing 5% wt./vol SLSA and no ML) or Formulation 19 (containing 5% wt./vol ML and no SLSA).

Example 7

In this Example, sodium lauryl sulfoacetate (SLSA) and isopropyl myristate (IM) were added to the base formulation. The details of each formulation and the results of the Franz diffusion cell experiments are set out in Table 9.

With reference to Table 9, it can be seen that Formulation 20 (containing a mixture of SLSA and IM each at a concentration 2.5% wt/vol.) was more effective at enhancing diclofenac sodium flux rate through the skin when compared to either of Formulation 21 (containing 5% wt./vol SLSA and no IM) or Formulation 22 (containing 5% wt./vol IM and no SLSA).

Materials and Methods for Example 8

Using methodology similar to that described in Examples 1-7, a number of formulations containing other active agents (as described in greater detail below) were tested for permeation through porcine skin using Franz diffusion cells.

Franz Cell Guidelines:

Skin Preparation:

Porcine skin was sourced from Lampire Biological Laboratories (Pipersville, Pa.). The skin was then dermatomed in house to a set thickness.

Diffusion Cell Assembly:

Diffusion cells were assembled using dermatomed porcine skin as the substrate. Cell assembly was carried out by clamping the skin between a donor well (the flange was coated with a thin coating of vacuum grease to ensure a proper seal) and a receptor well. The wells were clamped together and held in place using a spring clamp. The receptor wells had a volume of 3.3 ml and the clamped skin had an available surface area of ~0.55 $cm^2$ for the diffusion study. Once the cell was assembled, the receptor well was filled with PBS containing 0.01 wt % $NaN_3$ (to help prevent skin degradation). Care was taken to ensure all bubbles are removed from the receptor solution. The skin was allowed to pre-hydrate for 20 minutes before the formulations were applied to the skin.

Diffusion Cell Testing:

After the skin was prehydrated, 40 µl of the test formulation was applied to the skin with a positive displacement pipettor and the applied dose then rubbed gently across the skin with a glass stir rod. Once the formulation was applied, a stir bar was added to the receptor well. The receptor well was maintained at 32° C. and continuously agitated throughout the experiment. Sample aliquots were drawn from the receptor well at varying time points and replaced with fresh PBS buffer. Sample aliquots were filtered and analyzed for concentration of the active using HPLC analysis. Measurements for each formulation were carried out in six-fold replicates.

The individual penetration enhancers used in Example 8 are provided in the following table along with their abbreviation (Abbr) and Chemical Abstract Service (CAS) registry number:

| Abbr. | Chemical | CAS No. |
|---|---|---|
| IM | Isopropyl Myristate | 110-27-0 |
| SLSA | Sodium Lauryl Sulfoacetate | 1847-58-1 |
| OA | Oleic Acid | 112-801-1 |
| ML | Methyl Laurate | 111-82-0 |
| GO | Glyceryl Monooleate | 31566-31-1 |
| NLS | N-lauroyl Sarcosine | 97-78-9 |

Numerous formulations were prepared with the MMPE™s used in conjunction with varying active agents. MMPE™s tested were SLSA/IM, SLSA/ML, IM/NLS, GO/ML, and NLS/OA in a hydroalcoholic solution. These MMPE™s were tested with the active agents ibuprofen, buprorion HCl, ketoprofen and testosterone. Tables 10-19 list the MMPE™s that showed a significant increase in flux when compared to flux from the analogous formulations containing only one of the MPE™s.

TABLE 1

| NSAID | TRADE NAME | STRUCTURE |
|---|---|---|
| Diclofenac | Voltaren, Pennsaid | 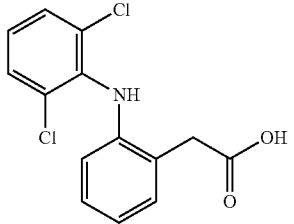 [SMILES: O=C(O)Cc1ccccc1Nc1c(Cl)cccc1Cl] |
| Indomethacin | Indocin | 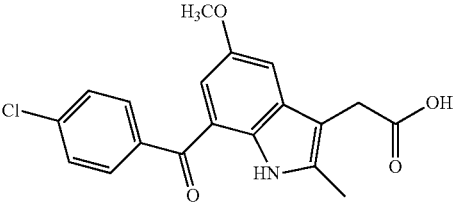 [SMILES: COc1cc(C(=O)c2ccc(Cl)cc2)c2[nH]c(C)c(CC(=O)O)c2c1] |
| Sulindac | Clinoril | 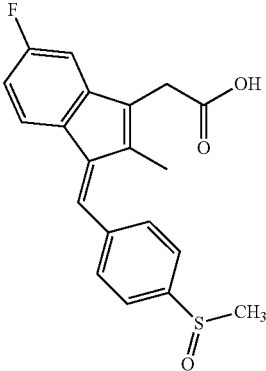 [SMILES: CC1=C(CC(=O)O)c2cc(F)ccc2/C1=C/c1ccc(S(C)=O)cc1] |
| Tolmetin | Tolectin | 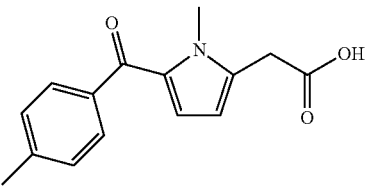 [SMILES: Cc1ccc(C(=O)c2ccc(CC(=O)O)n2C)cc1] |
| Naproxen | Naprosyn, Aleve | 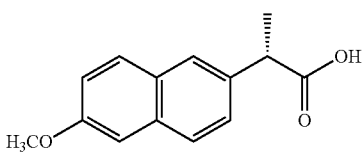 [SMILES: COc1ccc2cc([C@H](C)C(=O)O)ccc2c1] |
| Ibuprofen | Advil, Brufen, Motrin | 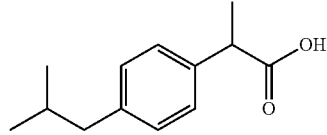 |

TABLE 1-continued
| NSAID | TRADE NAME | STRUCTURE |
|---|---|---|
| Flurbiprofen | Ansaid, Flurwood, Froben | 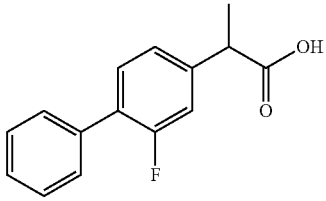 [SMILES: CC(C(=O)O)c1ccc(-c2ccccc2)c(F)c1] |
| Ketoprofen | Orudis | 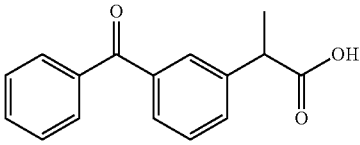 [SMILES: CC(C(=O)O)c1cccc(C(=O)c2ccccc2)c1] |
| Ketorolac | Acular, Toradol | 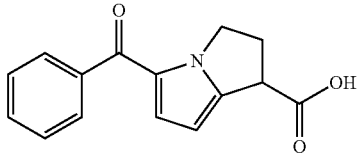 [SMILES: O=C(c1ccccc1)c1ccc2n1CCC2C(=O)O] |
| Fenoprofen | Nalfon | 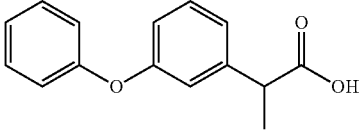 [SMILES: CC(C(=O)O)c1cccc(Oc2ccccc2)c1] |
| Bromfenac | Xibrom | 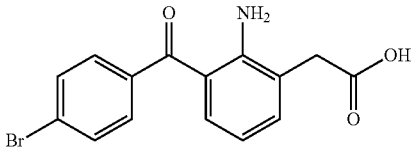 [SMILES: Nc1c(CC(=O)O)cccc1C(=O)c1ccc(Br)cc1] |
TABLE 2
| COMPOUND | TRADE NAME | STRUCTURE |
|---|---|---|
| Acetaminophen | Tylenol | 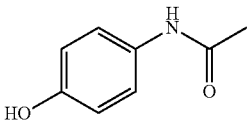 |
| Aspirin | | 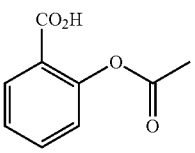 |

TABLE 2-continued
| COMPOUND | TRADE NAME | STRUCTURE |
|---|---|---|
| Celecoxib | Celebrex | 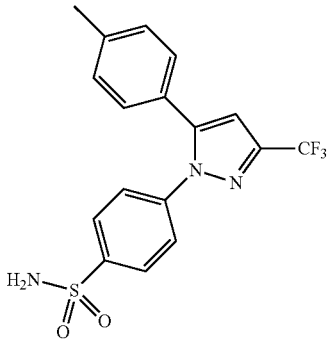 [SMILES: Cc1ccc(-c2cc(C(F)(F)F)nn2-c2ccc(S(N)(=O)=O)cc2)cc1] |
| Diflunisal | Dolobid | 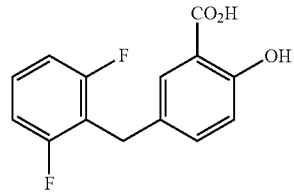 [SMILES: O=C(O)c1cc(Cc2c(F)cccc2F)ccc1O] |
| Etoricoxib | Arcoxia | 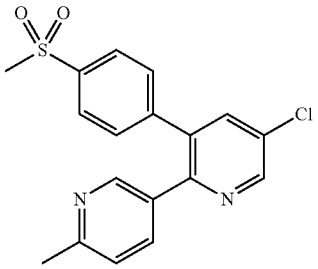 [SMILES: Cc1ccc(-c2ncc(Cl)cc2-c2ccc(S(C)(=O)=O)cc2)cn1] |
| Piroxicam | Feldane, Roxam | 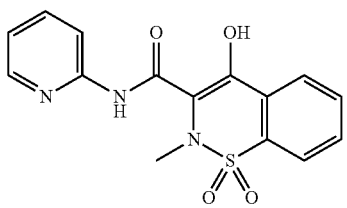 [SMILES: CN1C(C(=O)Nc2ccccn2)=C(O)c2ccccc2S1(=O)=O] |
| Rofecoxib | Vioxx | 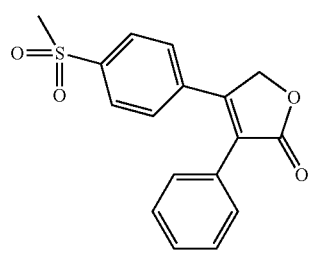 [SMILES: CS(=O)(=O)c1ccc(C2=C(c3ccccc3)C(=O)OC2)cc1] |
| Salsalate | Disalcid, Monogesic, Salflex, Salcitab | 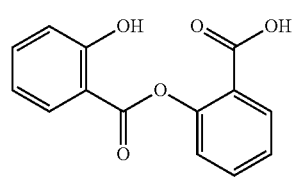 [SMILES: O=C(Oc1ccccc1C(=O)O)c1ccccc1O] |

TABLE 2-continued

| COMPOUND | TRADE NAME | STRUCTURE |
|---|---|---|
| Meloxicam | Mobic | 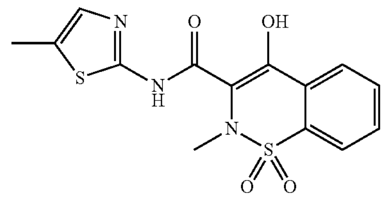 [SMILES: Cc1cnc(NC(=O)C2=C(O)c3ccccc3S(=O)(=O)N2C)s1] |
| Etodolac | Lodine | 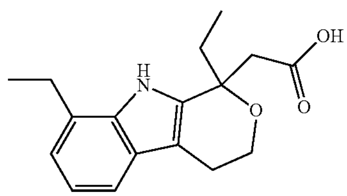 [SMILES: CCc1cccc2c3c([nH]c12)C(CC)(CC(=O)O)OCC3] |
| Oxaprozin | Daypro | 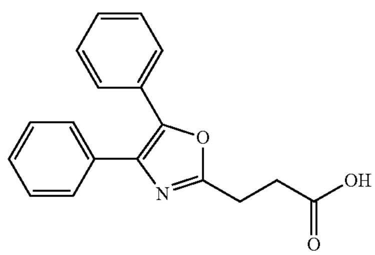 [SMILES: O=C(O)CCc1nc(-c2ccccc2)c(-c2ccccc2)o1] |
| Nabumetone | Relafen | 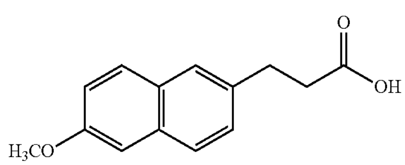 [SMILES: COc1ccc2cc(CCC(=O)O)ccc2c1] |
| Mefenamic acid | Ponstel | 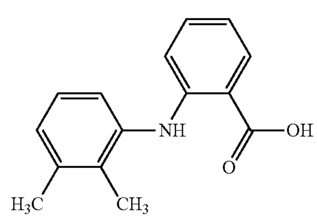 [SMILES: Cc1cccc(Nc2ccccc2C(=O)O)c1C] |
| Meclofenamic Acid | Meclofen, Meclomen | 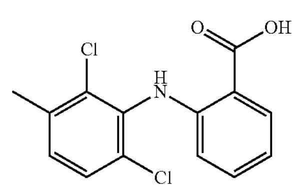 [SMILES: Cc1ccc(Cl)c(Nc2ccccc2C(=O)O)c1Cl] |

TABLE 3

| Formulation | [NLS + IM] (wt. %/vol.) | Weight Ratio of NLS:IM | Flux (μg/hr/cm²) |
|---|---|---|---|
| 1 | 3.0 | 1:1 | 3.80 |
| 2 | 5.0 | 1:1 | 0.53 |
| 3 | 5.0 | 1:0 | 0.26 |
| 4 | 5.0 | 0:1 | 0.02 |

TABLE 4

| Formulation | [NLS + OA] (wt. %/vol.) | Weight Ratio of NLS:OA | Flux (μg/hr/cm²) |
|---|---|---|---|
| 5 | 3.0 | 1:1 | 3.29 |
| 6 | 5.0 | 1:0 | 0.26 |
| 7 | 5.0 | 0:1 | 2.70 |

TABLE 5

| Formulation | [SOS + OA] (wt. %/vol.) | Weight Ratio of SOS:OA | Flux (μg/hr/cm²) |
|---|---|---|---|
| 8 | 5.0 | 3:7 | 4.73 |
| 9 | 5.0 | 1:0 | 2.70 |
| 10 | 5.0 | 0:1 | 0.02 |

TABLE 6

| Formulation | [GO + SOS] (wt. %/vol.) | Weight Ratio of GO:SOS | Flux (μgl/hr/cm²) |
|---|---|---|---|
| 11 | 3.0 | 1:1 | 0.30 |
| 12 | 5.0 | 1:0 | 0.34 |
| 13 | 5.0 | 0:1 | 0.02 |

TABLE 7

| Formulation | [GO + ML] | Weight Ratio of | Flux (μg/hr/cm²) |
|---|---|---|---|
| 14 | 5.0 | 1:1 | 0.54 |
| 15 | 5.0 | 1:0 | 0.34 |
| 16 | 5.0 | 0:1 | 0.32 |

TABLE 8

| Formulation | [SLSA + ML] (wt %/vol) | Weight Ratio of SLSA:ML | Flux (μg/hr/cm²) |
|---|---|---|---|
| 17 | 5.0 | 3:7 | 0.52 |
| 18 | 5.0 | 1:0 | 0.22 |
| 19 | 5.0 | 0:1 | 0.32 |

TABLE 9

| Formulation | [SLSA + IM] (wt %/vol) | Weight Ratio of SLSA:IM | Flux (μg/hr/cm²) |
|---|---|---|---|
| 20 | 5.0 | 1:1 | 0.52 |
| 21 | 5.0 | 1:0 | 0.22 |
| 23 | 5.0 | 0:1 | 0.02 |

TABLE 10

| Formulation | Ibuprofen (wt/wt %) | SLSA (wt/wt %) | IM (wt %/wt %) | Flux (μg/hr/cm²) |
|---|---|---|---|---|
| 23 | 5 | 3 | | 42.1 |
| 24 | 5 | | 3 | 28.5 |
| 25 | 5 | 1.5 | 1.5 | 66.5 |

TABLE 11

| Formulation | Ibuprofen (wt %/wt %) | SLSA (wt %/wt %) | ML (wt %/wt %) | Flux (μg/hr/cm²) |
|---|---|---|---|---|
| 26 | 5 | 3 | | 42.1 |
| 27 | 5 | | 3 | 25.2 |
| 28 | 5 | 1.5 | 1.5 | 53.9 |

TABLE 12

| Formulation | Ibuprofen (wt %/wt %) | IM (wt %/wt %) | NLS (wt %/wt %) | Flux (μg/hr/cm²) |
|---|---|---|---|---|
| 29 | 5 | 3 | | 28.5 |
| 30 | 5 | | 3 | 10.0 |
| 31 | 5 | 1.5 | 1.5 | 31.0 |

TABLE 13

| Formulation | Ibuprofen (wt %/wt %) | GO (wt %/wt %) | ML (wt %/wt %) | Flux (μg/hr/cm²) |
|---|---|---|---|---|
| 32 | 5 | 3 | | 14.4 |
| 33 | 5 | | 3 | 25.2 |
| 34 | 5 | 1.5 | 1.5 | 53.6 |

TABLE 14

| Formulation | Bupropion HCl (wt %/wt %) | NLS (wt %/wt %) | OA (wt %/wt %) | Flux (μg/hr/cm²) |
|---|---|---|---|---|
| 35 | 5 | 3 | | 14.3 |
| 36 | 5 | | 3 | 9.1 |
| 37 | 5 | 1.5 | 1.5 | 18.8 |

TABLE 15

| Formulation | Bupropion HCl (wt %/wt %) | SLSA (wt %/wt %) | IM (wt %/wt %) | Flux (μg/hr/cm²) |
|---|---|---|---|---|
| 38 | 5 | 3 | | 34.3 |
| 39 | 5 | | 3 | 14.5 |
| 40 | 5 | 1.5 | 1.5 | 45.6 |

TABLE 16

| Formulation | Bupropion HCl (wt %/wt %) | SLSA (wt %/wt %) | ML (wt %/wt %) | Flux (μg/hr/cm²) |
|---|---|---|---|---|
| 41 | 5 | 3 | | 34.3 |
| 42 | 5 | | 3 | 14.8 |
| 43 | 5 | 1.5 | 1.5 | 51.3 |

TABLE 17

| Formulation | Bupropion HCl (wt %/wt %). | IM (wt %/wt %). | NLS (wt %/wt %). | Flux (μg/hr/cm²) |
|---|---|---|---|---|
| 44 | 5 | 3 | | 14.5 |
| 45 | 5 | | 3 | 14.3 |
| 46 | 5 | 1.5 | 1.5 | 55.9 |

TABLE 18

| Formulation | Ketoprofen (wt %/wt %). | NLS (wt %/wt %). | OA (wt %/wt %). | Flux (μg/hr/cm²) |
|---|---|---|---|---|
| 47 | 5 | 3 | | 14.3 |
| 48 | 5 | | 3 | 9.1 |
| 49 | 5 | 1.5 | 1.5 | 18.8 |

TABLE 19

| Formulation | Testosterone (wt %/wt %). | SLSA (wt %/wt %). | IM (wt %/wt %). | Flux (μg/hr/cm²) |
|---|---|---|---|---|
| 50 | 5 | 3 | | 14.3 |
| 51 | 5 | | 3 | 9.1 |
| 52 | 5 | 1.5 | 1.5 | 18.8 |

Example 9

Several formulations according to the present disclosure were prepared utilizing the compositional formulations set forth in Tables 20 and 21. Each of the formulations was prepared in batches at a batch size of 2 kg. All raw materials were stored at ambient conditions prior to manufacturing of formulations. Generally, all formulations were manufactured as described below. Specifically, an oil phase was prepared by heating and mixing the mixture of the active agents (local anesthetics) at ~60° C. The parabens, polymer and excipients were added sequentially in water while stirring in combination with homogenization at high shear force, under heated conditions (60-75° C.). The temperature of the mixing vessel was then lowered and the oil phase mixed into water and homogenized at room temperature until a product without any lumps or crystals is obtained. The final product was then tested for the physico-chemical properties and placed on stability at appropriate storage conditions.

TABLE 20

| INGREDIENT | CONTROL (SBM) | F1 | F2 | F3 | F4 | F5 | F6 |
|---|---|---|---|---|---|---|---|
| | | | | WT % | | | |
| Lidocaine | 20 | 20 | 20 | 20 | 20 | 20 | 20 |
| Tetracaine | 20 | 20 | 20 | 20 | 20 | 20 | 20 |
| Polyvinyl Alcohol | 7.2 | 7.2 | 7.2 | 7.2 | 7.2 | 7.2 | 7.2 |
| Sorbitan Monopalmitate | 3 | 3 | 3 | 3 | 3 | 3 | 3 |
| Purified Water | 49.68 | 47.68 | 47.68 | 47.68 | 47.68 | 47.68 | 47.68 |
| Methylparaben | 0.1 | 0.1 | 0.1 | 0.1 | 0.1 | 0.1 | 0.1 |
| Propylparaben | 0.02 | 0.02 | 0.02 | 0.02 | 0.02 | 0.02 | 0.02 |
| Isopropyl myristate | — | 1 | — | — | 1 | — | 1 |
| Oleic Acid | — | 1 | 1 | — | — | 1 | — |
| Glyceryl Oleate | — | — | 1 | 1 | 1 | — | — |
| Sodium Lauryl Sulfoacetate | — | — | — | 1 | — | 1 | 1 |

TABLE 21

| INGREDIENT | F7 | F8 | F9 | F10 | F11 | F12 |
|---|---|---|---|---|---|---|
| | | | | WT % | | |
| Lidocaine | 20 | 20 | 20 | 20 | 20 | 20 |
| Tetracaine | 20 | 20 | 20 | 20 | 20 | 20 |
| Polyvinyl Alcohol | 7.2 | 7.2 | 7.2 | 7.2 | 7.2 | 7.2 |
| Sorbitan Monopalmitate | 3 | 3 | 3 | 3 | 3 | 3 |
| Purified Water | 39.68 | 43.68 | 41.68 | 41.68 | 41.68 | 41.68 |
| Methylparaben | 0.1 | 0.1 | 0.1 | 0.1 | 0.1 | 0.1 |
| Propylparaben | 0.02 | 0.02 | 0.02 | 0.02 | 0.02 | 0.020.02 |
| Isopropyl myristate | 5 | — | — | 5 | — | 5 |
| Oleic Acid | 5 | — | 5 | — | 5 | — |
| Glyceryl Oleate | — | 3 | 3 | 3 | — | — |
| Sodium Lauryl Sulfoacetate | — | 3 | — | — | 3 | 3 |

Example 10

Physical Stability of the Formulations of Example 9

Each of the formulations and the control described in Example 9 were stored at ambient conditions (18° C. to 25° C. and ≤60% RH) and accelerated conditions (40±2° C. and 75%±5 RH). The physical stability (i.e. the phase separation of the formulations) of samples stored at both ambient and accelerated conditions were tested at weeks 1, 2, 3, and 4.

The phase separation was measured by placing the formulation in a 125 mL graduated glass cylinder, stopped, and placed at 25° C. and 40° C. Phase separation in the formulations were then determined by measuring the quantity of oil phase separated at the top of the cylinder in terms of milliliters.

Results for the phase separation for each of the formulations is provided in Tables 22-23 for ambient temperature samples and Tables 24-25 for accelerated temperature samples.

TABLE 22

| Storage (Weeks) | CONTROL | F1 | F2 | F3 | F4 | F5 | F6 |
|---|---|---|---|---|---|---|---|
| 1 | 2 | 0 | 0 | 0 | 0 | 0 | 0 |
| 2 | 1 | 0 | 0 | 0 | 0 | 0 | 0 |
| 3 | 1 | 0 | 0 | 0 | 0 | 0 | 0 |
| 4 | 1 | 0 | 0 | 0 | 0 | 0 | 0 |

TABLE 23

| Storage (Weeks) | F7 | F8 | F9 | F10 | F12 |
|---|---|---|---|---|---|
| 1 | 0 | 0 | 0 | 0 | 0 |
| 2 | 0 | 0 | 0 | 0 | 0 |
| 3 | 0 | 0 | 0 | 0 | 0 |
| 4 | 0 | 0 | 0 | 0 | 0 |

* outlier data from F11 not provided due to potential experimental issues.

The results from the ambient testing are plotted and shown in FIG. 1. Note that since all reported data points for F1-F10 and F12 were 0, only a single line is shown for the formulations of the present disclosure.

TABLE 24

| Storage (Weeks) | CONTROL | F1 | F2 | F3 | F4 | F5 | F6 |
|---|---|---|---|---|---|---|---|
| 1 | 5 | 1 | 5 | 5 | 5 | 0 | 0 |
| 2 | 8 | 7 | 5 | 5 | 10 | 0 | 0 |
| 3 | 7 | 10 | 5 | 7 | 10 | 0 | 0 |
| 4 | 7 | 10 | 7 | 7 | 10 | 0 | 0 |

TABLE 25

| Storage (Weeks) | F7 | F8 | F9 | F10 | F12 |
|---|---|---|---|---|---|
| 1 | 0.5 | 2 | 0 | 0 | 1 |
| 2 | 2 | 2 | 0 | 3 | 2 |
| 3 | 2 | 2 | 0 | 3 | 2 |
| 4 | 2 | 2 | 0 | 5 | 5 |

* outlier data from F11 not provided due to potential experimental issues.

Figure 2:
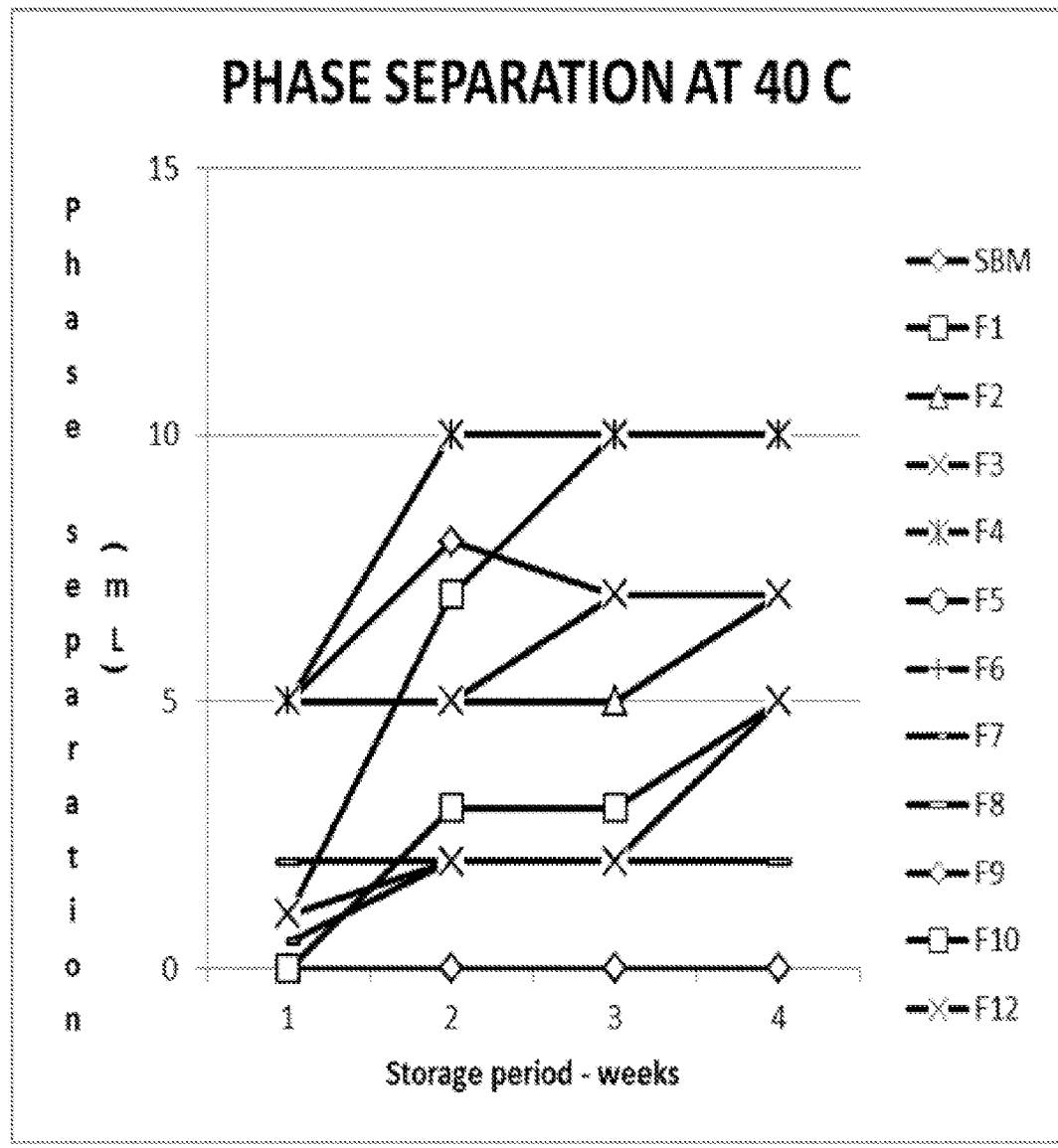
FIG. 2 is a plot of the physical stability (phase separation) at 40° C. of several exemplary embodiments of formulations of the invention disclosed herein.

The results from the ambient testing are plotted and shown in FIG. 2.

Example 11

Chemical Stability of the Formulations of Example 9

Each of the formulations and the control described in Example 9 were tested for the chemical stability of tetracaine following storage at ambient conditions (18° C. to 25° C. and ≤60% RH) and accelerated conditions (40±2° C. and 75%±5 RH). The chemical stability was measured in terms of the generation of the impurity 4-butylaminobenzoic acid (4-BABA), the primary hydrolysis degradation product of tetracaine. Specifically, tetracaine is known to break down to 4-BABA, so a lower concentration of this compound after a period of weeks demonstrates a greater tetracaine stability over time. Samples in both ambient and accelerated conditions were tested initially and at 3 weeks.

The chemical stability of the formulations was assessed by measuring the concentration of the actives (lidocaine & tetracaine) and formation of degradation products, i.e. impurities, such as 4-BABA using High Performance Liquid Chromatographic (HPLC) method. The HPLC method involves chromatographic separation by mobile phase gradient and C18 analytical column; and quantification of each component by ultraviolet (UV) detector.

Results for the chemical stability for each of the formulations is provided in Tables 26-27 for ambient temperature samples and Tables 28-29 for accelerated temperature samples. Each of the tables also includes values for the amount of water reduced in the formulation due to the inclusion of the first compound and second compound as well as calculations for the percent difference (%) in the amount of 4-BABA production of the particular formulation as compared to the 4-BABA production of the Control over the test period.

TABLE 26

| Storage (Weeks) | CONTROL | F1 | F2 | F3 | F4 | F5 | F6 |
|---|---|---|---|---|---|---|---|
| 0 | 0.06 | 0.06 | 0.04 | 0.03 | 0.03 | 0.02 | 0.02 |
| 3 | 0.23 | 0.21 | 0.19 | 0.17 | 0.17 | 0.16 | 0.16 |
| About 52 weeks* | 2.78 | 2.46 | 2.44 | 2.27 | 2.27 | 2.26 | 2.26 |

TABLE 26-continued

| Storage (Weeks) | CONTROL | F1 | F2 | F3 | F4 | F5 | F6 |
|---|---|---|---|---|---|---|---|
| Water Reduction | 0 | 2 | 2 | 2 | 2 | 2 | 2 |
| % Change in 4-BABA at 3 weeks | 0 | −9% | −17% | −26% | −26% | −30% | −30% |
| % Change* in 4-BABA (52 weeks) | 0 | −12% | −12% | −18% | −18% | −19% | −19% |

*data is extrapolated

TABLE 27

| Storage (Weeks) | F7 | F8 | F9 | F10 | F11 | F12 |
|---|---|---|---|---|---|---|
| 0 | 0.04 | 0.01 | 0.03 | 0.025 | 0.025 | 0.02 |
| 3 | 0.16 | 0.13 | 0.18 | 0.15 | 0.19 | 0.12 |
| About 52 weeks* | 1.96 | 1.93 | 2.43 | 2.02 | 2.66 | 1.62 |
| Water Reduction | 10 | 6 | 8 | 8 | 8 | 8 |
| % Change in 4-BABA (3 weeks) | −30% | −43% | −22% | −35% | −17% | −48% |
| % Change* in 4-BABA (52 weeks) | −29% | −31% | −13% | −27% | −4% | −42% |

*data is extrapolated

TABLE 28

| Storage (Weeks) | CONTROL | F1 | F2 | F3 | F4 | F5 | F6 |
|---|---|---|---|---|---|---|---|
| 0 | 0.06 | 0.06 | 0.04 | 0.03 | 0.03 | 0.02 | 0.02 |
| 3 | 0.69 | 0.64 | 0.63 | 0.59 | 0.60 | 0.60 | 0.57 |
| Water Reduction | 0 | 2 | 2 | 2 | 2 | 2 | 2 |
| % Change in 4-BABA | 0 | −7% | −9% | −14% | −13% | −13% | −17% |

TABLE 29

| Storage (Weeks) | F7 | F8 | F9 | F10 | F11 | F12 |
|---|---|---|---|---|---|---|
| 0 | 0.04 | 0.01 | 0.03 | 0.025 | 0.025 | 0.02 |
| 3 | 0.52 | 0.48 | 0.59 | 0.51 | 0.58 | 0.43 |
| Water Reduction | 10 | 6 | 8 | 8 | 8 | 8 |
| % Change in 4-BABA | −25% | −30% | −14% | −26% | −16% | −38% |

Figure 3:
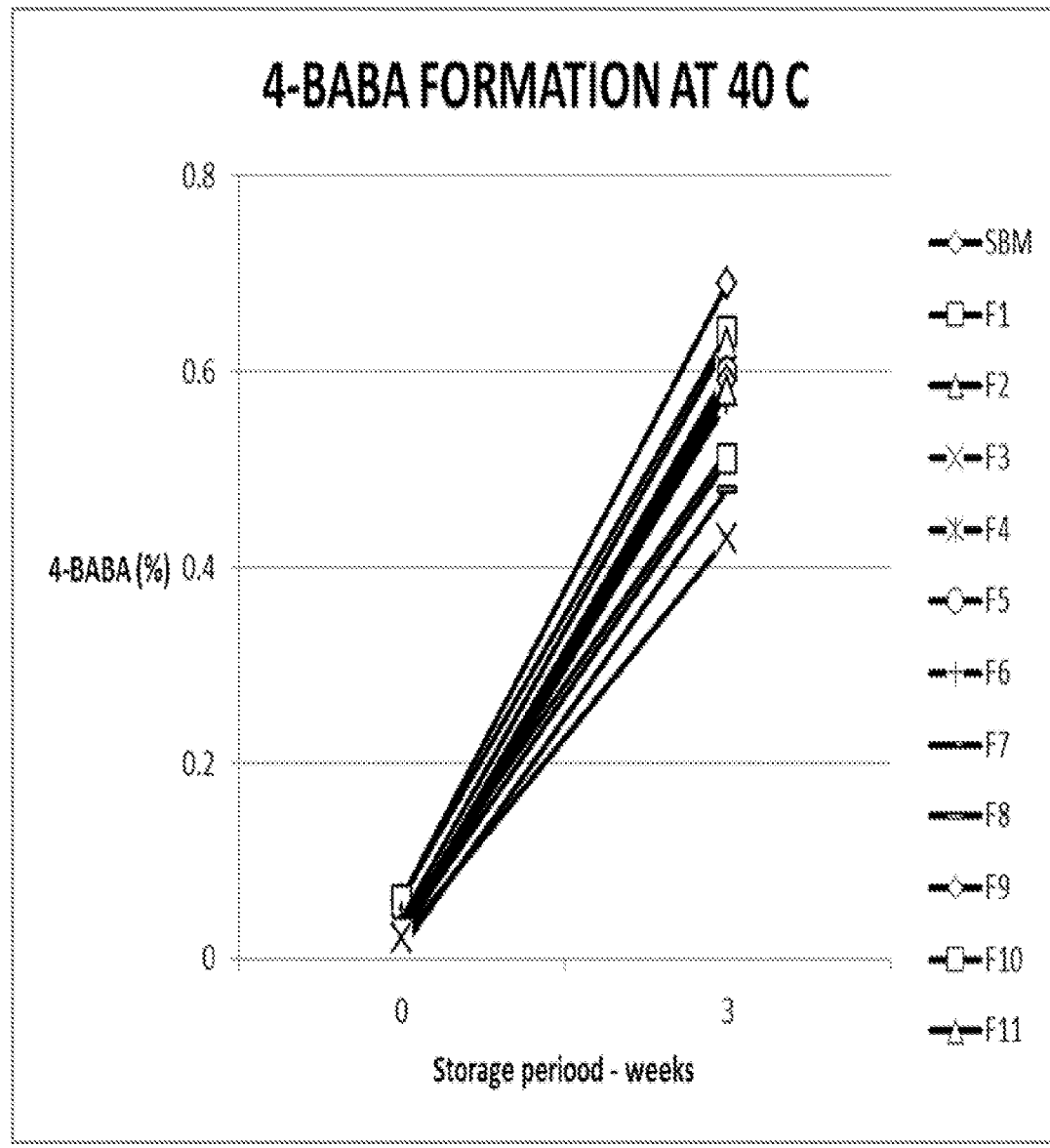
FIG. 3 is a plot of the formation of 4-BABA in exemplary embodiments of formulations of the disclosed invention when the formulations are stored for a period of time at 40° C.

The results from the testing at 40° C. are plotted and shown in FIG. 3.

Example 12

Viscosity of the Formulations of Example 9

Each of the formulations and the control described in Example 9 were tested for changes in viscosity following storage at ambient conditions (18° C. to 25° C. and ≤60% RH) and accelerated conditions (40±2° C. and 75%±5 RH). Samples in both ambient and accelerated conditions were tested at zero months and at 3 weeks. Viscosity measurements of the formulations were performed with the Brookfield HA DV-11+Pro viscometer using appropriate spindle and rotation speed at a temperature maintained between 23±2° C. The samples were placed in the sample adapter and maintained at the 23±2° C. for 30 minutes before measurement. Observations were recorded every 2 minutes until two consecutive readings were within ±10 cps. Generally spindle #21 was used for the measurements for formulations with viscosity less than 6000 cps, spindle #14 was used for viscosities higher than 6000 cps, and spindle #7 was used for thicker formulations with viscosities more than 200,000.

Results for the viscosity changes for each of the formulations is provided in Tables 30-31 for ambient temperature samples and Tables 32-33 for accelerated temperature samples.

TABLE 30

| Storage (Weeks) | CONTROL | F1 | F2 | F3 | F4 | F5 | F6 |
|---|---|---|---|---|---|---|---|
| 0 | 774 | 1088 | 1045 | 2305 | 1084 | 375500 | 2580 |
| 3 | 696 | 1064 | 1020 | 1615 | 1076 | 236300 | 2470 |

TABLE 31

| Storage (Weeks) | F7 | F8 | F9 | F10 | F11 | F12 |
|---|---|---|---|---|---|---|
| 0 | 9200 | 6655 | 10000 | 6280 | 820 | 5310 |
| 3 | 10960 | 8500 | 14375 | 5800 | 908 | 18620 |

Figure 4:
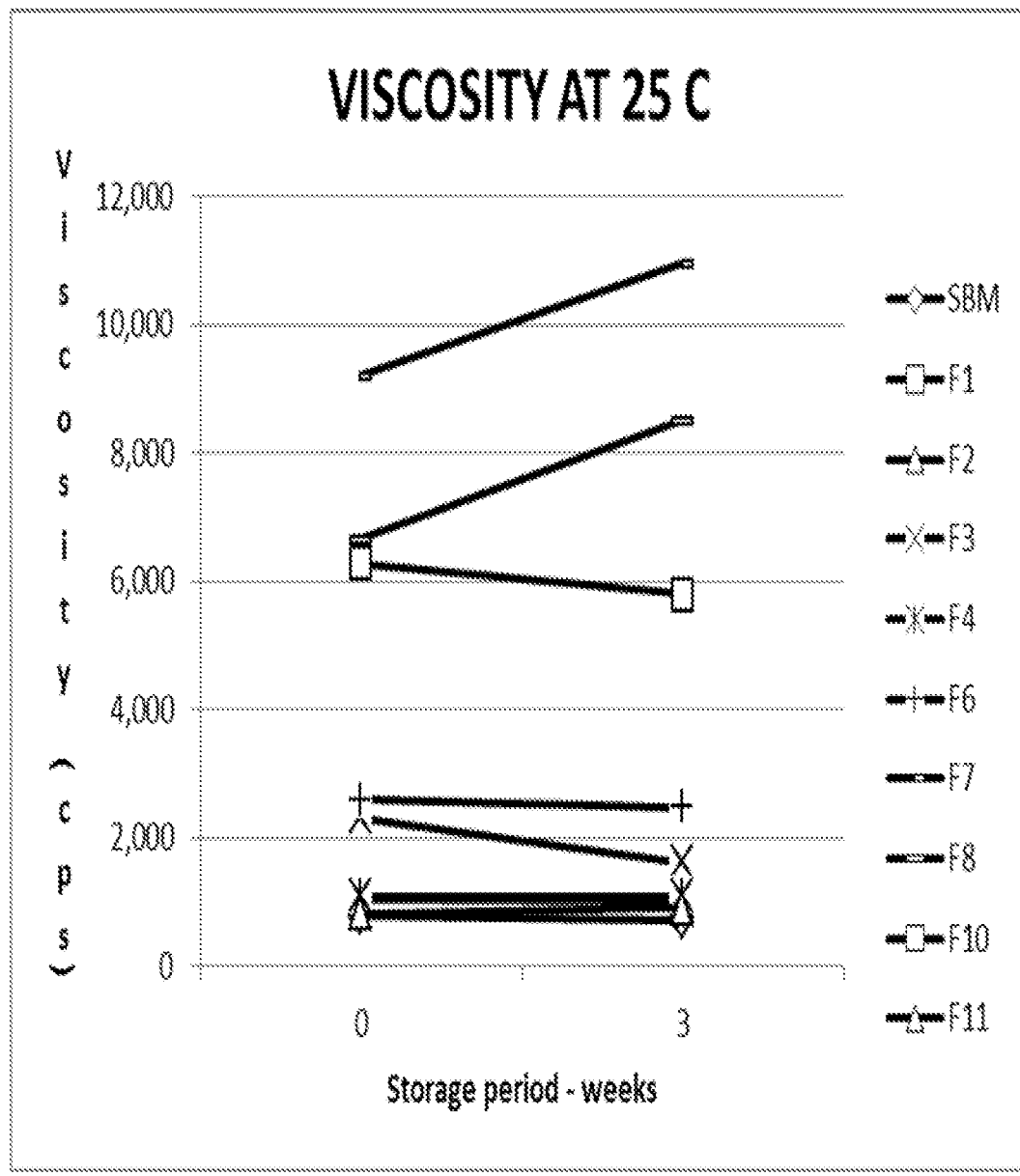
FIG. 4 is a plot of the viscosity of several exemplary formulations of the disclosed invention when the formulations are stored for a period of time at 25° C.

The results from the testing at 25° C. are plotted and shown in FIG. 4.

TABLE 32

| Storage (Weeks) | CONTROL | F1 | F2 | F3 | F4 | F5 | F6 |
|---|---|---|---|---|---|---|---|
| 0 | 774 | 1088 | 1045 | 2305 | 1084 | 375500 | 2580 |
| 3 | 762 | 1176 | 1210 | 1536 | 1140 | 329300 | 2520 |

TABLE 33

| Storage (Weeks) | F7 | F8 | F9 | F10 | F11 | F12 |
|---|---|---|---|---|---|---|
| 0 | 9200 | 6655 | 10000 | 6280 | 820 | 5310 |
| 3 | 8380 | 7900 | 13375 | 5470 | 792 | 9840 |

Figure 5:
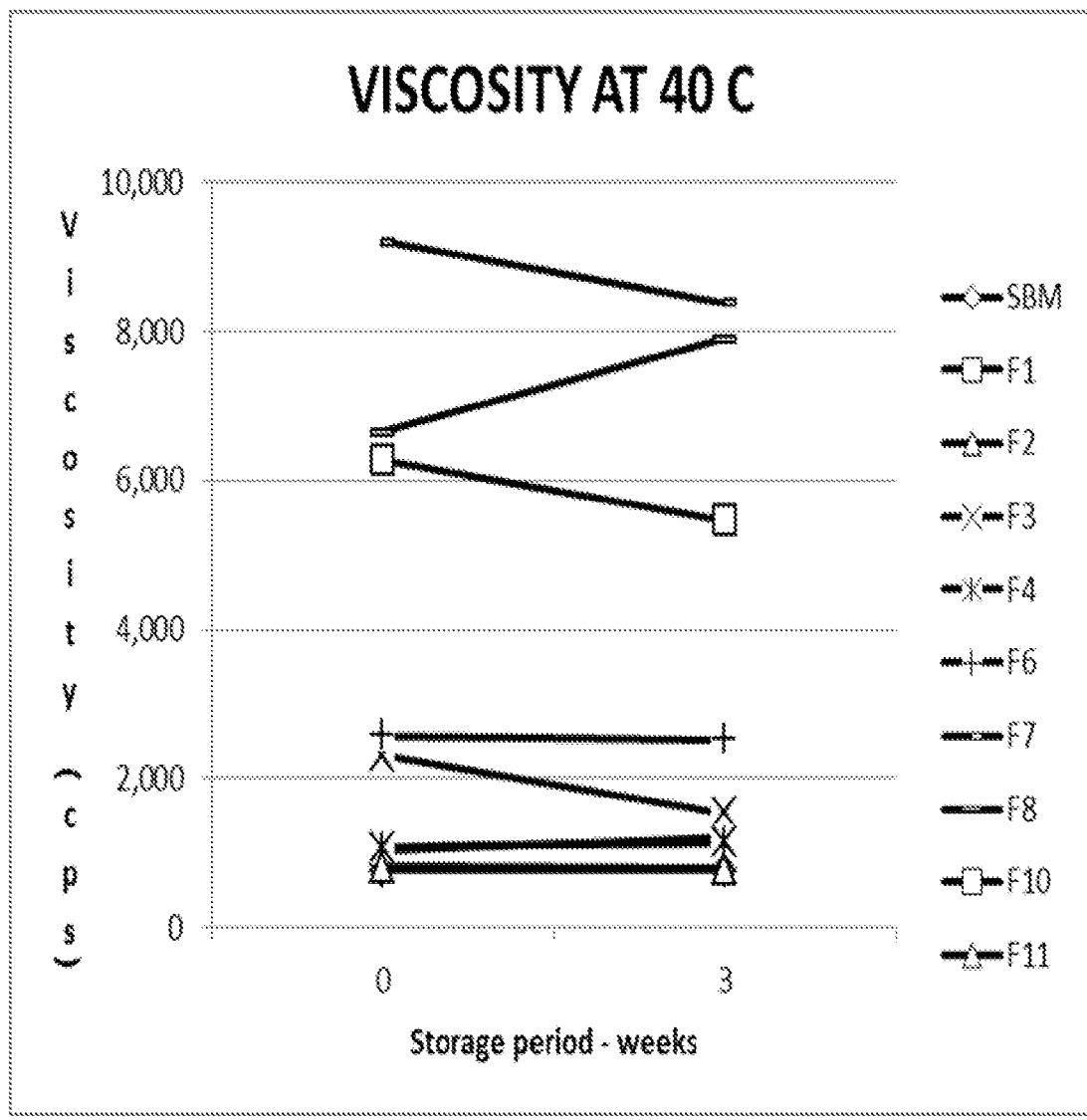
FIG. 5 is a plot of the viscosity of several exemplary formulations of the disclosed invention when the formulations are stored for a period of time at 40° C.

The results from the testing at 40° C. are plotted and shown in FIG. 5.

Example 13

Transdermal System for Delivering Local Anesthetics

Figure 6:
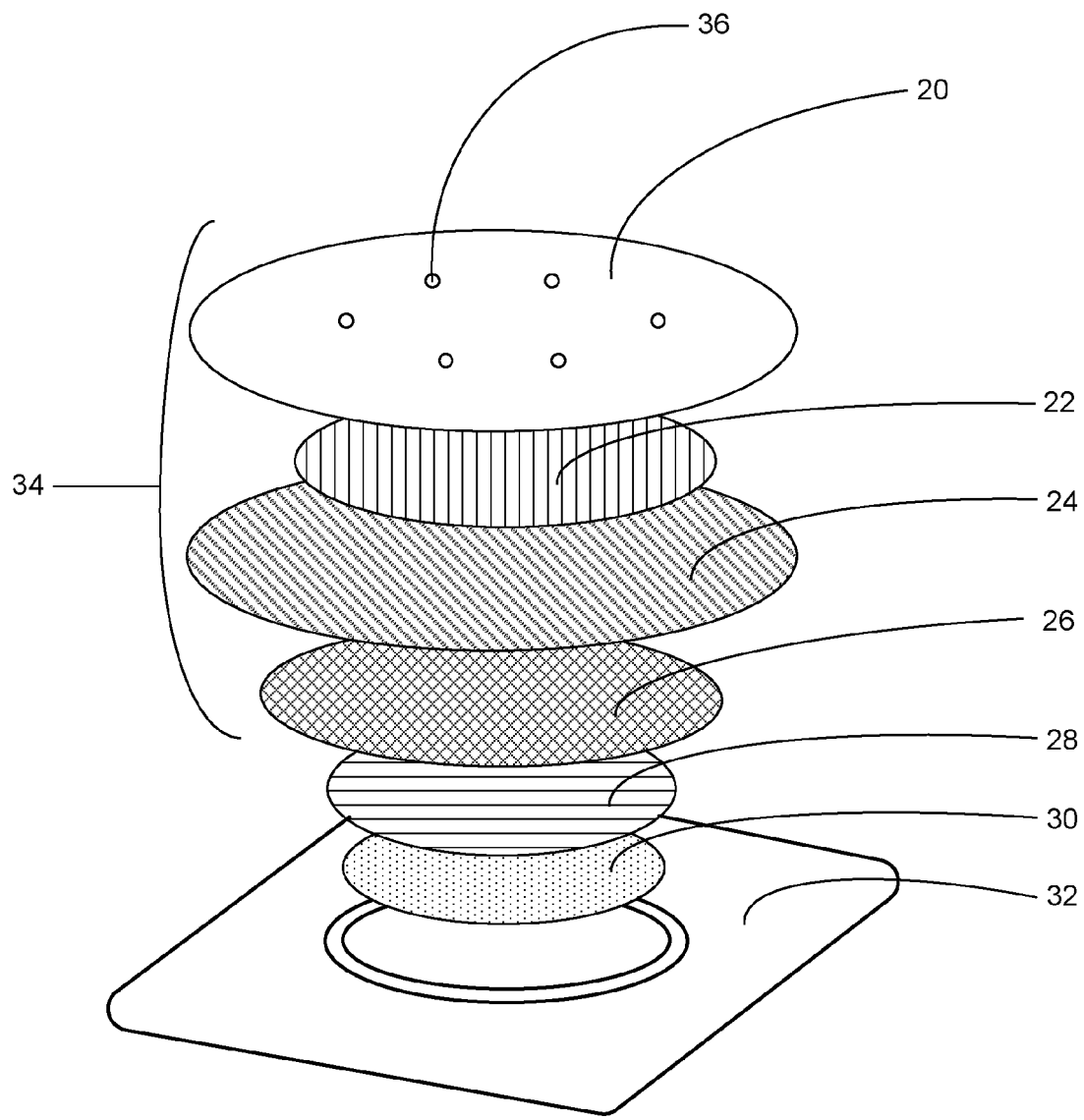
FIG. 6 is a schematic representation of an exemplary transdermal system of the present disclosure.

By way of example, a transdermal system that can include a topical formulation as disclosed herein is shown at FIG. 6. The system can include a heating component 34 and a local anesthetic formulation 30. The heating component can includes an air-impermeable top cover film 20 having a plurality of holes 36 therein. When exposed to ambient air, the holes allow for the passage of the ambient air through the air-impermeable top cover film to the exothermic chemical composition 22. The layer of exothermic chemical composition can be disposed between the air-impermeable top cover film and an adhesive film layer 24. The adhesive film layer extends beyond the circumference of the exothermic chemical composition layer and the local anesthetic formulation layer and can function, at least in part, to adhere to the analgesic system to a skin surface. A heat sealable film layer 26 can be below to the adhesive film layer and acts to impede the transfer of substances, particularly moisture, between the local anesthetic formulation layer and the exothermic chemical composition layer. Below the heat sealable film layer, a sodium-borate coated non-woven film layer 28 acts to gel the local anesthetic formulation during manufacturing. The topical formulation of the transdermal system can be adhered in an air and moisture impermeable packing tray 32 that holds the local anesthetic formulation during storage. The entire transdermal system can likewise be air sealed in a package to prevent premature activation of the exothermic chemical composition.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A topical formulation, comprising:
   a local anesthetic,
   a first compound, and
   a second compound,
   wherein the first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate.

2. The topical formulation of claim 1, wherein the local anesthetic is selected from the group consisting of lidocaine, tetracaine, benzocaine, prilocaine, bupivacaine, dimethocaine, mepivacaine, procaine, ropivacaine, trimecaine, articaine, and combinations thereof.

3. The topical formulation of claim 1, wherein the topical formulation includes lidocaine, tetracaine, or a combination thereof.

4. The topical formulation of claim 1, wherein the topical formulation includes a eutectic mixture of lidocaine and tetracaine.

5. The topical formulation of claim 1, wherein the local anesthetic is at least one local anesthetic base.

6. The topical formulation of claim 1, wherein the local anesthetic comprises at least about 30 wt % of the topical formulation.

7. The topical formulation of claim 1, wherein the local anesthetic comprises at least about 35 wt % of the topical formulation.

8. The topical formulation of claim 1, wherein the topical formulation further comprises water.

9. The topical formulation of claim 8, wherein the topical formulation has less phase separation after four weeks stored at 25° C. compared to a comparative formulation devoid of the first compound and the second compound and replaced with an equivalent wt % of water.

10. The topical formulation of claim 8, wherein the topical formulation has less phase separation after two weeks when stored at about 40° C. compared to a comparative formulation devoid of the first compound and the second compound and replaced with an equivalent wt % of water.

11. The topical formulation of claim 10, wherein the phase separation is at least 10% less after two weeks when stored at about 40° C. compared to a comparative formulation devoid of the first compound and the second compound and replaced with an equivalent wt % of water.

12. The topical formulation of claim 10, wherein the phase separation is at least 20% less after two weeks when stored at about 40° C. compared to a comparative formulation devoid of the first compound and the second compound and replaced with an equivalent wt % of water.

13. The topical formulation of claim 10, wherein the phase separation is at least 30% less after two weeks when stored at about 40° C. compared to a comparative formulation devoid of the first compound and the second compound and replaced with an equivalent wt % of water.

14. The topical formulation of claim 1, wherein the first compound comprises glycerol oleate and the second compound comprises isopropyl myristate.

15. The topical formulation of claim 1, wherein the first compound comprises glycerol oleate and the second compound comprises oleic acid.

16. The topical formulation of claim 1, wherein the first compound comprises glycerol oleate and the second compound comprises sodium lauryl sulfoacetate.

17. The topical formulation of claim 1, wherein the first compound comprises oleic acid and the second compound comprises isopropyl myristate.

18. The topical formulation of claim 1, wherein the first compound comprises oleic acid and the second compound comprises sodium lauryl sulfoacetate.

19. The topical formulation of claim 1, wherein the first compound comprises isopropyl myristate and the second compound comprises sodium lauryl sulfoacetate.

20. The topical formulation of claim 1, wherein the total concentration of the first compound and second compound is from about 1 wt % to about 15 wt %.

21. The topical formulation of claim 1, wherein the total concentration of the first compound and the second compound is from about 2 wt % to about 10 wt %.

22. The topical formulation of claim 1, wherein the weight ratio of the first compound to the second compound is about 1:9 to about 9:1.

23. The topical formulation of claim 1, wherein the weight ratio of the first compound to second compound is about 1:5 to about 5:1.

24. The topical formulation of claim 1, wherein the weight ratio of the first compound to second compound is about 1:3 to about 3:1.

25. The topical formulation of claim 1, further comprising one or more pharmaceutically acceptable excipients.

26. The topical formulation of claim 1, further comprising a solidification polymer.

27. The topical formulation of claim 26, wherein the solidification polymer is selected from the group consisting of polyvinyl alcohol, a monobutyl ester of the copolymer of methyl vinyl ether and maleic anhydride, poly(2-hydroxyethyl methacrylate), a copolymer of butyl methacrylate and methyl methacrylate, a copolymer of methacrylic acid and methyl methacrylate, and combinations thereof.

28. The topical formulation of claim 26, wherein the solidification polymer is polyvinyl alcohol.

29. The topical formulation of claim 1, further comprising a sorbitan fatty acid ester.

30. The topical formulation of claim 1, further comprising a paraben.

31. The topical formulation of claim 30, wherein the paraben is selected from the group consisting of methylparaben, propylparaben, ethylparaben, butylparaben, isobutylparaben, isopropyl paraben, benzyl paraben, and combinations thereof.

32. The topical formulation of claim 30, wherein the paraben includes methylparaben, propylparaben, or both.

33. The topical formulation of claim 1, wherein after three weeks stored at 25° C., the topical formulation has a lower concentration of 4-BABA compared to a comparative formulation devoid of the first compound and the second compound and replaced with an equivalent wt % of water.

34. The topical formulation of claim 33, wherein, after three weeks stored at 25° C., the topical formulation has a concentration of 4-BABA that is at least 5% lower compared to a comparative formulation devoid of the first compound and the second compound and replaced with an equivalent wt % of water.

35. The topical formulation of claim 33, wherein, after three weeks stored at 25° C., the topical formulation has a concentration of 4-BABA that is at least 10% lower compared to a comparative formulation devoid of the first compound and the second compound and replaced with an equivalent wt % of water.

36. The topical formulation of claim 1, wherein the topical formulation provides for improved flux of the drug as compared to a comparative formulation devoid of the first compound and the second compound and replaced with an equivalent wt % of water.

37. A method of treating a subject with existing pain or at risk of developing pain, comprising:
    applying a system for transdermal delivery of a local anesthetic to a skin surface of the subject, said system, comprising:
        a topical formulation, including a local anesthetic, a first compound, and a second compound, wherein the first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate; and optionally
        a heating component capable of heating the skin surface to a temperature of 35° C. to 47° C., and
    maintaining the system on the skin surface for a period of time of at least 15 minutes such that the topical formulation is in contact with the skin surface and the heating component is activated to apply the temperature to the topical formulation or the skin surface.

38. The method of claim 37, wherein the heating component is present in the system.

39. The method of claim 38, wherein the heating component begins heating at about the same time as the system is applied to the skin surface.

40. The method of claim 37, wherein the local anesthetic is selected from the group consisting of lidocaine, tetracaine, benzocaine, prilocaine, bupivacaine, dimethocaine, mepivacaine, procaine, ropivacaine, trimecaine, articaine, and combinations thereof.

41. The method of claim 37, wherein the topical formulation includes lidocaine, tetracaine, or a combination thereof.

42. The method of claim 37, wherein the topical formulation includes a eutectic mixture of lidocaine and tetracaine.

43. The method of claim 42, wherein the weight percentage of the eutectic mixture is at least 30 wt % of the topical formulation.

44. The method of claim 37, wherein the system is maintained on the skin surface for a period of time of at least 60 minutes.

45. The method of claim 37, wherein the system is maintained on the skin surface for a period of time of at least two hours.

46. The method of claim 37, wherein the topical formulation has a skin contact region having an area of 2 cm$^2$ to 200 cm$^2$.

47. The method of claim 37, wherein the topical formulation has a skin contact region having an area of 7 cm$^2$ to 150 cm$^2$.

48. The method of claim 37, wherein the topical formulation has a skin contact region having an area of 8 cm$^2$ to 15 cm$^2$.

49. The method of claim 37, wherein the topical formulation has a skin contact region having an area of about 2 cm$^2$ to about 12 cm$^2$.

50. The method of claim 37, wherein the topical formulation has a skin contact region having an area of about 25 cm$^2$ to about 35 cm$^2$.

51. The method of claim 37, wherein the topical formulation has a skin contact region having an area of about 15 cm$^2$ to about 20 cm$^2$.

52. The method of claim 37, wherein the local anesthetic is a local anesthetic base.

53. The method of claim 52, wherein the topical formulation includes two local anesthetics and the two local anesthetics form a eutectic mixture.

54. The method of claim 52, wherein the topical formulation includes a eutectic mixture of lidocaine and tetracaine.

55. The method of claim 37, wherein the topical formulation further comprises water.

56. The method of claim 55, wherein the topical formulation has less phase separation after four weeks stored at 25° C. compared to a comparative formulation devoid of the first compound and the second compound and replaced with an equivalent wt % of water.

57. The method of claim 37, wherein the first compound comprises glycerol oleate and the second compound comprises isopropyl myristate.

58. The method of claim 37, wherein the first compound comprises glycerol oleate and the second compound comprises oleic acid.

59. The method of claim 37, wherein the first compound comprises glycerol oleate and the second compound comprises sodium lauryl sulfoacetate.

60. The method of claim 37, wherein the first compound comprises oleic acid and the second compound comprises isopropyl myristate.

61. The method of claim 37, wherein the first compound comprises oleic acid and the second compound comprises sodium lauryl sulfoacetate.

62. The method of claim 37, wherein the first compound comprises isopropyl myristate and the second compound comprises sodium lauryl sulfoacetate.

63. The method of claim 37, wherein the total concentration of the first compound and second compound is from about 1 wt % to about 15 wt %.

64. The method of claim 37, wherein the weight ratio of the first compound to the second compound is about 1:9 to about 9:1.

65. The method of claim 37, wherein the method is for analgesicly treating existing pain.

66. The method of claim 65, wherein the existing pain is musculoskeletal pain.

67. The method of claim 65, wherein the existing pain is tendinopathy.

68. The method of claim 37, wherein the method is for anestisizing the skin prior to a painful medical procedure.

69. A method of improving the physical stability of a topical formulation including a local anesthetic, comprising admixing a first compound and a second compound with the local anesthetic and water, wherein the first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate.

70. The method of claim 69, wherein the topical formulation has less phase separation after four weeks stored at 25° C. compared to a comparative formulation devoid of the first compound and the second compound and replaced with an equivalent wt % of water.

71. The method of claim 70, wherein stability is improved following the storage for a period of at least 2 weeks at a temperature of 18° C. to about 25° C. compared to a comparative formulation devoid of the first compound and the second compound and replaced with an equivalent wt % of water.

72. The method of claim 69, wherein the local anesthetic is selected from the group consisting of lidocaine, tetracaine, benzocaine, prilocaine, bupivacaine, dimethocaine, mepivacaine, procaine, ropivacaine, trimecaine, articaine, and combinations thereof.

73. The method of claim 69, wherein the local anesthetic is a local anesthetic base.

74. The method of claim 73, wherein the topical formulation includes lidocaine, tetracaine, or a combination thereof.

75. The method of claim 74, wherein the topical formulation includes a eutectic mixture of lidocaine base and tetracaine base.

76. The method of claim 69, wherein the local anesthetic comprises at least about 30 wt % of the topical formulation.

77. The method of claim 69, wherein the formulation further comprises a polymer.

78. The method of claim 69, wherein the formulation further comprises a fatty acid ester.

79. The method of claim 69, wherein the formulation further comprises a paraben.

80. The method of claim 69, wherein the topical formulation further comprises water.

81. The method of claim 80, wherein the topical formulation has less phase separation after four weeks stored at 40° C. compared to a comparative formulation devoid of the first compound and the second compound and replaced with an equivalent wt % of water.

82. The method of claim 69, wherein the first compound comprises glycerol oleate and the second compound comprises isopropyl myristate.

83. The method of claim 69, wherein the first compound comprises glycerol oleate and the second compound comprises oleic acid.

84. The method of claim 69, wherein the first compound comprises glycerol oleate and the second compound comprises sodium lauryl sulfoacetate.

85. The method of claim 69, wherein the first compound comprises oleic acid and the second compound comprises isopropyl myristate.

86. The method of claim 69, wherein the first compound comprises oleic acid and the second compound comprises sodium lauryl sulfoacetate.

87. The method of claim 69, wherein the first compound comprises isopropyl myristate and the second compound comprises sodium lauryl sulfoacetate.

88. The method of claim 69, wherein the total concentration of the first compound and second compound is about 1 wt % to about 15 wt %.

89. The method of claim 69, wherein the weight ratio of the first compound to the second compound is about 1:9 to about 9:1.

90. A system for transdermal delivery of a local anesthetic, comprising:
a topical formulation, including a local anesthetic, a first compound, and a second compound, wherein the first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate; and
a heating component capable of heating the skin surface to a temperature of 35° C. to 47° C.

91. The system of claim 90, wherein the local anesthetic is selected from the group consisting of lidocaine, tetracaine, benzocaine, prilocaine, bupivacaine, dimethocaine, mepivacaine, procaine, ropivacaine, trimecaine, articaine, and combinations thereof.

92. The system of claim 90, wherein the local anesthetic includes lidocaine, tetracaine, or a combination thereof.

93. The system of claim 90, wherein the local anesthetic is a eutectic mixture of lidocaine base and tetracaine base.

94. The system of claim 93, wherein the weight percentage of the eutectic mixture is at least 30 wt % of the topical formulation.

95. The system of claim 90, wherein the local anesthetic is a local anesthetic base.

96. The system of claim 90, wherein the local anesthetic comprises at least about 30 wt % of the topical formulation.

97. The system of claim 90, wherein the local anesthetic comprises at least about 35 wt % of the topical formulation.

98. The system of claim 90, wherein the topical formulation further comprises water.

99. The system of claim 98, wherein the topical formulation has less phase separation after four weeks stored at 25° C. compared to a comparative formulation devoid of the first compound and the second compound and replaced with an equivalent wt % of water.

100. The system of claim 98, wherein the topical formulation has less phase separation after two weeks when stored at about 40° C. compared to a comparative formulation devoid of the first compound and the second compound and replaced with an equivalent wt % of water.

101. The system of claim 100, wherein the phase separation is at least 10% less after two weeks when stored at about 40° C. compared to a comparative formulation devoid of the first compound and the second compound and replaced with an equivalent wt % of water.

102. The system of claim 90, wherein the first compound comprises glycerol oleate and the second compound comprises isopropyl myristate.

103. The system of claim 90, wherein the first compound comprises glycerol oleate and the second compound comprises oleic acid.

104. The system of claim 90, wherein the first compound comprises glycerol oleate and the second compound comprises sodium lauryl sulfoacetate.

105. The system of claim 90, wherein the first compound comprises oleic acid and the second compound comprises isopropyl myristate.

106. The system of claim 90, wherein the first compound comprises oleic acid and the second compound comprises sodium lauryl sulfoacetate.

107. The system of claim 90, wherein the first compound comprises isopropyl myristate and the second compound comprises sodium lauryl sulfoacetate.

108. The system of claim 90, wherein the total concentration of the first compound and second compound is from about 1 wt % to about 15 wt %.

109. The system of claim 90, wherein the weight ratio of the first compound to the second compound is from about 1:9 to about 9:1.

110. The system of claim 90, further comprising a solidification polymer selected from the group consisting of polyvinyl alcohol, a monobutyl ester of the copolymer of methyl vinyl ether and maleic anhydride, poly(2-hydroxyethyl methacrylate), a copolymer of butyl methacrylate and methyl methacrylate, a copolymer of methacrylic acid and methyl methacrylate, and combinations thereof.

111. The system of claim 90, further comprising a sorbitan fatty acid ester.

112. The system of claim 90, further comprising a paraben selected from the group consisting of methylparaben, propylparaben, ethylparaben, butylparaben, isobutylparaben, isopropyl paraben, benzyl paraben, and combinations thereof.

113. The system of claim 90, wherein after three weeks stored at 25° C. the topical formulation has a lower concentration of 4-BABA compared to a comparative formulation devoid of the first compound and the second compound and replaced with an equivalent wt % of water.

114. The system of claim 113, wherein, after three weeks stored at 25° C., the topical formulation has a concentration of 4-BABA that is at least 5% lower compared to a comparative formulation devoid of the first compound and the second compound and replaced with an equivalent wt % of water.

115. The system of claim 90, wherein the heating component includes an exothermic heating material.

116. The system of claim 115, wherein the heating component includes an exothermic chemical composition layer.

117. The system of claim 116, wherein the system includes an air impermeable layer disposed on an upper surface of the chemical composition layer and having one or more holes therein.

118. The system of claim 115, wherein the system includes an activation tab removably adhered to an upper surface of the air impermeable layer and being configured to cover the one or more holes in the air impermeable layer and inhibit the passage of air through the holes prior to removal of the activation tab.

119. The system of claim 115, wherein the system includes an adhesive layer disposed on a lower surface of one or both of the exothermic chemical composition layer and the lower surface of the air impermeable layer, said adhesive layer being configured to adhere the system to a skin surface.

120. The system of claim 90, wherein the heating element is capable of heating the skin surface to a temperature of generates a controlled level of heat from about 36° C. to about 42° C.

121. The system of claim 90, wherein the topical formulation has a skin contact region having an area of 2 $cm^2$ to 200 $cm^2$.

122. The system of claim 90, wherein the topical formulation has a skin contact region having an area of 7 $cm^2$ to 150 $cm^2$.

123. The system of claim 90, wherein the topical formulation has a skin contact region having an area of 8 $cm^2$ to 15 $cm^2$.

124. The system of claim 90, wherein the topical formulation has a skin contact region having an area of about 2 $cm^2$ to about 12 $cm^2$.

125. The system of claim 90, wherein the topical formulation has a skin contact region having an area of about 25 $cm^2$ to about 35 $cm^2$.

126. The system of claim 90, wherein the topical formulation has a skin contact region having an area of about 15 cm$^2$ to about 20 cm$^2$.

127. The system of claim 90, wherein the system is substantially oval, round, square, triangular, or rectangular in shape.

* * * * *